(12) United States Patent
Olde et al.

(10) Patent No.: US 10,980,431 B2
(45) Date of Patent: Apr. 20, 2021

(54) APPARATUS AND METHOD FOR PREDICTION OF RAPID SYMPTOMATIC BLOOD PRESSURE DECREASE

(75) Inventors: Bo Olde, Lund (SE); Kristian Solem, Kavlinge (SE)

(73) Assignee: GAMBRO LUNDIA AB, Lund (SE)

(*) Notice: Subject to any disclaimer, the term of this patent is extended or adjusted under 35 U.S.C. 154(b) by 1262 days.

(21) Appl. No.: 13/519,559

(22) PCT Filed: Dec. 22, 2010

(86) PCT No.: PCT/EP2010/070555
§ 371 (c)(1),
(2), (4) Date: Sep. 12, 2012

(87) PCT Pub. No.: WO2011/080190
PCT Pub. Date: Jul. 7, 2011

(65) Prior Publication Data
US 2013/0006128 A1    Jan. 3, 2013

Related U.S. Application Data

(60) Provisional application No. 61/290,318, filed on Dec. 28, 2009.

(30) Foreign Application Priority Data

Dec. 28, 2009 (SE) .................... 0951031-4

(51) Int. Cl.
*A61B 5/0215* (2006.01)
*A61M 1/36* (2006.01)

(52) U.S. Cl.
CPC ......... *A61B 5/0215* (2013.01); *A61M 1/3639* (2013.01)

(58) Field of Classification Search
None
See application file for complete search history.

(56) References Cited

U.S. PATENT DOCUMENTS

| 3,882,861 A | 5/1975 | Kettering et al. |
| 3,946,731 A | 3/1976 | Lichtenstein |
| | (Continued) | |

FOREIGN PATENT DOCUMENTS

| CA | 2 574 529 A1 | 7/2007 |
| DE | 196 09 698 | 9/1997 |
| | (Continued) | |

OTHER PUBLICATIONS

Wabel et al., Ansätze zur Identifikation von Patientenparametern während der Hämodialysetherapie, Identification of Patient Parameters during Hemodialysis, vol. 50, Issue May 2002 (May 2002) pp. 220-227 ISSN (Print) 0178-2312, Published Online Sep. 25, 2009—English Translation—11 pages.
(Continued)

*Primary Examiner* — Michael R Bloch
(74) *Attorney, Agent, or Firm* — K&L Gates LLP

(57) ABSTRACT

A monitoring device is included in a medical system to implement a method for prediction of a rapid symptomatic drop in a subject's blood pressure, e.g. during a medical treatment such as dialysis. To this aim, a pulse shape parameter (pPS) with respect to a pulse generator of the subject is registered by means of a pressure sensor arranged in an extracorporeal blood flow circuit coupled to a cardiovascular system of the subject (P). The pressure sensor is configured to detect pressure variations in blood vessels of the subject (P). It is investigated, during measurement period, whether or not one or more of the pulse shape parameters fulfil a decision criterion. An output signal (a) is generated if the decision criterion is found to be fulfilled, to indicate a predicted rapid symptomatic blood pressure
(Continued)

decrease in the subject (P). The decision criterion may operate on pulse magnitude measures calculated for the received pulse shape parameters (pPS), or statistical dispersion measures calculated based on the thus-calculated pulse magnitude measures.

40 Claims, 35 Drawing Sheets

(56) References Cited

U.S. PATENT DOCUMENTS

| | | |
|---|---|---|
| 4,185,641 A | 1/1980 | Minior et al. |
| 4,239,047 A | 12/1980 | Griggs, III et al. |
| 4,277,227 A | 7/1981 | Jenkins |
| 4,324,663 A | 4/1982 | Hirel et al. |
| 4,353,368 A | 10/1982 | Slovak et al. |
| 4,392,847 A | 7/1983 | Whitney et al. |
| 4,450,527 A | 5/1984 | Sramek |
| 4,501,483 A | 2/1985 | Romansky et al. |
| 4,534,756 A | 8/1985 | Nelson |
| 4,541,282 A | 9/1985 | Auerweck et al. |
| 4,648,869 A | 3/1987 | Bobo, Jr. |
| 4,710,163 A | 12/1987 | Butterfield |
| 4,828,543 A | 5/1989 | Weiss et al. |
| 4,846,792 A | 7/1989 | Bobo, Jr. et al. |
| 4,923,598 A | 5/1990 | Schal |
| 4,924,874 A | 5/1990 | Murase |
| 4,959,050 A | 9/1990 | Bobo, Jr. |
| 4,972,826 A | 11/1990 | Koehler et al. |
| 4,979,940 A | 12/1990 | Bobo, Jr. et al. |
| 4,981,467 A | 1/1991 | Bobo, Jr. et al. |
| 5,026,348 A | 6/1991 | Venegas |
| 5,100,374 A | 3/1992 | Kageyama |
| 5,146,414 A | 9/1992 | McKown et al. |
| 5,311,871 A | 5/1994 | Yock |
| 5,390,679 A * | 2/1995 | Martin .......... 600/486 |
| 5,427,695 A | 6/1995 | Brown |
| 5,476,592 A * | 12/1995 | Simard ........ A61M 1/3462 210/321.69 |
| 5,557,263 A | 9/1996 | Fisher et al. |
| 5,693,008 A | 12/1997 | Brugger et al. |
| 5,790,036 A | 8/1998 | Fisher et al. |
| 5,830,365 A | 11/1998 | Schneditz |
| 5,863,421 A | 1/1999 | Peter, Jr. et al. |
| 5,910,252 A | 6/1999 | Truitt et al. |
| 6,066,261 A | 5/2000 | Spickermann |
| 6,071,421 A | 6/2000 | Brown |
| 6,077,443 A | 6/2000 | Goldau |
| 6,090,048 A | 7/2000 | Hertz et al. |
| 6,167,765 B1 | 1/2001 | Weitzel |
| 6,187,199 B1 | 2/2001 | Goldau |
| 6,200,485 B1 | 3/2001 | Kitaevich et al. |
| 6,221,040 B1 | 4/2001 | Kleinekofort |
| 6,337,049 B1 | 1/2002 | Tamari |
| 6,423,022 B1 * | 7/2002 | Roeher ............ A61M 1/16 210/646 |
| 6,572,576 B2 | 6/2003 | Brugger et al. |
| 6,575,927 B1 | 6/2003 | Weitzel et al. |
| 6,595,942 B2 | 7/2003 | Kleinekofort |
| 6,623,443 B1 | 9/2003 | Polaschegg |
| 6,649,063 B2 | 11/2003 | Brugger et al. |
| 6,663,585 B1 | 12/2003 | Ender |
| 6,730,055 B2 | 5/2004 | Bainbridge et al. |
| 6,736,789 B1 | 5/2004 | Spickermann |
| 6,767,333 B1 | 6/2004 | Muller et al. |
| 6,773,670 B2 | 8/2004 | Stringer et al. |
| 6,780,159 B2 | 8/2004 | Sandler et al. |
| 6,780,322 B1 * | 8/2004 | Bissler ............ A61M 1/16 210/103 |
| 6,804,991 B2 * | 10/2004 | Balschat et al. ........ 73/40.5 R |
| 6,827,698 B1 | 12/2004 | Kleinekofort |
| 6,880,404 B2 | 4/2005 | Uberreiter |
| 6,899,691 B2 | 5/2005 | Bainbridge et al. |
| 6,979,306 B2 | 12/2005 | Moll |
| 7,040,142 B2 | 5/2006 | Burbank |
| 7,060,047 B2 | 6/2006 | Lodi et al. |
| 7,087,033 B2 | 8/2006 | Brugger et al. |
| 7,169,352 B1 | 1/2007 | Felt et al. |
| 7,172,569 B2 | 2/2007 | Kleinekofort |
| 7,172,570 B2 | 2/2007 | Cavalcanti et al. |
| 7,276,041 B2 | 10/2007 | Moll |
| 7,410,473 B2 | 8/2008 | Levin et al. |
| 7,537,687 B2 | 5/2009 | Toyoda et al. |
| 7,615,028 B2 | 11/2009 | O'Mahony |
| 8,152,751 B2 | 4/2012 | Roger et al. |
| 8,197,421 B2 | 6/2012 | Freeman et al. |
| 8,603,020 B2 | 12/2013 | Roger et al. |
| 2001/0007930 A1 | 7/2001 | Kleinekofort |
| 2002/0004636 A1 | 1/2002 | Tsubata |
| 2002/0107449 A1 | 8/2002 | Roeher |
| 2002/0198483 A1 | 12/2002 | Wariar et al. |
| 2003/0009123 A1 | 1/2003 | Brugger et al. |
| 2003/0128125 A1 | 7/2003 | Burbank et al. |
| 2003/0130607 A1 | 7/2003 | Delvano et al. |
| 2003/0152482 A1 | 8/2003 | O'Mahony et al. |
| 2004/0030277 A1 | 2/2004 | O'Mahony et al. |
| 2004/0041792 A1 | 3/2004 | Criscione |
| 2004/0171977 A1 | 9/2004 | Paolini et al. |
| 2004/0186409 A1 | 9/2004 | Cavalcanti et al. |
| 2004/0228760 A1 | 11/2004 | Stringer et al. |
| 2005/0004502 A1 | 1/2005 | O'Mahony et al. |
| 2005/0010118 A1 | 1/2005 | Toyoda et al. |
| 2005/0131332 A1 | 6/2005 | Kelly et al. |
| 2005/0228298 A1 | 10/2005 | Banet et al. |
| 2005/0230313 A1 | 10/2005 | O'Mahony et al. |
| 2006/0074369 A1 * | 4/2006 | Oishi .............. A61B 5/02152 604/4.01 |
| 2006/0081517 A1 | 4/2006 | Toyoda et al. |
| 2006/0122552 A1 | 6/2006 | O'Mahony |
| 2007/0004996 A1 | 1/2007 | Lovejoy et al. |
| 2007/0004997 A1 | 1/2007 | Felt et al. |
| 2007/0010779 A1 | 1/2007 | Utterberg et al. |
| 2007/0078368 A1 | 4/2007 | Felt et al. |
| 2007/0093774 A1 | 4/2007 | Felt et al. |
| 2007/0108128 A1 | 5/2007 | Koperschmidt et al. |
| 2007/0112289 A1 | 5/2007 | Cavalcanti et al. |
| 2007/0179433 A1 | 8/2007 | Jonsson et al. |
| 2007/0215545 A1 * | 9/2007 | Bissler .............. A61M 1/16 210/646 |
| 2007/0232980 A1 | 10/2007 | Felt et al. |
| 2008/0183120 A1 | 1/2008 | Utterberg et al. |
| 2008/0067132 A1 | 3/2008 | Ross et al. |
| 2008/0108930 A1 | 5/2008 | Weitzel et al. |
| 2008/0171960 A1 | 7/2008 | Brieske et al. |
| 2008/0195022 A1 | 8/2008 | Lucke et al. |
| 2008/0214979 A1 | 9/2008 | Brugger et al. |
| 2009/0272678 A1 | 11/2009 | Sornmo et al. |
| 2010/0099995 A1 * | 4/2010 | Lian .............. A61N 1/3702 600/515 |

FOREIGN PATENT DOCUMENTS

| | | |
|---|---|---|
| DE | 198 48 235 | 3/2000 |
| DE | 10114383 | 10/2002 |
| EP | 0 121 931 | 10/1984 |
| EP | 0 232 599 | 8/1987 |
| EP | 0 300 315 | 1/1989 |
| EP | 0 332 330 | 9/1989 |
| EP | 0361793 | 4/1990 |
| EP | 0 498 324 A1 | 8/1992 |
| EP | 0895787 | 2/1999 |
| EP | 1 472 973 | 11/2004 |
| EP | 1 736 185 | 12/2006 |
| JP | 11104233 | 4/1999 |
| JP | 2005040518 | 2/2005 |
| JP | 2006/110118 | 4/2006 |
| JP | 2006/110120 | 4/2006 |
| KR | 10-2009-0015085 | 2/2009 |
| WO | WO 91/00113 | 1/1991 |
| WO | WO 97/10013 | 3/1997 |
| WO | 98/20918 | 5/1998 |
| WO | WO 99/29356 | 6/1999 |
| WO | WO 00/18451 | 4/2000 |

(56) References Cited

FOREIGN PATENT DOCUMENTS

| WO | WO 02/102441 | 12/2002 |
|---|---|---|
| WO | WO 03/002174 | 1/2003 |
| WO | WO 03/006944 | 1/2003 |
| WO | WO 03/058567 | 1/2003 |
| WO | WO 03/058608 | 1/2003 |
| WO | WO2005/019416 | 3/2005 |
| WO | WO 2006/122001 | 11/2006 |
| WO | 2007/141246 A2 | 12/2007 |
| WO | 2009/116872 A1 | 9/2009 |
| WO | 2009127683 | 10/2009 |
| WO | 2009/156174 A2 | 12/2009 |
| WO | 2009/156175 | 12/2009 |

OTHER PUBLICATIONS

Faizan Javed et al., "Changes in the Spectral Powers of Finger Photoplethysmorgraphic Waveform Variability in Hemodialysis Patients", 31st Annual International Conference of the IEEE EMBS, Sep. 2-6, 2009. pp. 3999-4002.

Jules Bassale, "Hypotension Prediction Arterial Blood Pressure Variability", Electrical and Computer Engineering, Portland State University ECE 457:Learning From Data, Spring 2001, pp. 1-4.

Saito Nagami et al, "The Study of New Alarm System that Detect Earlier Drop of Blood Pressure During Hemodialysis", Jpn J Artif Organs 26(2), 423-428 (1997) (with English abstract).

J. Bassale, "Hypotension Prediction Arterial Blood Pressure Variability," Electrical and Computer Engineering, Portland State University, ECE 457 (Spring 2001). 4 pages.

Translation of Korean Office Action issued in related Korean Patent Application No. 10-2012-7019881 dated Jul. 14, 2016.

Chen, et al. "Forecasting acute hypotensive episodes in intensive care patients based on a peripheral arterial blood pressure waveform." Computers in Cardiology, v. 36, 7 pages, (available at 2009 36th Annual Computers in Cardiology Conference, Park City Utah, Sep. 13-16, 2009). IEEE Catalog No. CFP09CAR-PRT. ISBN: 978-1-4244-7281-9.

* cited by examiner

DRAWINGS APPENDIX A

END DRAWINGS APPENDIX A

DRAWINGS APPENDIX B

END DRAWINGS APPENDIX B

APPARATUS AND METHOD FOR PREDICTION OF RAPID SYMPTOMATIC BLOOD PRESSURE DECREASE

RELATED APPLICATION

This is a U.S. National Phase of PCT/EP2010/070555 having an international filing date of Dec. 22, 2010, and claims priority to U.S. provisional patent application 61/290,318 filed Dec. 28, 2009, and Swedish patent application 0951031-4 filed Dec. 28, 2009, the entirety of all of these applications are incorporated by reference.

TECHNICAL FIELD

The present invention relates generally to detection of the onset of rapid (i.e. acute) symptomatic drop in a subject's blood pressure. More particularly the invention relates to a monitoring arrangement, a medical system, a method, a computer program, and a computer readable medium. The present invention is e.g. applicable in arrangements for extracorporeal blood treatment.

BACKGROUND ART

In many situations, it may be important to detect potential hypotension, and if possible avoid the actual occurrence thereof, for example when performing artificial blood purification. The human body consists of approximately 60% water—a level which is important to maintain for survival. While it is unproblematic to provide the body with new water, disposal of surplus water is a major problem in renal patients. The task of the normal kidney is to remove superfluous fluid from the blood, such as water, urea and other waste products. The resulting urine is transferred to the bladder and finally leaves the body during urination. The kidney's second task is to regulate for example the balance of acid and base. With malfunctioning kidneys, disorders may develop in most major body organs, a syndrome called uremia. If uremia remains untreated, it will lead to death. Uremia is treated either by kidney transplantation, or some kind of blood treatment, extracorporeal or intracorporeal.

Events of hypotension may be divided into a) "basic hypotension" caused by low blood pressure, b) "acute hypotension" caused by rapidly occurring low blood pressure which may intensify, c) "symptomatic hypotension" caused by low blood pressure and which cause symptoms, d) "rapid symptomatic hypotension" caused by rapid blood pressure decrease with symptoms, and e) "non-acute/acute intradialytic hypotension" caused by slow or rapid blood pressure decrease during dialysis.

The etiology of dialysis-induced hypotension is often considered to be volume depletion, originating from an ultrafiltration rate which exceeds the reabsorption rate. Volume depletion causes a reduction in the blood volume which returns to the heart, resulting in decreased cardiac filling and thus decreased cardiac output, which may lead to hypotension. Besides hypovolemia, other factors are believed to contribute to intradialytic hypotension as well, of which failing compensatory mechanisms are often considered, e.g. reflected by factors such as autonomic nervous system (ANS), cardiac output, and capillary vasoconstriction. Additionally, inter-dialytic hypotension may be caused by rapid or slow blood pressure decrease between dialysis sessions. In this context, hypotension occurring shortly after completing a dialysis treatment, e.g. within a few hours, may also be regarded to be induced by the dialysis treatment together with intra-dialytic hypotension.

Decreased cardiac output will reduce the amount of blood which reaches the capillaries, and thus cause the magnitude of the capillary pulse to decrease. Capillary vasoconstriction is an important autonomic counterregulation in order to prevent hypotension, in which the blood pressure is increased. The blood volume in the capillaries will decrease during capillary vasoconstriction, causing the magnitude of the capillary pulse to decrease. Hence, both increase in cardiac output and elevated capillary vasoconstriction may contribute to preventing intradialytic hypotension, since both factors reflect compensatory mechanisms. Normally these compensatory mechanisms manage to maintain blood pressure. However, failing mechanisms may cause hypotension. Thus, both cardiac output and capillary vasoconstriction will contribute to a decrease in the magnitude of capillary pulse prior to a hypotension.

No products are yet available on the market that provides early warnings of dialysis-induced acute symptomatic blood pressure drops. Since dialysis-induced hypotension leads to increased need for medical service and higher costs, it is desirable to develop clinical methods for prediction of intradialytic hypotension which may lead to the prevention of such events. In addition, with known methods and apparatuses, it has not been possible to distinguish the two effects from each other, in particular not in real-time.

A recently disclosed method in WO2007/141246 A2 "Prediction of rapid symptomatic blood pressure decrease" suggests detection based on a decrease in the magnitude of the photoplethysmography (PPG) pulse delivered by a pulse oximeter based on an optical technique for measuring blood volume changes in the microvascular bed of tissue, e.g. capillaries. A similar method is disclosed in US2008/0067132 A1 "Method for using photoplethysmography to optimize fluid removal during renal replacement therapy by hemodialysis or hemofiltration".

Another method is disclosed in CA2574529 A1 "Dialysis machine with arterial pressure monitoring by measuring oxygen saturation" and is based on the short-term variability in oxygen saturation measured on the arterial line of a dialysis machine.

During an artificial blood purification process, such as extracorporeal blood treatment, it is common that the patient suffers from symptomatic hypotension, characterized by a blood pressure drop with symptoms in the form of cramps, nausea, vomiting and sometimes fainting. Such an event is not only strenuous for the patient, but also requires considerable attention from the staff overseeing the treatment. Consequently, during such blood treatment, it is highly desirable to detect the onset of symptomatic hypotension and preventing it from coming about.

However, there are other examples of situations in which it is vital to predict, and if possible prevent, rapid symptomatic hypotension. For instance fighter plane pilots are often subjected to forces that risk result in that the pilot faints. However, also operators of other types of vehicles, crafts and machines may need similar surveillance in order to reduce hazards to the operators, other people and various material goods.

SUMMARY

The object of the present invention is therefore to alleviate the problem above and thus accomplish an uncomplicated solution by means of which the onset of acute symptomatic blood pressure decrease may be detected at a point in time when any effects thereof, still may be avoided.

According to a first aspect of the invention, the object is achieved by a monitoring device for predicting rapid symptomatic blood pressure decrease in a subject, the device comprising: an input for receiving measurement data from at least one pressure sensor in an extracorporeal blood flow circuit coupled to a cardiovascular system of the subject, the measurement data comprising a time sequence of pulse shape parameters representing pressure variations in at least one blood vessel of the subject, and a data analysis part adapted to repeatedly receive the pulse shape parameters, investigate whether or not a measure of one or more of the pulse shape parameters fulfils a decision criterion, and if so, cause an output signal to be generated, the output signal indicating a predicted rapid symptomatic blood pressure decrease in the subject. Hence, one or more pressure sensors in an extracorporeal blood flow circuit may be used for retrieving a pulse shape parameter originating from a pulse generator of the subject. An important advantage by this design is that an early hypotension warning may be provided based on comparatively small processing resources and sensors being simple and cost-efficient.

In one embodiment, the data analysis part is further adapted to: obtain a reference measure; calculate, during a measurement period, a respective pulse measure based on each of a number of received pulse shape parameters; investigate, during the measurement period, whether or not the decision criterion, which is given relative to the reference measure, is fulfilled based on one or more of the pulse measures; and if so, causing the output signal to be generated. Pulse magnitude as well as pulse magnitude variability may be used for prediction of occurrence of a hypotension event. The reference measurement may be predetermined or obtained from a previous measurement and it may for instance be a threshold value.

According to one embodiment, the pulse measure is based on an average of a number of pulse magnitude measures. Averaging a number of pulse measures may increase the accuracy. For instance, the signal processor may be configured to generate an average temporal shape by: aligning and combining, e.g. based on timing data, a subset of pulse signal segments.

According to one embodiment, the reference measure is a threshold value, and the decision criterion is fulfilled when a pulse measure exceeds the threshold value. With exceeding, it is to be construed as passing or crossing, i.e. above or below. For instance, where the pulse measure is represented by the pulse magnitude measure, the decision criterion may be fulfilled when it is below the threshold value, and where the pulse measure is represented by a statistical dispersion measure, the decision criterion may be fulfilled when it is above the threshold value.

According to one embodiment, the data analysis part is further adapted to: calculate as the reference measure an initial pulse measure based on at least one pulse shape parameter received at a first instance, and store the initial pulse measure in a memory means associated with the surveillance device, wherein the measurement period is subsequent to the first instance. Thus, a pulse measure obtained at one instance, such as at the beginning of a treatment, may be compared with subsequent measurements. Hence, the decision criterion may for instance be a predetermined deviation from the initial pulse measure acting as the reference measure. Depending on embodiment, the initial pulse measure may be an initial pulse magnitude measure or an initial statistical dispersion measure of initial pulse magnitude measures.

According to one embodiment, the data analysis part is adapted to regard the decision criterion as fulfilled if: an examined pulse measure fulfils a first partial decision criterion calculated based on the initial pulse measure, and a predetermined amount of the pulse measures of the pulse shape parameters received within a subsequent test period fulfils a second partial decision criterion. In addition to, or alternatively, the dispersion of pulse magnitude measures may also be used for prediction of the occurrence of a hypotension event, in combination or separate from the use of the pulse magnitude measure. Hence, according to one embodiment, one (main) decision criterion may be fulfilled by the fulfillment of various partial decision criteria. As an advantage, reliability as to the detection may thus be improved.

According to one embodiment, the predetermined amount is a value representing approximately 50% to approximately 100% of the pulse measures calculated for the pulse shape parameters received within the test period.

According to one embodiment, the predetermined amount represents all the pulse measures calculated for the pulse shape parameters received within the test period.

According to one embodiment, the test period is an interval selected from a range extending from approximately one minute to approximately fifteen minutes. According to one embodiment, the test period is approximately five minutes long. Thus, depending on the threshold value, the predetermined amount of pulse magnitude measures required to fulfil the decision criterion and the test period length selected, a robust and reliable hypotension warning may be obtained for a large variety of subjects and applications.

According to one embodiment, the data analysis part is adapted to calculate the decision criterion by: normalizing the initial pulse measure, and dividing the normalized initial pulse measure by a predefined denominator. Hence, an unbiased comparison with the initial status may be made.

According to one embodiment, the analysis part is adapted to, during the measurement period, calculate a pulse measure for a received pulse shape parameter by dividing an original measure with the initial pulse measure.

According to one embodiment, the predefined denominator is a value selected from a range extending from approximately 1.2 to approximately 5 where the pulse measure is a pulse magnitude measure and from approximately 0.2 to approximately 0.8 where the pulse measure is a statistical dispersion measure of pulse magnitude measures. Hence, by selecting the threshold value, the algorithm may be calibrated regarding the length of the test period to attain a desired balance between early warning and false alarms. Generally, when the pulse measure is a pulse magnitude measure, a relatively large denominator requires a comparatively short test period, and vice versa. Conversely, when the pulse measure is a statistical dispersion measure, a relatively small denominator requires a comparatively short test period, and vice versa.

According to one embodiment, the monitoring device comprises an auxiliary input for receiving auxiliary measurement data from an auxiliary recording means adapted to repeatedly register a bio-impedance parameter representing a degree of contraction of the subject's capillary blood vessels, and the data analysis part is further adapted to receive the bio-impedance parameter, investigate whether or not the bio-impedance parameter fulfils an auxiliary decision criterion, and if so, generate the output signal. Hence, a complementary hypotension detection means is provided, and thereby a more reliable function.

According to one embodiment, the monitoring device is adapted to predict rapid symptomatic blood pressure decrease in a subject undergoing blood treatment, wherein the data analysis part is adapted to calculate the initial pulse measure based on one or more pulse shape parameters received during an initial phase of the blood treatment. Thus, the hypotension detection is based on a reference measure being relatively unaffected by the treatment. This further enhances the reliability.

According to one embodiment, the monitoring device is further configured to activate systems of a dialysis monitor to counter-act the occurrence of a hypotension event including any of adjusting a rate of fluid removal from the subject by reducing and/or stopping the rate of fluid removal in case of fulfilled decision criterion, increasing the conductivity in the dialysis fluid, supplying a saline bolus to a blood line connected to the cardiovascular system of the subject, adjusting the positioning of the subject, setting a dialysis monitor in bypass, or any combinations thereof. Hence, the dialysis monitor may execute preventive actions or counter-measurements to prevent and/or reduce the risk of hypotension of the subject. For instance, the activation of counter-measure systems may be triggered by the output signal. According to one embodiment, the output is a counter-acting operation induced by the monitoring device and the output signal is an operation triggering signal.

According to a second aspect of the invention, the object is achieved by a monitoring arrangement for predicting rapid symptomatic blood pressure decrease in a subject, the arrangement comprising: an extracorporeal blood flow circuit configured to be coupled to a cardiovascular system of the subject, said extracorporeal blood flow circuit comprising at least one pressure sensor for generating measurement data comprising a time sequence of pulse shape parameters representing pressure variations in at least one blood vessel of the subject; and the monitoring device according to the first aspect of the invention.

According to a third aspect of the invention, the object is achieved by a medical system adapted to perform blood treatment of a subject, wherein the system comprises: a dialysis machine adapted to perform extracorporeal blood treatment of the subject and comprising an extracorporeal blood flow circuit configured to be coupled to a cardiovascular system of the subject, said extracorporeal blood flow circuit comprising at least one pressure sensor for generating measurement data comprising a time sequence of pulse shape parameters representing pressure variations in at least one blood vessel of the subject; and the monitoring device according to the first aspect of the invention. Hence, blood treatment and hypotension surveillance may be effected in parallel in a straightforward manner.

According to a fourth aspect of the invention, the object is achieved by a method for predicting rapid symptomatic blood pressure decrease in a subject, the method comprising: receiving measurement data from at least one pressure sensor in an extracorporeal blood flow circuit coupled to a cardiovascular system of the subject, the measurement data comprising a time sequence of pulse shape parameters representing pressure variations in at least one blood vessel of the subject; investigating whether or not a measure of one or more of the pulse shape parameters fulfils a decision criterion; and causing, if the decision criterion is fulfilled, an output signal to be generated, the output signal indicating a predicted rapid symptomatic blood pressure decrease in the subject. The advantages of this method, as well as the embodiments thereof, are apparent from the discussion hereinabove with reference to the proposed monitoring device.

According to a fifth aspect of the invention, the object is achieved by a computer program directly loadable into the internal memory of a computer, comprising software for controlling the proposed method.

According to a sixth aspect of the invention, the object is achieved by a computer readable medium, having a program recorded thereon, where the program is to make a computer control the proposed method.

The generated output signal may be an alarm signal or trigger for a treatment monitor such as a dialysis monitor to initiate an operating mode to prevent a hypotension event from occurring.

Advantages with the aspects and embodiments of the present invention may include a reduced need for attaching external devices to the subject, hence a reduction or elimination of additional discomfort to the subject. In addition, with the aspects and embodiments of the present invention the following advantages are enabled: no need for additional disinfection of medical devices, cost-efficiency, no sensitivity to mechanical disturbances such as movement, and no communication between the treatment device, e.g. dialysis monitor, and an external device is required to allow appropriate counter-measures.

Embodiments of the second to sixth aspects of the invention may correspond to the above-identified embodiments of the first aspect of the invention.

Still other objectives, features, aspects and advantages of the present invention will appear from the following detailed description and the appendices, from the attached claims as well as from the drawings.

BRIEF DESCRIPTION OF THE DRAWINGS

The present invention is now to be explained more closely by means of preferred embodiments, which are disclosed as examples, and with reference to the attached drawings.

I. OVERVIEW

In the following, for the purpose of illustration only, an implementation of the inventive concept for predicting rapid symptomatic blood pressure decrease in a subject is described in the context of extracorporeal blood treatment. This is only an example, and the monitoring process may be equally implemented in combination with any one of the other monitoring techniques discussed below.

In the context of this specification, capillary pulse refers to volume changes in peripheral vessels. Furthermore, hypotension, a hypotension event and the like are examples of a condition involving rapid symptomatic blood pressure decrease. Within the context of this specification, a pulse power measure is the same as a pulse magnitude measure.

The pressure variations in at least one blood vessel of the subject may have as origin a pulse generator of the subject such as the heart or breathing system or from an external pulse generator coupled to the subject and inducing the pressure variations to the blood vessel.

Figure 1:
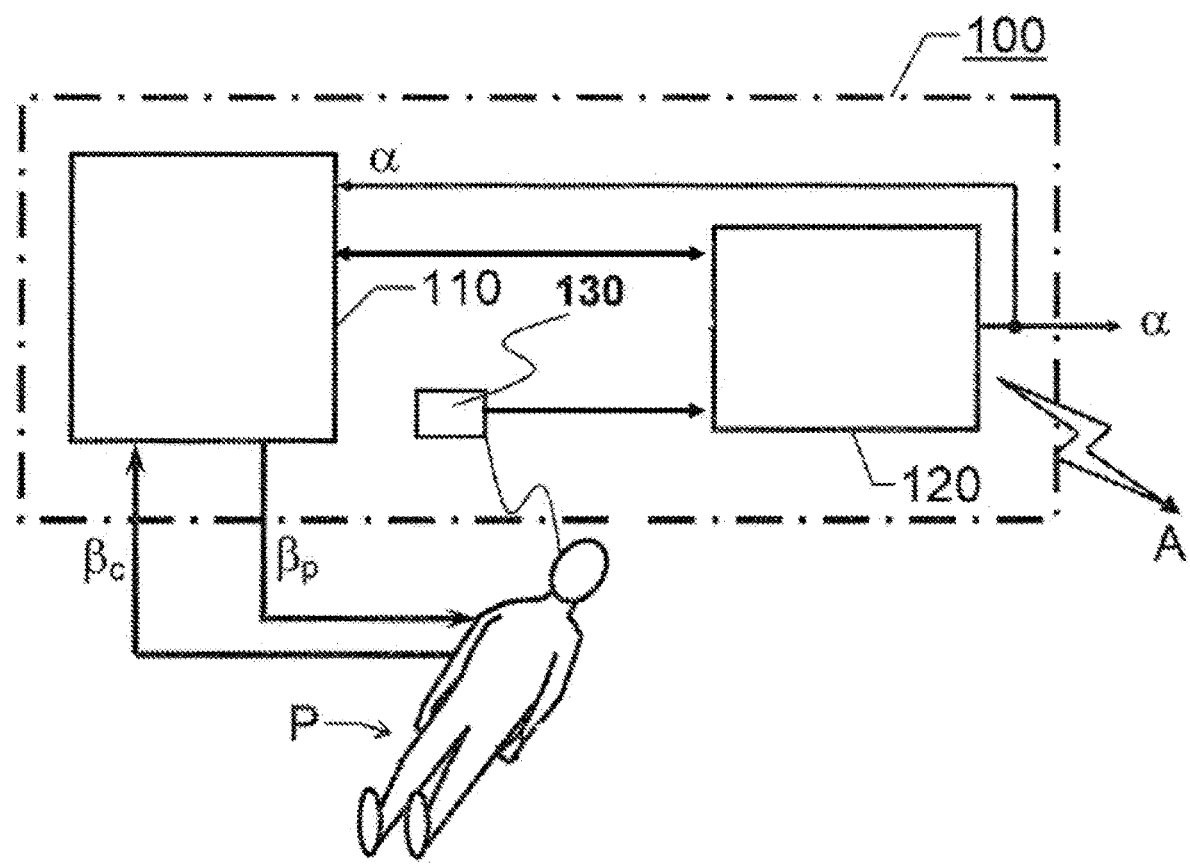
FIG. 1 shows a schematic view of a system for blood treatment including an extracorporeal blood flow circuit.

FIG. 1 shows a block diagram over a medical system 100 according to one embodiment of the invention for performing blood treatment of a subject P. To this aim the medical system 100 includes a dialysis machine 110, which may be adapted to perform extracorporeal blood treatment of the subject P, i.e. the machine 110 is adapted to extract contaminated blood βc from the subject P and return purified blood βp to the subject P.

The system 100 also includes a monitoring device 120 according to the present invention for predicting any rapid blood pressure decreases being potentially unhealthy to the subject P. Thus, in parallel with cleaning the subject's P blood, the monitoring arrangement 120 monitors him/her regarding the risk that acute symptomatic hypotension occurs. The monitoring device 120 may be an integral component of the dialysis machine 110.

In case of risk for acute symptomatic hypotension, the monitoring device 120 may issue an alarm signal α, such that the overseeing staff may be informed and/or the dialysis machine 110 may be controlled to adjust its treatment parameter in order to avoid a hypotension situation. This type of adjustment is symbolized by means of a feedback signal α from the monitoring device 120 to the dialysis machine 110.

Figure 2:
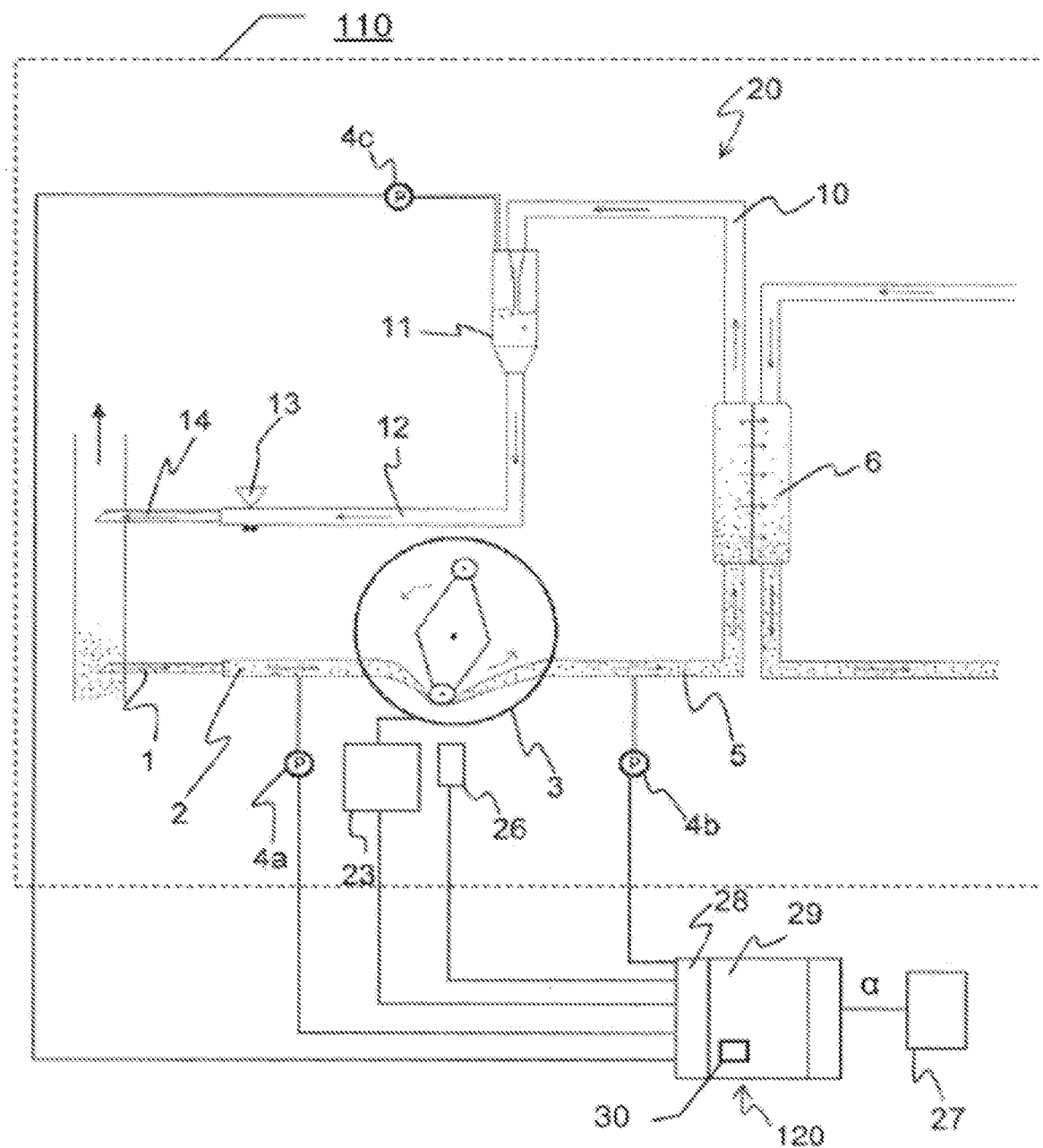
FIG. 2 is a schematic view of a system for hemodialysis treatment including an extracorporeal blood flow circuit.

Turning to FIG. 2, it shows a more detailed view of the medical system 100 comprising the monitoring device 120 and an extracorporeal system or extracorporeal blood flow circuit 20 of the dialysis machine 110.

The monitoring device 120 is connected to receive measurement data from a pulse recording means. The pulse recording means may comprise any of an arterial pressure sensor 4a, a system pressure sensor 4b and a venous pressure sensor 4c. The pulse recording means 4a, 4b, 4c may be a commonly integrated component of the dialysis machine 110. The pressure sensors 4a, 4b, 4c are adapted to generate measurement data that reflects pressure response variations in at least one blood vessel of the subject P. From the measurement data, the monitoring device 120 is adapted to generate a pressure signal S and to process the signal S for calculation of a sequence of pulse magnitude measures that represent pressure pulses (also denoted "patient pulses" herein) originating from one or more pulse generators in the subject P, such as the heart or breathing system. Possibly, in order to detect the often relatively weak pressure waves, it may be necessary to enhance the signal and detection of pulses, and at least partially eliminate pressure influence from pump(s) in the dialysis machine 110.

Thus, in the various embodiments described herein, pulse generators in the subject P and in the extracorporeal blood flow circuit 20 generate pressure waves which propagate in the liquid system extending from the respective pulse generator to a pressure sensor 4a-4c, which is in direct or indirect hydrostatic contact with the liquid system. A "pressure wave" is a mechanical wave in the form of a disturbance that travels or propagates through a material or substance. The pressure waves typically propagate in the liquid system at a velocity of about 3-20 m/s. The pressure sensor 4a-4c generates measurement data that forms a pressure pulse for each pressure wave. A "pressure pulse" or "pulse" is thus a set of data samples that define a local increase or decrease (depending on implementation) in signal magnitude within a time-dependent measurement signal ("pressure signal"). The pressure pulses appear at a rate proportional to the generation rate of the pressure waves at the pulse generator. The pressure sensor 4a-4c may be of any type, e.g. operating by resistive, capacitive, inductive, magnetic or optical sensing, and using one or more diaphragms, bellows, Bourdon tubes, piezo-electrical components, semiconductor components, strain gauges, resonant wires, accelerometers, bioimpedance, etc.

The monitoring device 120 is adapted to register a sequence of pulse shape parameters $p_{PS}$ based on the pressure signal S. As used herein, a "pulse shape parameter $p_{PS}$" refers to a signal segment in the pressure signal S or a corresponding monitoring signal, i.e. a sequence of signal values (pressure values) within a time window. The sequence of pulse shape parameters $p_{PS}$ thus represent different signal segments in the pressure/monitoring signal, where the signal segments may or may not be overlapping. The signal segment may, but need not, be selected so as to contain at least part of at least one patient pulse. From each pulse shape parameter $p_{PS}$, the monitoring device 120 is adapted to calculate a pulse magnitude measure PM. The pulse magnitude measure PM represents the magnitude of the signal values in the signal segment. The pulse magnitude measure PM is then evaluated for detection of a pattern indicating an upcoming symptomatic blood pressure decrease in the subject P, e.g. by comparing of the pulse magnitude measure PM with a threshold, or by calculating a statistical dispersion measure SM for a number of subsequent pulse magnitude measures, or a combination of the two. The detection techniques will be explained in detail in Section II below.

It is to be understood that the pressure sensor(s) are configured to monitor a relatively slowly varying baseline and a pulsatile response caused by heartbeats, breathing or autonomous regulation. Thus, the pressure signal S is comprised of pulsatile components, related to cardiac rhythm, breathing and autonomous regulation, which is superimposed on the slowly varying baseline.

In the illustrated embodiment, the extracorporeal blood flow circuit 20 is of a type which is used for dialysis. The extracorporeal blood flow circuit 20 comprises components 1-14 to be described in the following. Thus, the extracorporeal blood flow circuit 20 comprises an access device for blood extraction in the form of an arterial needle 1, and an arterial tube segment 2 which connects the arterial needle 1 to a blood pump 3 which may be of peristaltic type, as indicated. At the inlet of the pump there is a pressure sensor 4a, hereafter referred to as arterial sensor, which measures the pressure before the pump in the arterial tube segment 2. The blood pump 3 forces the blood, via a tube segment 5, to the blood-side of a dialyser 6. Many dialysis machines are additionally provided with a pressure sensor 4b that measures the pressure between the blood pump 3 and the dialyser 6. The blood is lead via a tube segment 10 from the blood-side of the dialyser 6 to a venous drip chamber or deaeration chamber 11 and from there back to the patient via a venous tube segment 12 and an access device for blood reintroduction in the form of a venous needle 14. A pressure sensor 4c, hereafter referred to as venous sensor, is provided to measure the pressure on the venous side of the dialyser 6. In the illustrated example, the pressure sensor 4c measures the pressure in the venous drip chamber. Both the arterial needle 1 and the venous needle 14 are connected to the patient by means of a blood vessel access. The blood vessel access may be of any suitable type, e.g. a fistula, a Scribner-shunt, a graft, etc. Depending on the type of blood vessel access, other types of access devices may be used instead of needles, e.g. catheters.

As discussed by way of introduction, it may be vital to monitor vital signs with respect to detection of the onset of rapid symptomatic drop in the subject's blood pressure. In many dialysis machines, one or more of said pressure detectors 4a-4c are not present. However, there will be at least one pressure sensor. The following description is focused on monitoring the pulse magnitude based on measurement data (a pressure signal) from pressure sensors in the extracorporeal circuit.

In FIG. 2, a control unit 23 is provided, i.a., to control the blood flow in the circuit 20 by controlling the revolution speed of the blood pump 3. The extracorporeal blood flow circuit 20 and the control unit 23 may form part of the dialysis machine 110. Although not shown or discussed further it is to be understood that the dialysis machine 110 performs many other functions, e.g. controlling the flow of dialysis fluid, controlling the temperature and composition of the dialysis fluid, etc.

In the example of FIG. 2, a data analysis part 29 of the monitoring device 120 is configured to obtain a pulse shape parameter $p_{PS}$, and process the pulse shape parameter $p_{PS}$ to represent the magnitude of the signal component, e.g., originating from the patient's heart in the pressure signal.

According to one embodiment, the data analysis part 29 is adapted to store received data, or data generated during processing, in a memory part 30. The memory part 30 is either included in the device 120, or associated thereto, e.g. via a cable or a wireless connection.

Fulfillment of a predetermined decision criterion, which fulfillment may be taken as an indication of an upcoming hypotension event, may bring the device 120 to activate an alarm A and/or output the alarm signal α, which may be followed by further actions to counter-act the occurrence of a hypotension event and/or reducing negative consequences to the subject where an hypotension event is unavoidable. Such actions may include:

i. Stopping or decreasing the rate of ultrafiltration (UFR),
ii. Optimizing fluid removal by regulating the (UFR), temporarily lowering or stopping the UFR in case of reached decision criterion,
iii. Increasing the conductivity in the dialysis fluid to increase refilling of the subject's blood circulation in order to increase the blood pressure and thus reduces the risk of hypotension,
iv. Supply a saline bolus to the blood line, i.e. a small yet concentrated amount of saline to increase refilling of the subject's blood circulation in order to increase the blood pressure and thus reduces the risk of hypotension,
v. Adjust the positioning of the subject to increase the blood volume to the head, e.g. by changing the subject's head and feet according to the so called "Trendelenburg position", for instance by controlling the structure of a bed or chair,
vi. Setting the dialysis monitor in bypass, i.e. temporarily stopping the dialysis process.

Noticeable is the function in ii), allowing maximal fluid to be drawn from the patient during a treatment, while yet avoiding the subject from suffering from hypotension.

In one embodiment, the monitoring device 120 is at least connected to receive measurement data from the arterial sensor 4a. The device 120 may also be connected to pressure sensors 4b and 4c, as well as any additional pressure sensors included in the extracorporeal blood flow circuit 20. As indicated in FIG. 2, the device 25 may also be connected to the control unit 23. Alternatively or additionally, the unit 25 may be connected to a measurement device 26 for indicating the frequency and phase of the blood pump 3. The device 25 is tethered or wirelessly connected to a local or remote device 27 for generating an audible/visual/tactile alarm or warning signal. The monitoring device 120 and/or the alarm device 27 may alternatively be incorporated as part of the dialysis machine 110.

In FIG. 2, the monitoring device 25 comprises a data acquisition part 28 for preprocessing the incoming measurement data, e.g. including an A/D converter with a required minimum sampling rate and resolution, one or more signal amplifiers, one or more filters to remove undesired components of the incoming signal(s), such as offset, high frequency noise and supply voltage disturbances.

In the examples given herein, the data acquisition part 28 comprises a DAQ card USB-6210 from National Instruments with a sampling rate of 1 kHz and resolution of 16 bits, an operation amplifying circuit AD620 from Analog Devices, a high-pass filter with a cut-off frequency of 0.03 Hz (i.a., for removal of signal offset) together with a low-pass filter with a cut-off frequency of 402 Hz (i.a., for removal of high frequency noise). To obtain a short convergence time, a low-order filter is used for the high-pass filter. Furthermore, the data acquisition part 28 may include an additional fixed bandpass filter with upper and lower cut-off frequencies of 0.5 Hz and 2.7 Hz, respectively, which corresponds to heart pulse rates between 30 and 160 beats per minute. This filter may be used to suppress disturbances outside the frequency interval of interest. Alternatively, the upper and lower cut-off frequencies may be set to filter the breathing signal, or even the autonomous regulation which also may be used for detection of hypotension in accordance with the present invention.

Figure 3A:
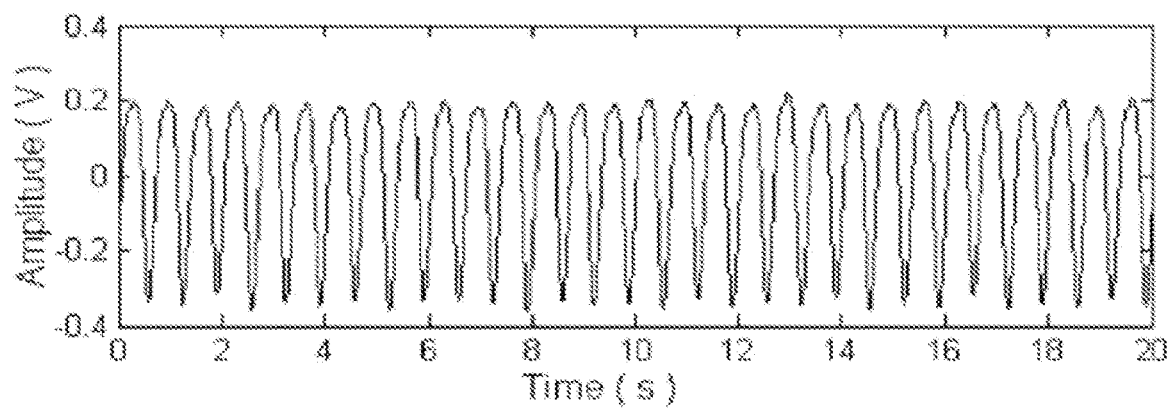
FIG. 3A is a plot in the time domain of a venous pressure signal containing both pump frequency components and a heart signal.
Figure 3B:
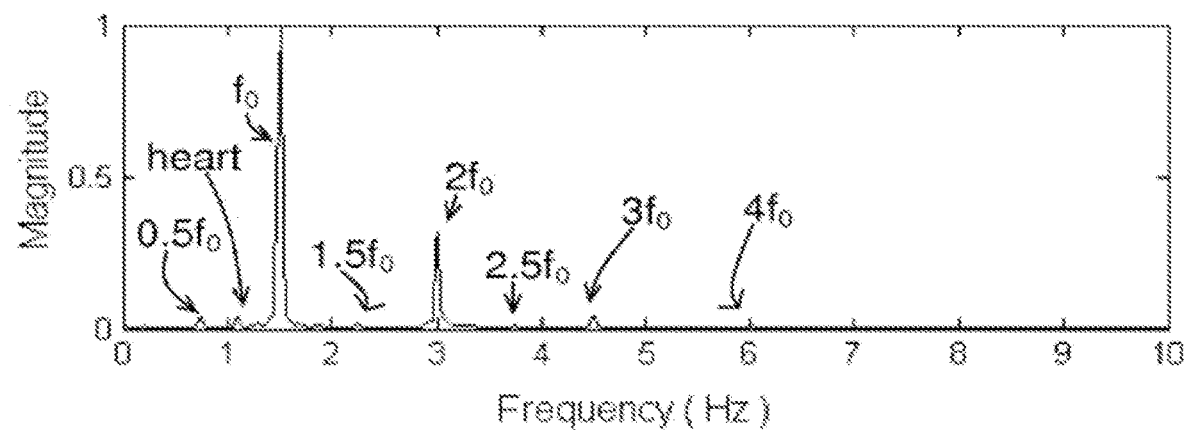
FIG. 3B is a plot of the corresponding signal in the frequency domain.

After the pre-processing in the data acquisition part 28, the resulting pressure signal is provided as input to the data analysis part 29, which executes the actual monitoring process. FIG. 3A shows an example of such a pre-processed pressure signal in the time domain, and FIG. 3B shows the corresponding power spectrum, i.e. the pressure signal in the frequency domain. The power spectrum reveals that the detected pressure signal contains a number of different frequency components emanating from the blood pump 3. In the illustrated example, there is a frequency component at the base frequency ($f_0$) of the blood pump (at 1.5 Hz in this example), as well as its harmonics $2f_0$, $3f_0$ and $4f_0$. The base frequency, also denoted pumping frequency in the following, is the frequency of the pump strokes that generate pressure waves in the extracorporeal blood flow circuit. For example, in a peristaltic pump of the type shown in FIG. 2, two pump strokes are generated for each full revolution of the rotor. FIG. 3B also indicates the presence of a frequency component at half the pumping frequency ($0.5f_0$) and harmonics thereof, in this example at least $f_0$, $1.5f_0$, $2f_0$ and $2.5f_0$. FIG. 3B also shows a heart signal (at 1.1 Hz) which in this example is approximately 40 times weaker than the blood pump signal at the base frequency $f_0$.

Figure 4A:
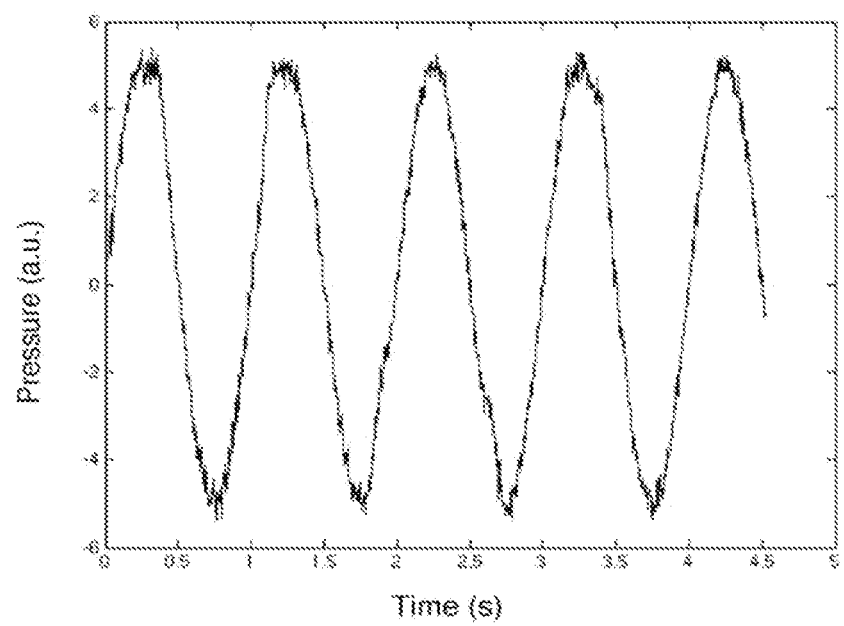
FIG. 4A is a plot of a pressure signal as a function of time.
Figure 4B:
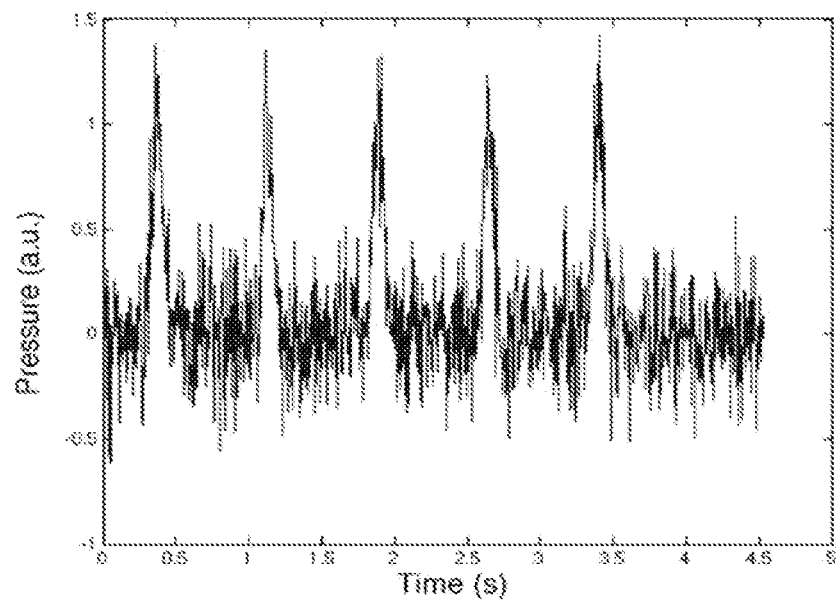
FIG. 4B is a plot of the pressure signal after filtering.

As will be described in further detail below (Section IV), the data analysis part 29 may process the pressure signal to obtain a "monitoring signal". The monitoring signal is obtained by essentially eliminating artifacts originating from pulse generators in the extracorporeal circuit 20, and possibly by isolating patient pulses that originate from a relevant pulse generator in the patient P among pulses that originate from other pulse generators in the patient P. FIG. 4A illustrates a pre-processed pressure signal obtained from the data acquisition part 28, and FIG. 4B illustrates a monitoring signal which contains pressure pulses (heart pulses) originating from pressure waves generated by heart beats in the patient P.

II. DESCRIPTION OF EMBODIMENTS OF THE INVENTION

Without being limited thereto, embodiments of the invention are mainly concerned with the prediction of "symptomatic intradialytic hypotension", in particular rapidly occurring such events.

Methods which measure capillary pulse changes reflect a combined effect from contraction of arterioles and change to the cardiac output. The methods disclosed with the present invention based on venous and artery pressure pulse measurements mainly reflect changes to the cardiac output.

In the following embodiments, the prediction is determined based on a decision criterion which is given relative to a reference measure, which may be given by a pulse magnitude measure and/or a statistical dispersion measure. The reference measure may be predetermined, or retrieved from a memory storing data from a previous treatment session or data from an earlier time point in the current treatment session.

Magnitude Embodiment

According to one embodiment, the monitoring device 120 is adapted to predict rapid symptomatic blood pressure decrease in the subject P based on an initial pulse magnitude measure PM1 calculated from one or more pulse shape parameters $p_{PS}$ obtained from the monitoring signal during an initial phase e.g. of the blood treatment when the subject is still relatively unaffected by the treatment.

Figure 5A:
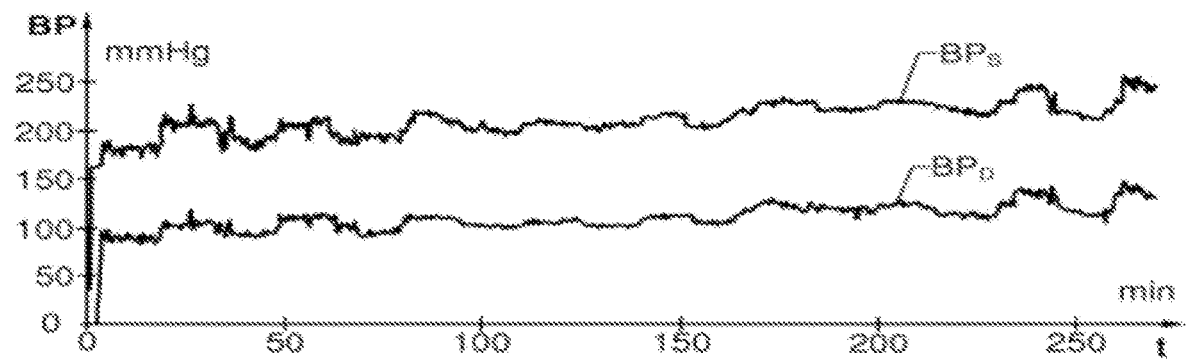
FIG. 5A is a graph illustrating an example of a first subject's blood pressure variation during a blood treatment process.
Figure 5B:
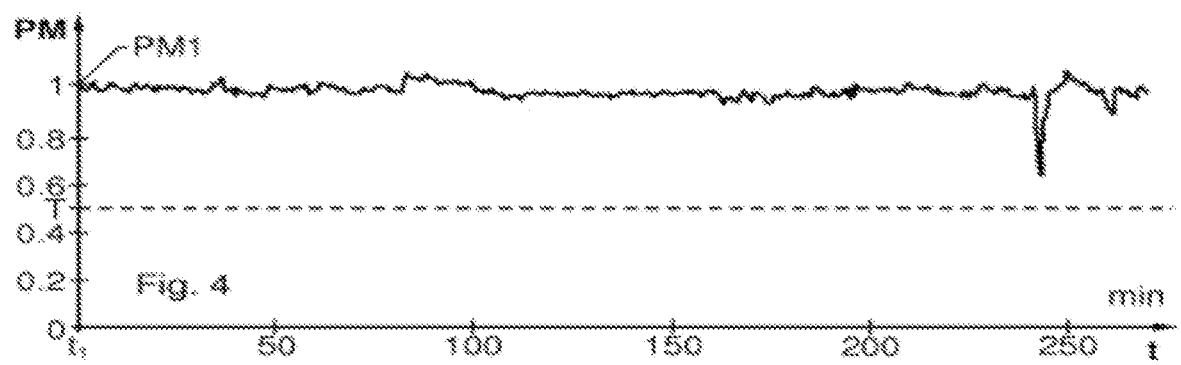
FIG. 5B is a graph illustrating how a pulse magnitude measure of the first subject varies over time.

FIG. 5B shows a graph, which illustrates the initial pulse magnitude measure PM1 in respect of a first subject being exposed to an extracorporeal blood treatment, as well as subsequently calculated pulse magnitude measures PM. Preferably, the initial pulse magnitude measure PM1 is not only derived from a singular pulse shape parameter $p_{PS}$, but is rather based on an average of a number of such parameters registered during an initial measurement period. The graph in FIG. 5B represents time t in minutes along the horizontal axis, and the pulse magnitude measure PM along the vertical axis.

According to embodiments of the invention, the data analysis part 29 (FIG. 2) may determine the pulse magnitude measure PM via any one of number of different strategies.

In one alternative, the pulse magnitude measure PM is given by the difference between a maximum and a minimum value of the pulse shape parameter $p_{PS}$, where the pulse shape parameter $p_{PS}$ is selected to contain at least one patient pulse. Below, this measure is also denoted "peak-to-peak measure". If the pulse shape parameter $p_{PS}$ contains plural patient pulses, the pulse magnitude measure PM may alternatively be given by an average of the different peak-to-peak measures for the patient pulses in the pulse shape parameter $p_{PS}$.

In another alternative, the pulse magnitude measure PM is given by an integral of the signal values in the pulse shape parameter $p_{PS}$, optionally with respect to a base line, e.g. given by a minimum value in the pulse shape parameter $p_{PS}$. The integral may be given by a sum of values, a sum of absolute values, or any equivalent function.

In yet another alternative, the pulse magnitude measure PM is given by the envelope of the pulse shape parameter $p_{PS}$, e.g. obtained by calculating the so-called Hilbert transform of the pulse shape parameter $p_{PS}$.

In another alternative, the pulse magnitude measure PM is given by a power or energy measure such as root mean square (RMS) of the pulse shape parameter $p_{PS}$, or any equivalent function. The use of RMS may require a prior calibration of the signal values to a zero average.

In yet another alternative, the pulse magnitude measure PM is obtained by a frequency analysis of the pulse shape parameter $p_{PS}$, e.g. as an intensity of one or more frequency components in an energy spectrum obtained by Fourier analysis of the pulse shape parameter $p_{PS}$.

FIG. 5A is a graph illustrating the first subject's systolic and diastolic blood pressure variations $BP_S$ and $BP_D$ respectively in mmHg during the treatment. It should be understood that the blood pressure data in FIG. 5A has been obtained by a dedicated instrument connected to the subject for the sole purpose of demonstrating that the pulse magnitude measure is useful in predicting a rapid symptomatic blood pressure decrease in the subject. The blood pressure BP varies throughout the treatment. However, as may be seen in FIG. 5A, no hypotension occurs. Apart from a dip around 245 minutes into the treatment, the pulse magnitude measure PM also remains relatively stable (FIG. 5B).

During a measurement period subsequent to the first instance $t_1$ (i.e. here from t=0 and onwards), the data analysis part 29 is adapted to calculate a respective pulse magnitude measure PM based on each of a number of obtained pulse shape parameters $p_{PS}$. This typically means that a time sequence of pulse magnitude measures PM are generated for a time sequence of pulse shape parameters $p_{PS}$. For each pulse magnitude measure PM in the measurement period, the data analysis part 29 is further adapted to investigate whether or not the measure PM fulfils a decision criterion relative to the initial pulse magnitude measure PM1. If such a decision criterion is found to be fulfilled, the data analysis part 29 is adapted to generate an alarm triggering signal α. The alarm triggering signal α, in turn, is presumed to cause an alarm A to be activated in the alarm device 27. The pulse magnitude measure PM and the decision criterion will be discussed in detail below with reference to FIGS. 6A, 6B, 7A, 7B and 8.

Figure 6A:
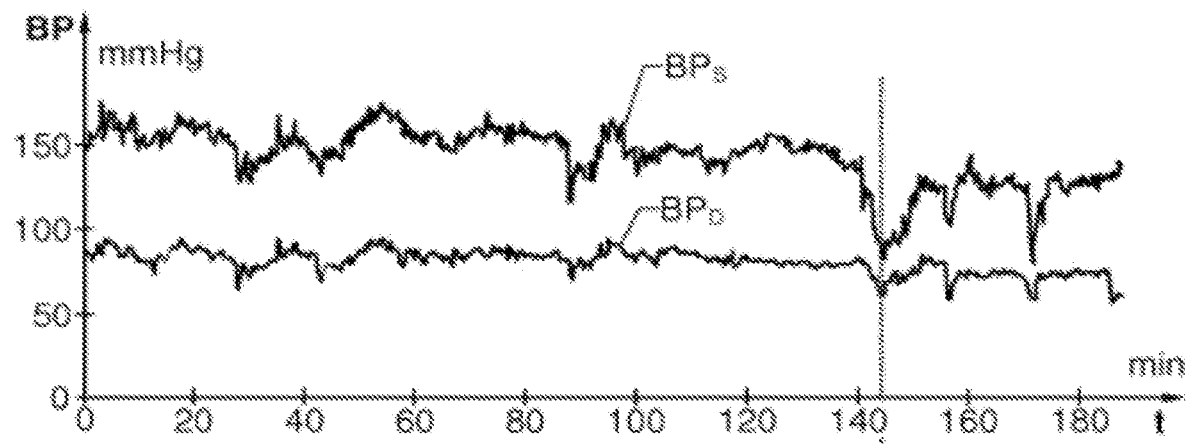
FIG. 6A is a graph illustrating an example of a second subject's blood pressure variation during a blood treatment process.

Turning now to FIG. 6A, we see a diagram with a graph exemplifying how the systolic blood pressure $BP_S$ and the diastolic blood pressure $BP_D$ in mmHg of a second subject varies during an extracorporeal blood treatment. At a point in time $t_h$ around 145 minutes into the treatment, the subject suffers from acute symptomatic hypotension. This event is preceded by a rapid BP decrease in both the systolic $BP_S$ and diastolic $BP_D$ blood pressures.

Figure 6B:
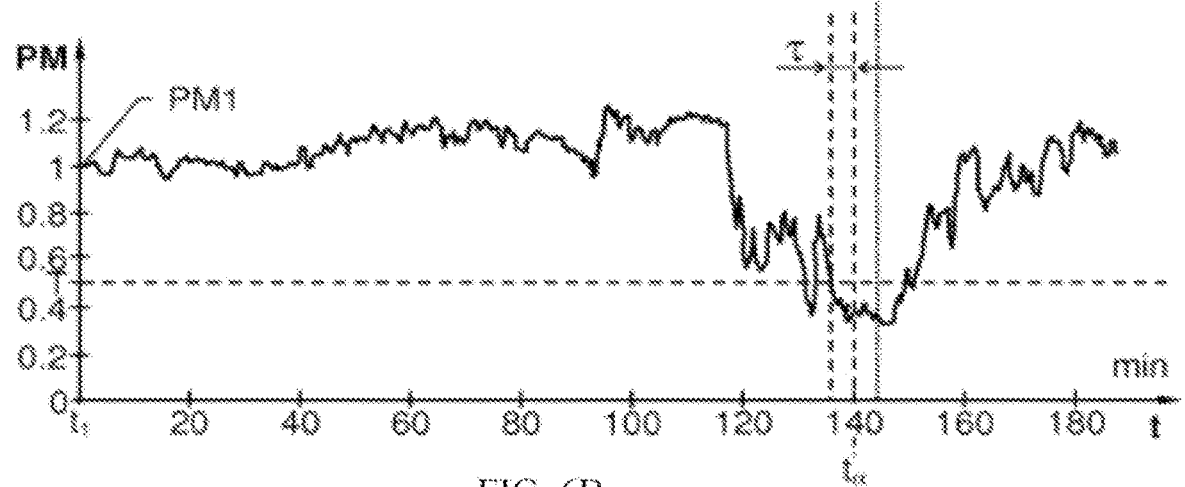
FIG. 6B is a graph illustrating how a pulse magnitude measure of the second subject varies over time.

Referring further to FIG. 6B we will now explain how the proposed pulse magnitude measure PM and a reference measure or threshold value T are calculated according to embodiments of the invention, and how evaluation of these measures is used to predict the hypotension event.

The data analysis part 29 (FIG. 2) is adapted to investigate whether a decision criterion is fulfilled with respect to the pulse shape parameters $p_{PS}$ obtained during the measurement period. In this example, the measurement period starts at t=0, and the period continues throughout the interval covered by the diagrams of FIGS. 6A and 6B.

The data analysis part 29 may calculate the threshold value T as follows. First, the initial pulse magnitude measure PM1 derived at $t_1$ (i.e. here t=0) is normalized. In this example PM1=1, however technically, any other reference is conceivable. Then the normalized value is divided by a predefined denominator, which may be any number between 1.2 and 5, e.g. 2. As a result, the threshold value T is obtained. Consequently, given that the predefined denominator is 2, T becomes 0.5 as illustrated in FIG. 6B by a dashed line. In the measurement period after t1, the data analysis part 29 calculates a normalized pulse magnitude measure PM for each received pulse shape parameter $p_{PS}$ by dividing an original magnitude measure with the normalized initial pulse magnitude measure PM1 (which is derived from the pulse shape parameter $p_{PS}$ received at the first instance $t_1$). Hence, a pulse magnitude measure PM representing a larger pulse magnitude than that of the pulse shape parameter $p_{PS}$ received at the first instance $t_1$ results in a pulse magnitude measure PM>1, and conversely, a pulse magnitude measure PM representing a smaller pulse magnitude than that of the pulse shape parameter $p_{PS}$ received at the first instance $t_1$ results in a pulse magnitude measure PM<1.

When the pulse magnitude measure PM has been derived, the data analysis part 29 regards the above-mentioned decision criterion to be fulfilled if:

a) an examined pulse magnitude measure PM of a given pulse shape parameter is below the threshold value T; and
b) a predetermined amount of the pulse magnitude measures PM of the pulse shape parameters $p_{PS}$ received within a test period τ after the given pulse shape parameter are below the threshold value T.

According to one embodiment of the invention, the predetermined amount is a value representing approximately 50% to approximately 100% of the pulse magnitude measures PM of the pulse shape parameters $p_{PS}$ received within the test period τ. The predetermined amount may represent all the pulse magnitude measures PM of the pulse shape parameters $p_{PS}$ received within the test period τ. Nevertheless, to avoid interruption by singular pulse magnitude measures PM above the threshold value T, it may be advantageous to assign a predetermined amount equivalent to less than 100%. Alternatively, a secondary threshold value may be assigned somewhat above the threshold value T, and the data analysis part 29 may employ a hysteresis algorithm, such that once the pulse magnitude measures PM has fallen below the threshold value T, the decision criterion is deemed fulfilled if, at expiry of the test period τ, the pulse magnitude measures PM has not exceeded the secondary threshold value.

In the example illustrated in FIG. 6B, the pulse magnitude measure PM for the first time falls below the threshold value T around t=128 minutes. Here, we assume that the above-mentioned predetermined amount is 100%, and that the test period τ is 5 minutes long. Hence, the test period τ ends around t=133 minutes. At this point in time, however, the pulse magnitude measure PM again exceeds the threshold value T. Therefore, no alarm triggering signal will be generated by the data analysis part 29.

Around t=135 minutes, the pulse magnitude measure PM returns to a level below the threshold value T, and this time the pulse magnitude measure PM remains below the threshold value T for period exceeding the test period τ (here 5 minutes). Consequently, at the end of the test period τ (i.e. at approximately t=140 minutes), the data analysis part 29 generates the alarm triggering signal α. It is then around 5 minutes left until t=$t_h$ when hypotension occurred. Thus, aided by the alarm triggering signal α, it had been possible to perform appropriate, manual and/or automatic, hypotension inhibiting actions in due time. It is further advantageous if the data analysis part 29 is adapted to generate an attention signal (e.g. causing a yellow lamp on the unit to be lit up) whenever the pulse magnitude measure PM is below the threshold value T. Thus, any supervising staff may obtain an earliest possible indication of that acute symptomatic hypotension may be forthcoming, and that therefore the subject needs extra attention. If, at the end of the pulse magnitude measure PM rises above the threshold value T without the decision criterion having been fulfilled, the attention signal is deactivated.

Of course, in embodiments of the invention, a test period τ of length other than five minutes is likewise conceivable. In fact, the test period τ may represent any interval selected from a range extending from approximately one minute to approximately fifteen minutes. The length of the test period τ is a design parameter that is selected to attain a desired balance between robustness and reliability. Preferably, the choice of the test period τ is made conjoint with the predefined denominator above. Namely, for a given balance between early hypotension warning and false alarms, a relatively large denominator requires a comparatively short test period, and vice versa.

Moreover, if in the example of FIG. 6B, the predetermined amount of pulse magnitude measure PM below the threshold value T required to fulfil the decision criterion had been selected to a value less than 100%, say 60%, the alarm triggering signal α would have been generated already at expiry of the first test period τ (i.e. around t=133 minutes).

Analogous to FIGS. 6A and 6B, FIGS. 7A and 7B are graphs exemplifying a third subject's blood pressure changes during an extracorporeal blood treatment and a corresponding pulse magnitude measure change, respectively.

In this example, the subject suffers from two acute symptomatic hypotension events at t=$t_{h1}$ (around 155 minutes into the treatment) and at t=$t_{h2}$ (around 178 minutes into the treatment) respectively. To facilitate comparison with the previous examples, we have also here chosen to normalize the initial pulse magnitude measure PM1'' derived at $t_1$ (t=0) to 1, selected a threshold value T=0.5 (i.e. the predefined denominator is 2), and set the length of the test period τ to five minutes. Furthermore, we regard the decision criterion as fulfilled if all pulse magnitude measures PM of the pulse shape parameters $p_{PS}$ received within the test period τ fall below the threshold value T.

Figure 7A:
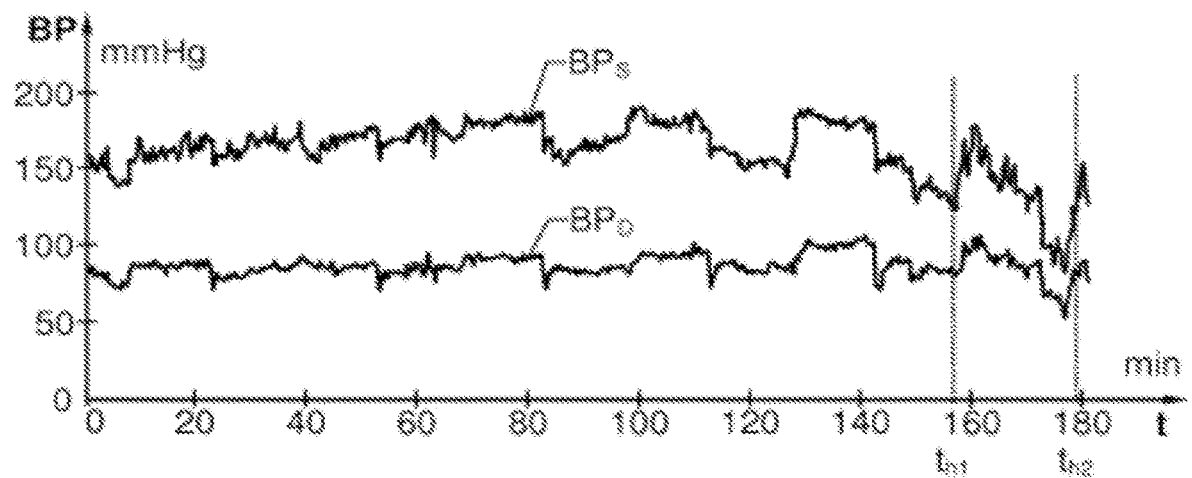
FIG. 7A is a graph illustrating an example of a third subject's blood pressure variation during a blood treatment process.
Figure 7B:
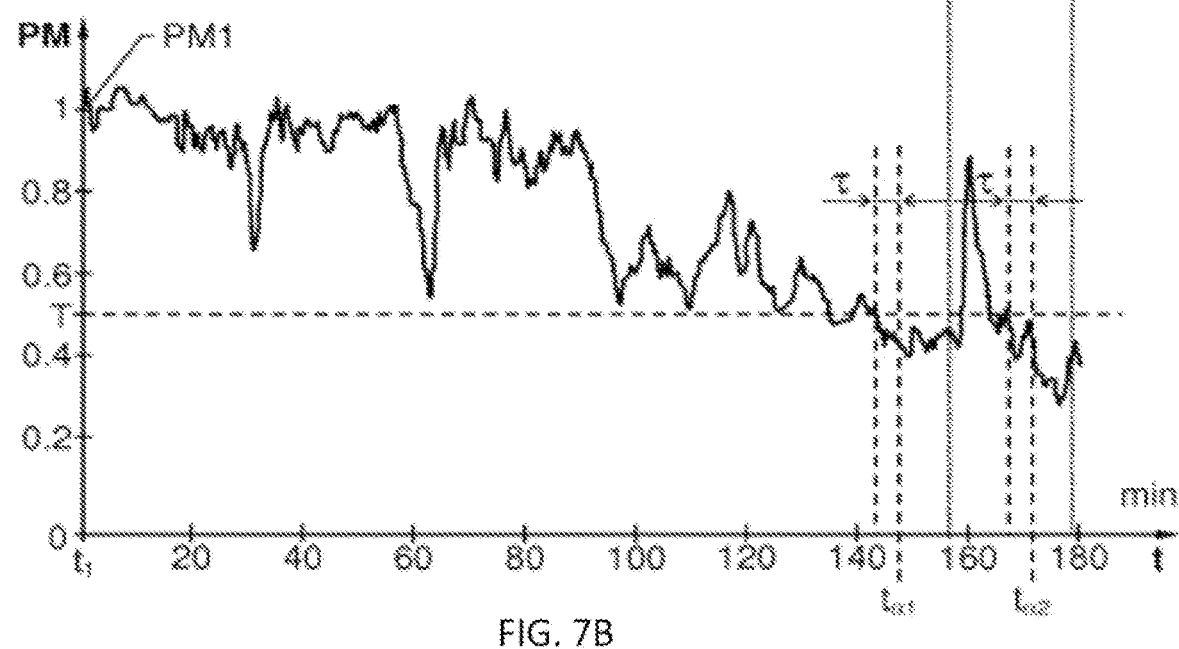
FIG. 7B is a graph illustrating how a pulse magnitude measure of the third subject varies over time.

As is apparent from the diagram in FIG. 7B, given these parameter values, the data analysis part 29 will generate the alarm triggering signal α at t=$t_{α1}$ (around 145 minutes into the treatment) and at t=$t_{α2}$ (around 171 minutes into the treatment) respectively. Thus approximately seven to ten minutes advance indications of the upcoming hypotension events are provided.

Returning briefly to FIG. 5B, we see that the pulse magnitude measure PM here never falls below the threshold value T (here 0.5). Thus, in this case, the data analysis part 29 will not generate any alarm triggering signal α.

According to other embodiments of the invention, the arrangement 100 of FIG. 1 may further include an auxiliary recording unit 130 adapted to repeatedly register a bio-impedance parameter $p_{BI}$ that represents a degree of contraction of the subject's P capillary blood vessels. In this embodiment, the data analysis part 29 of FIG. 2 is further adapted to obtain this bio-impedance parameter $p_{BI}$, and investigate whether or not the parameter $p_{BI}$ fulfils an auxiliary alarm criterion. If this criterion is found to be fulfilled, the data analysis part 29 is adapted to generate the alarm triggering signal α. Hence, the performance and reliability of the arrangement 100 of FIG. 1 is improved. To further improve the usability of the arrangement 100, it is preferable if the auxiliary recording means 130 is adapted to determine a bio-impedance parameter being essentially unrelated to the pressure in the blood vessels. Thus, the auxiliary recording means 130 may register an absolute body temperature, variations in the body temperature and/or an amount of sweat on the subject P, thoracic bioimpedance analysis and the processing unit may be adapted to test the auxiliary alarm criterion against one or more of these parameters.

An example of a method of predicting rapid symptomatic blood pressure decrease in a subject according to the invention will now be described below with reference to the flow chart in FIG. 8.

A first step 810 investigates whether or not a pulse shape parameter in respect of the extracorporeal circuit has been received. If no such parameter has been received, the procedure loops back and stays in step 810. If, however, a pulse shape parameter is received, a step 820 follows, which calculates an initial pulse magnitude measure based on a pulse shape parameter received at a first instance. It is here presumed that the pulse shape parameter has been registered by means of a pressure sensor wherein the pulse shape parameter is determined based on pressure variations which reflect pressure variations in at least one blood vessel of the subject.

A following step 830 stores the initial pulse magnitude measure in a memory (cf. memory part 30 in FIG. 2). Thereafter, a measurement period follows during which a step 840 calculates a respective pulse magnitude measure based on each received pulse shape parameter. Moreover, for each pulse magnitude measure in the measurement period, an evaluation step 850 subsequent to step 840 investigates whether or not the pulse magnitude measure fulfils a decision criterion relative to the initial pulse magnitude measure. If the decision criterion is found not to be fulfilled, and provided that the measurement period still is active, the procedure loops back to step 840.

However, if it is found in the evaluation step 850 that the decision criterion is fulfilled, a step 860 follows, which causes an alarm triggering signal to be generated. Thereafter, the procedure may either end, or loop back to the step 840 (provided that the measurement period still is active). The measurement period may be inactivated in response to a manual intervention, such as depressing a reset button.

Depending on implementation, steps 820 and 830 may be omitted, and step 840 may operate without normalization. It is also conceivable, in all embodiments, that the decision criterion (in step 850) uses a predefined threshold or reference measure instead of a threshold determined based on the initial pulse magnitude measure (PM1). It is also believed that the pulse magnitude measure itself may contain information that may be used for predicting an upcoming hypotension event. The predefined threshold may, e.g., be given as an absolute or relative pulse magnitude value.

All of the process steps, as well as any sub-sequence of steps, described with reference to the FIG. 8 above may be executed by the data analysis part 29, which may be implemented by a programmed computer apparatus. Moreover, although embodiments of the invention may comprise a computer apparatus and processes performed in the computer apparatus, embodiments of the invention also extends to computer programs, particularly computer programs on or in a carrier, adapted for putting the invention into practice. The program may be in the form of source code; object code, a code intermediate source and object code such as in partially compiled form, or in any other form suitable for use in the implementation of the process according to the invention. The carrier may be any entity or device capable of carrying the program. For example, the carrier may comprise a storage medium, such as a Flash memory, a ROM (Read Only Memory), for example a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

It is also conceivable that some or all process steps are fully or partially implemented by dedicated hardware, such as an FPGA, an ASIC, or an assembly of discrete electronic components (resistors, capacitors, operational amplifier, transistors, filters, etc), as is well-known in the art.

Additionally, it may be advantageous to use timing information to determine which pulses that are of interest, determining techniques which also will be described in more detail below in Section III.

Figure 10A:
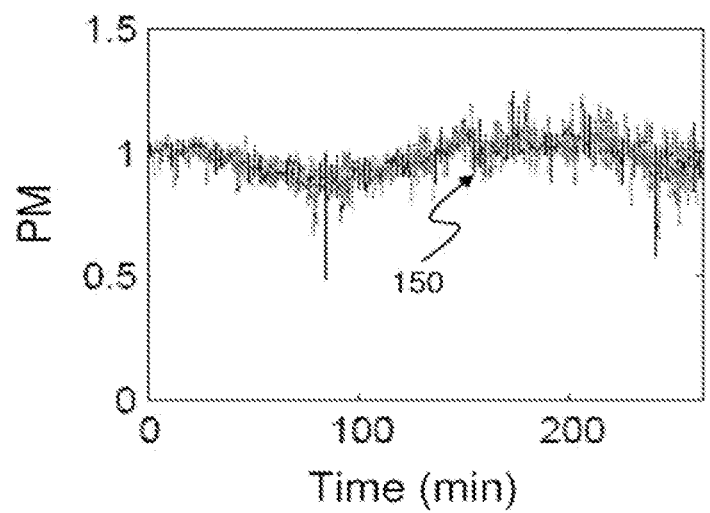
FIGS. 10A-10C are plots of various measures obtained during a treatment with no hypotension event.
Figure 10B:
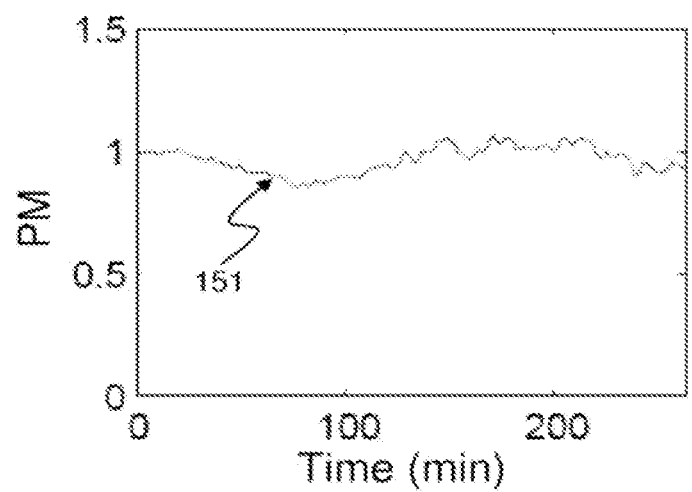

FIGS. 10A-10B are graphs that illustrate pulse magnitude measures PM obtained in respect of a first subject undergoing an extracorporeal blood treatment with no occurrence of hypotension. In FIG. 10A, the graph comprises a curve 150 formed by a sequence of pulse magnitude measures PM (peak-to-peak measures) which are calculated for a sequence of non-overlapping pulse shape parameters $p_{PS}$, where the time window of each pulse shape parameter $p_{PS}$ is selected such that it includes one patient pulse. FIG. 10B includes a curve 151 which corresponds to the curve 150, but where the time window of each pulse shape parameter $p_{PS}$ is selected to include a plurality of patient pulses. Thereby, curve 151 is represented as a low-pass filtered version of curve 150. The curve 151 may be seen to illustrate a local "DC" component of a "pulse magnitude signal" derived from the pressure signal S, whereas the curve 150 represent a superposition of the local "DC" component and a local "AC" component.

Figure 11A:
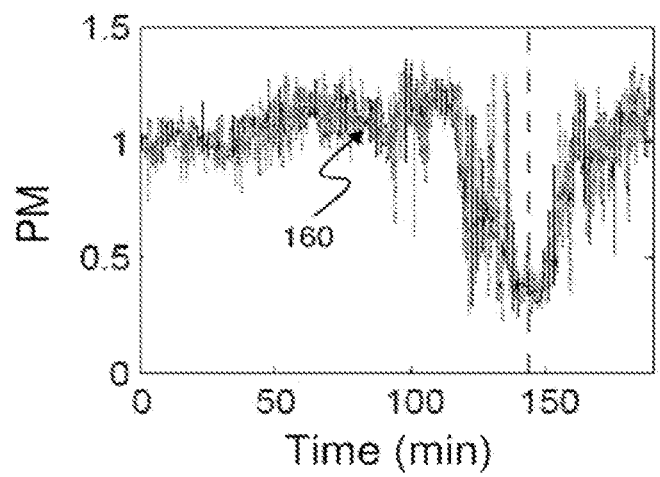
FIGS. 11A-11C are plots of various measures obtained during a treatment with an hypotension event.
Figure 11B:
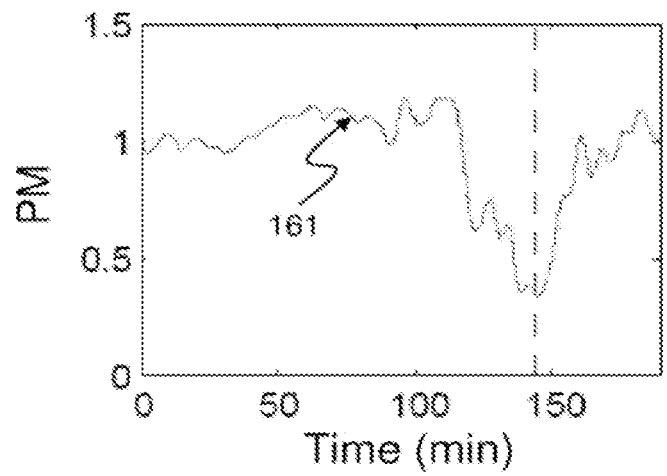

FIGS. 11A-11B are graphs that illustrate pulse magnitude measures PM obtained in respect of a second subject undergoing an extracorporeal blood treatment and suffering from acute symptomatic hypotension at a point in time ($t_{hyp}$) around 140 minutes into the treatment. The curves 160, 161 are obtained similarly to the curves 150, 151 in FIGS. 10A-10B. FIGS. 11A-11B clearly illustrate that the monitoring process, e.g. as exemplified in FIG. 8, may operate on the pulse magnitude measures PM in either of the curves 160, 161 to generate the alarm signal indicating a risk for rapid symptomatic blood pressure decrease. However, to reduce the occurrence of false alarms, it may be preferable to operate on the pulse magnitude measures in curve 161.

In an alternative embodiment (not shown), the pulse magnitude measures PM may be passed through a dedicated low-pass filter to reduce the variability before being subjected to the evaluation step 850.

It is also to be understood that similar curves 150, 151, 160, 161 may be obtained by calculating the pulse magnitude measures PM for overlapping pulse shape parameters $p_{PS}$ in the pressure signal S, e.g. for signal values within a sliding time window in the pressure signal S.

Experiments have been conducted to verify that the information obtained from a pressure sensor in the extracorporeal circuit in accordance with embodiments of the invention is equivalent or similar to information that may be obtained from a PPG (photoplethysmography) signal provided by a pulse oximetry instrument. As described in the background section, it is known from WO2007/141246 that a PPG signal may be processed for prediction of hypotension.

Figure 9:
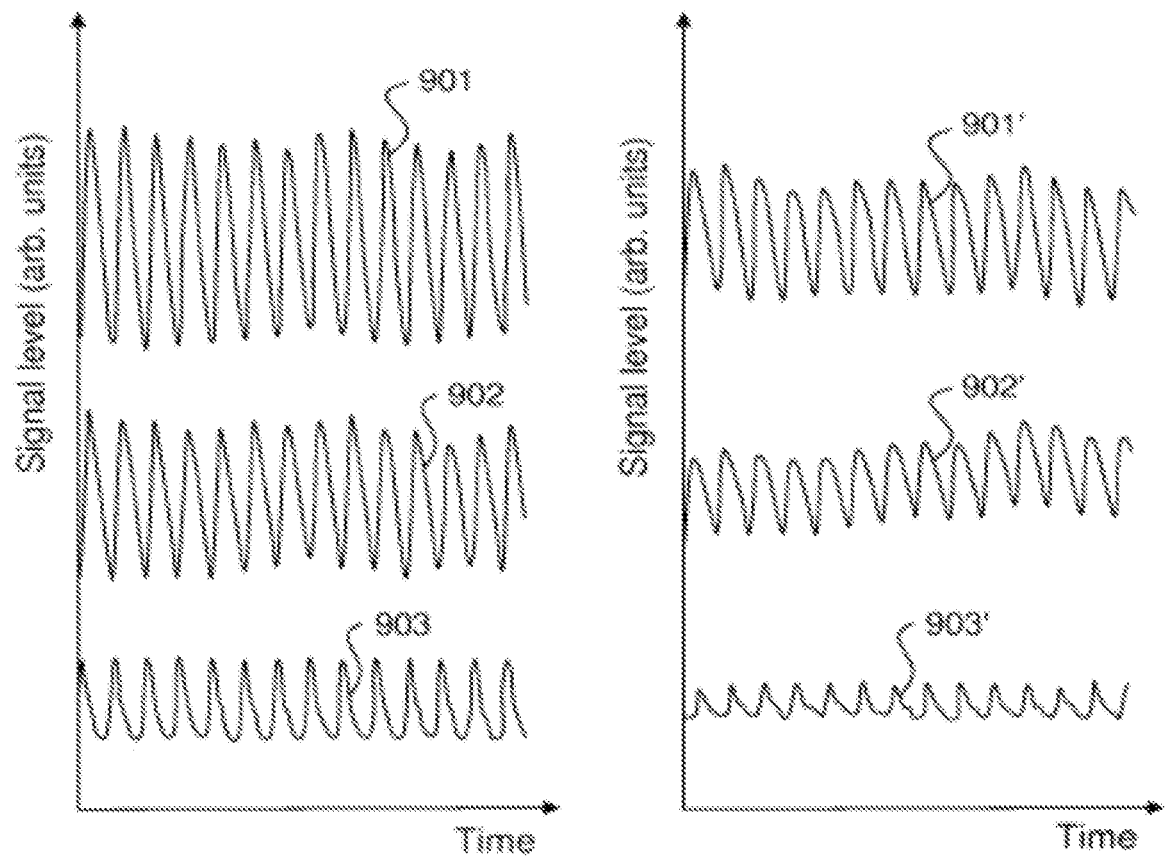
FIG. 9 is are graphs of heart pulse signals from pressure sensors in an extracorporeal circuit, and a PPG signal from a pulse oximeter connected to the subject, at start and end of a treatment session, respectively.

FIG. 9 is a graphical presentation of heart pulse signals 901, 901' that have been isolated in the pressure signal from an arterial pressure sensor (cf. 4c in FIG. 2), corresponding heart pulse signals from a venous pressure sensor (cf. 4a in FIG. 2), as well as a capillary pulse signal 903, 903' obtained from a pulse oximetry instrument. FIG. 9 indicates that the pulses in signals 901, 901' and 902, 902' respectively, are time-synchronized with the pulses in signal 903, 903'. Furthermore, the left-hand graph illustrates the signals 901, 902, 903 at the beginning of a dialysis treatment session, and the right-hand graph illustrates the signals 901', 902', 903' at the end of the same treatment session. It is seen that the magnitude of the capillary pulses decreases in response to fluid removal during a dialysis treatment, and that this behaviour is also represented in the heart pulses in the pressure signals.

Figure 12:
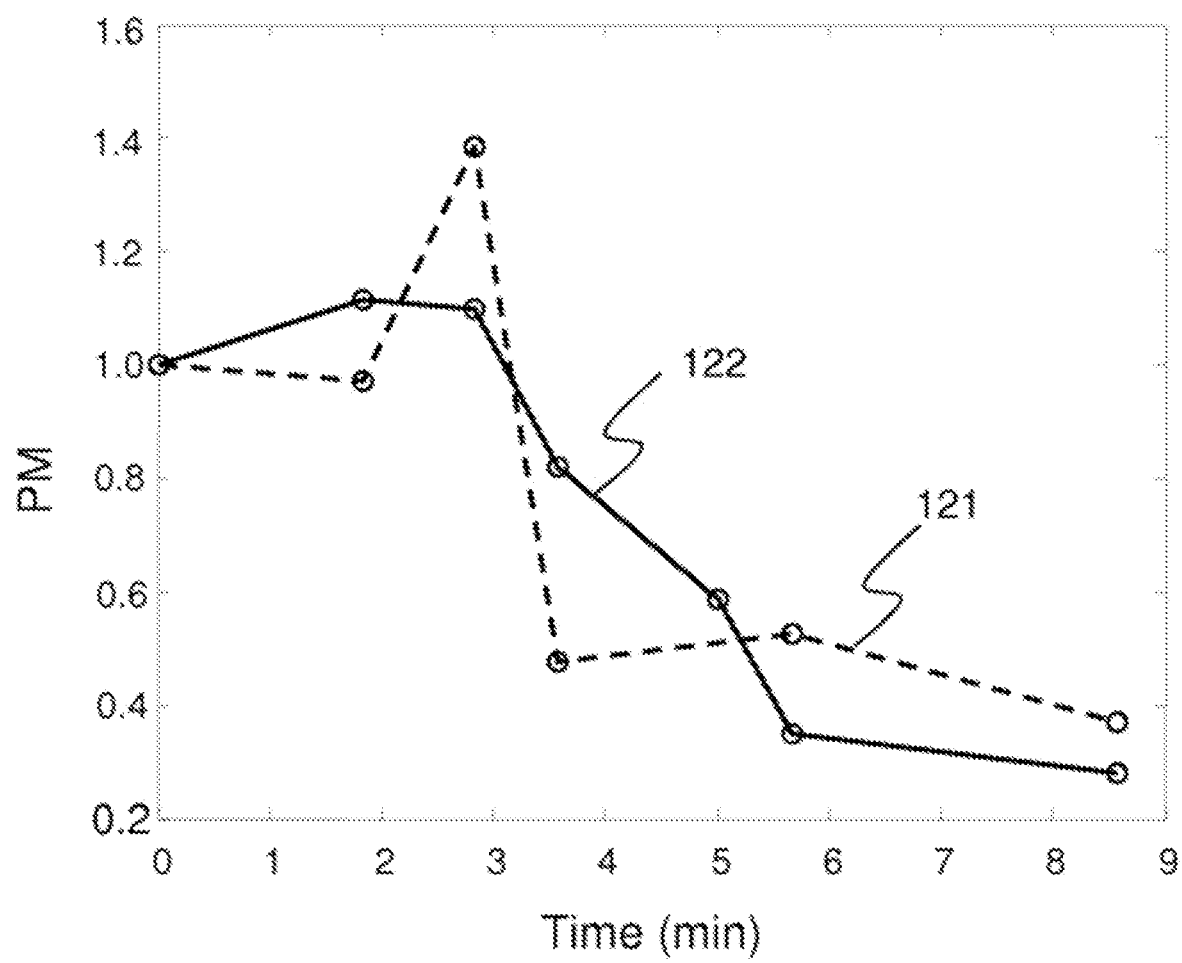
FIG. 12 is a graph of pulse magnitude measures obtained from a PPG signal and a pressure signal during a dialysis treatment session.

FIG. 12 is a graph of a time sequence of normalized pulse magnitude measures PM, obtained in a time period of 8 minutes during a dialysis treatment session. Curve 121 is obtained from a heart pulse signal (cf. 901, 902 in FIG. 9), and curve 122 is obtained from a PPG signal (cf. 903 in FIG. 9). It is seen that the pulse magnitude measures PM in curves 121 and 122 follow a similar path.

Statistical Dispersion Embodiment

It has surprisingly been found that the dispersion in the sequence of pulse magnitude measures obtained in accordance with the pulse magnitude embodiment may provide information for predicting an upcoming hypotension event.

The dispersion may be represented by any measure that represents a variability or spread of a sequence of values. Non-limiting examples of potentially useful statistical dispersion measures include standard deviation ($\sigma$), variance ($\sigma^2$), coefficient of variation ($\sigma/\mu$) and variance-to-mean ($\sigma^2/\mu$). Other examples include a sum of differences, e.g. given by $$\sum_{i=2}^{n} |x_i - x_{i-1}|, \text{ or } \sum_{i=1}^{n} \sum_{j=1}^{n} |x_i - x_j|,$$

or an energy measure, such as $$\sum_{i=1}^{n} x_i^2,$$

with n being the number of PM values in the sequence. Yet other examples include a measure based on a sum of absolute differences from an average value m, with the average value m being calculated for the PM values in the evaluation segment using any suitable function, such as arithmetic mean, geometric mean, median, etc. It is to be noted that all of the above suggested statistical dispersion measures also include normalized and/or weighted variants thereof.

Figure 8:
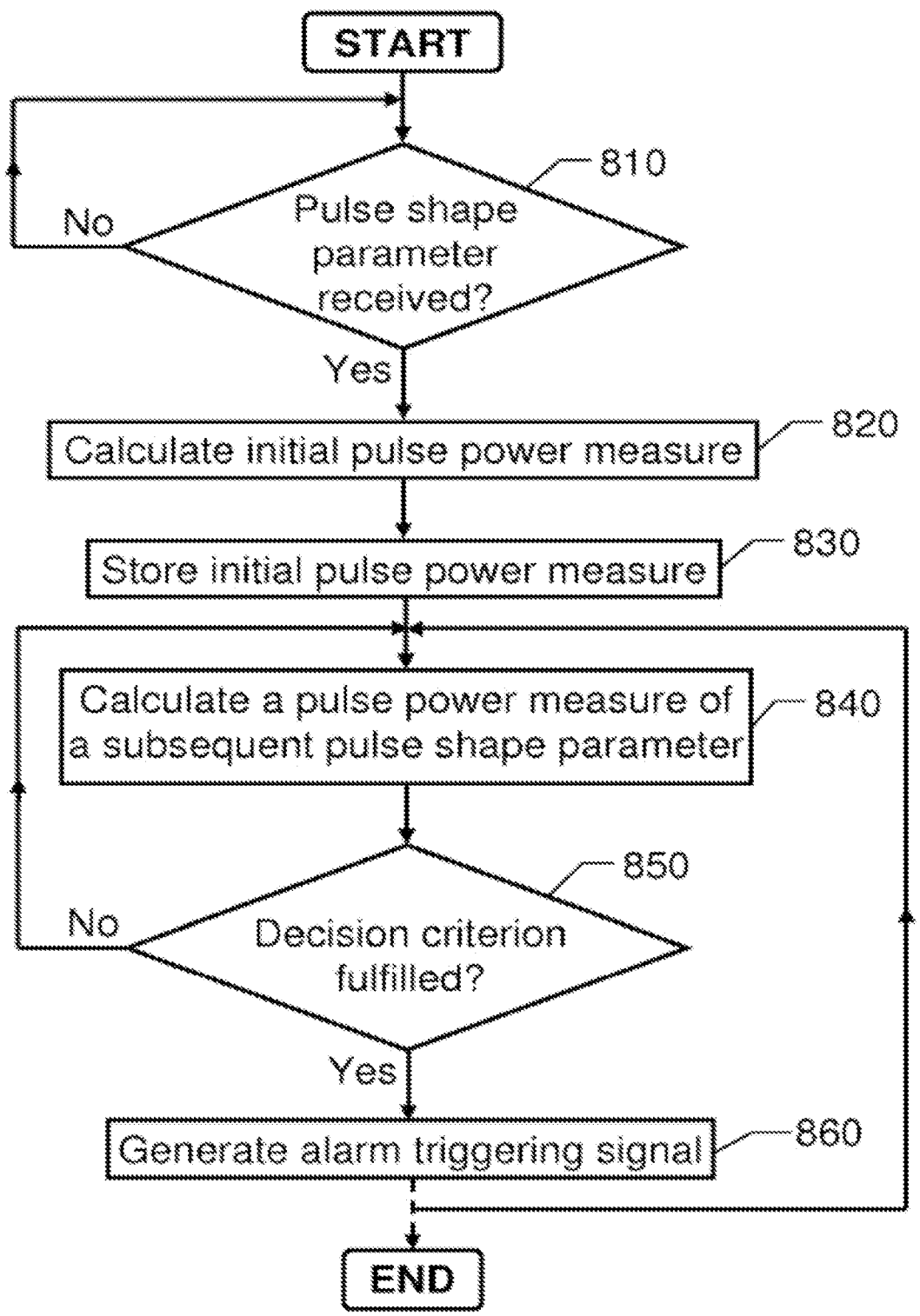
FIG. 8 is a flow chart which illustrates an embodiment of method of predicting rapid symptomatic blood pressure decrease.

For an embodiment of a method of predicting rapid symptomatic blood pressure decrease in a subject based on a statistical dispersion measure, reference may be made to the flow chart in FIG. 8. Thus, all steps 810-860 described in relation to FIG. 8 are equally applicable to the statistical dispersion embodiment.

In short, step 810 checks if a pulse shape parameter has been received, and if so, step 820 calculates an initial set of pulse magnitude measures PM1 based on a set of pulse shape parameters $p_{PS}$ received at a first instance, and calculates an initial dispersion measure SM1 based on the set of pulse magnitude measures PM. Here, it is understood that the initial dispersion measure SM1 represents the variability of the initial set of pulse magnitude measures PM1. Step 830 stores the initial dispersion measure SM1 in memory, wherein the measurement period is started by repeatedly executing steps 840 and 850. Step 840 calculates a respective pulse magnitude measure PM based on each received pulse shape parameter $p_{PS}$. Step 840 also calculates the dispersion measure SM for the thus-calculated pulse magnitude measure PM in combination with pulse magnitude measures PM calculated in previous iterations of steps 840 and 850. For example, the dispersion measure SM may be calculated for a set of the most recently calculated pulse magnitude measures PM. It is conceivable that step 840 is designed to calculate the dispersion measure SM only in certain iterations of steps 840 and 850. For example, every i:th iteration of step 840 may involve a calculation of the dispersion measure SM, whereas every iteration involves a calculation of the pulse magnitude measure PM. Moreover, for each dispersion measure SM in the measurement period, the evaluation step 850 investigates whether or not the dispersion measure SM fulfils a decision criterion relative to the initial dispersion measure SM1.

Furthermore, all embodiments, variants, alternatives, examples and implementations described in relation to the pulse magnitude embodiment are equally applicable to the dispersion embodiment, including the calculation of thresholds, the normalization of the initial measure, and examples of the decision criterion. However, in the dispersion embodiment, the decision criterion is typically fulfilled when the dispersion measure SM exceeds a threshold value T. Thus, in analogy with the examples given for the pulse magnitude embodiment, the threshold value T may be obtained by division with a predefined denominator in the approximate range of 0.2-0.8. In this context, a division by a denominator is equivalent to a multiplication by a predefined factor, e.g. in the range 1.2-5.

It has also been found that the dispersion measure itself may contain information that may be used for predicting an upcoming hypotension event. Thus, depending on implementation, steps 820 and 830 may be omitted, and step 840 may operate without normalization. It is also conceivable, in all embodiments, that the decision criterion (in step 850) uses a predefined threshold or reference measure instead of a threshold determined based on the initial statistical measure (SM1). The predefined threshold may, e.g., be given as an absolute or relative dispersion value.

Figure 10C:
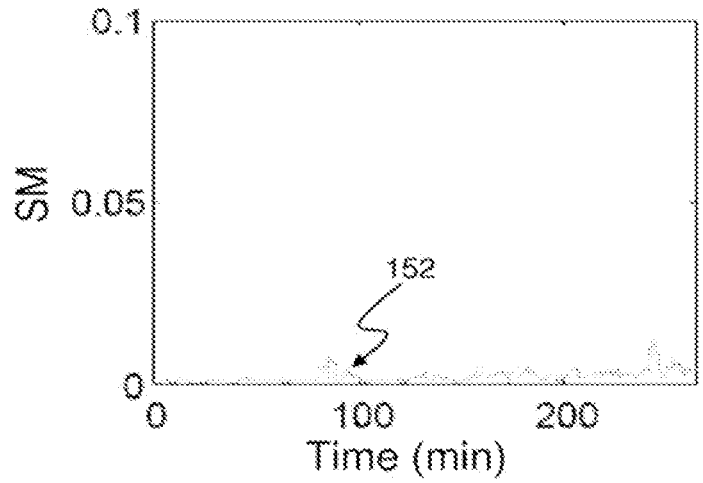
Figure 11C:
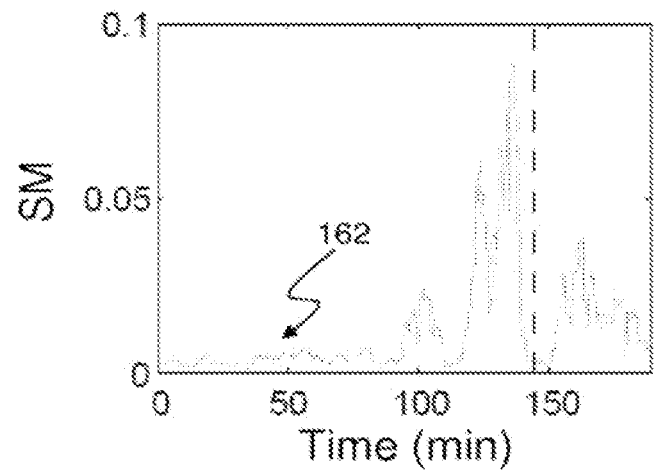

To further exemplify the use of the dispersion measure, the curve 152 in FIG. 10C is formed by variance measures SM calculated for the sequence of pulse magnitude measures PM in FIG. 10A. The curve 150 in FIG. 10A may be seen to include a longterm "DC" level component of the pulse magnitude measure PM, which is used for detection in the pulse magnitude embodiment, and a short-term "AC" component, which may be regarded as a pulse magnitude modulation. This modulation is represented by the variance measure in FIG. 10C. Similarly, the curve 162 in FIG. 11C is formed by values of the variance measure SM calculated for the sequence of pulse magnitude measures PM (curve 160) in FIG. 11A. Clearly, the variance measure SM may be evaluated to predict the acute symptomatic hypotension event.

The method for prediction of intradialytic hypotension according to this embodiment is to monitor the variance, or some other statistical measure, of the short-term pulse magnitude variation and to investigate whether or not it fulfils a decision criterion. As seen in FIGS. 10A, 10B, 11A, 11B and 11C, there is a significant increase in the variance prior to hypotension and a low variance in case of stable blood pressure, respectively.

The short-term variations in the pulse magnitude are mainly due to variations in cardiac output. Capillary vasoconstriction may also contribute to short-term variation in the pulse magnitude. It is hypothesised that the increase in variability of cardiac output and capillary vasoconstriction prior to a hypotension is caused by the increased variability in the pumping of blood from the heart and the autonomic regulation of vasoconstriction in response to the hemodynamic instability prior to a hypotension, respectively.

The short-term variations in the pulse magnitude may be more affected by cardiac output than by vasoconstriction, since the variations in cardiac output is on a beat-to-beat basis. The pulse magnitude measure (PM) of the first embodiment may be more affected by vasoconstriction. Thus, these two measures may be complimentary and/or supplementary to each other, and if combined the prediction performance may improve. The two measures may also be used to separate the two effects of cardiac output and vasoconstriction from each other or determining the sequence of the different events.

Of course, the short-term variations in pulse magnitude may be used as a sole marker for prediction of hypotension, thus neglecting the information from the pulse magnitude measure PM. Conversely, the pulse magnitude measure PM may be used as a sole marker for prediction of hypotension, thus neglecting the short-term variations in pulse magnitude.

In addition, the statistical dispersion measure SM and/or the pulse magnitude measure PM may be used in combination with other measures as well such as bio impedance or relative blood volume (BVS).

Combination of Embodiments

The methods of the above-described embodiments may extract different information from cardiac output and capillary vasoconstriction. Thus, by combining the pulse magnitude (PM) embodiment and the statistical dispersion (SM) embodiment it may be possible to separate the two effects from each other. In addition, there are differences in the changes of cardiac output and capillary vasoconstriction from patient to patient. In one patient, the autonomic regulation in order to prevent a hypotension may be more focused on regulations in cardiac output and in another patient it may be more focused on regulations in capillary vasoconstriction. Thus, the ability to predict a hypotension may be better reflected in the pulse magnitude (PM) measure in one patient and in the dispersion of the pulse magnitude measures (PM) in another patient. By combining the pulse magnitude embodiment and the dispersion embodiment, the prediction performance would probably improve on a large general dialysis population. In addition, the robustness to artifacts may also be improved if the two main embodiments are combined.

It may be noted that the length of the time window (i.e. the length of the pulse shape parameters $p_{PS}$), as well as the overlap (or non-overlap) of time windows, may differ between the pulse magnitude embodiment and the dispersion embodiment. Thus, when combining these embodiments, one set of pulse magnitude measures may be calculated in the pulse magnitude embodiment, and another set of pulse magnitude measures may be calculated in the dispersion embodiment. In both embodiments, the time window may be selected to include at least part of at least one pulse. However, it is presently believed that the maximum number of pulses in the time window may be any one of about 20, 15, 10, 5 and 2 in the dispersion embodiment, in order for the dispersion measure to reflect the variability in pulse magnitude.

The present invention relates to embodiments for prediction of hypotension during extra-corporeal circulation by only utilizing pressure signals of the existing pressure sensors of the extra-corporeal circuit, e.g. the venous and/or the arterial pressure. The underlying principle is that the pressure signals change in response to variation in the cardiac output and blood circulation of the peripheral parts. That is, the venous and arterial pressure varies with the blood access vessel pressure which changes with the cardiac output and the peripheral blood circulation.

By monitoring the relative magnitude or magnitude variation of the heart pulse pressure signal from start of a dialysis session and comparing the relative reduction of the magnitude to a threshold a hypotension alert/warning may be issued as the value goes below the threshold. Alternatively, an alert/warning is triggered as the magnitude variation of the heart pulse pressure signal exceeds another threshold. The process for extracting the heart pulse pressure signal is explained in detail further below.

Similarly to the heart pulses in a pressure signal, the magnitude of breathing pulses in a pressure signal may also be used for predicting hypotension in accordance with the method described above. In addition, the magnitude variation of the breathing pulse pressure signal may be used for the same purpose. Advantageously, the two signals may be monitored in parallel, increasing the reliance of the prediction.

One effect with the present invention, when combining the pulse magnitude embodiment with the dispersion embodiment is that it thus enables separation of the phenomena behind hypotension.

III. SIGNAL PROCESSING AND SIGNAL ANALYSIS

As noted in the foregoing, the monitoring process may operate on a monitoring signal which is generated based on measurement data from a pressure recording means in the extracorporeal circuit. Reverting to the example of FIG. 8, the monitoring process may involve calculating an evaluation parameter value (a pulse magnitude measure) based on the monitoring signal.

Different techniques for calculating an evaluation parameter value are further disclosed and exemplified in Appendix B, in which the monitoring signal is denoted a filtered measurement signal which include "second pulses" (heart pulses) originating from heart beats in a patient, and in which the measurement signal is subjected to a time domain analysis. In Appendix B, the "evaluation segment" may correspond to the above-mentioned pulse shape parameter $p_{PS}$, and the "evaluation parameter" may correspond to the pulse magnitude measure PM. Appendix B also suggests the use of "timing information", which is indicative of the timing of heart pulses in the measurement signal. Such timing information may be used in a monitoring process for predicting rapid symptomatic blood decrease, e.g. as shown in FIG. 8. The timing information may, e.g., be used for identifying and averaging heart pulses in the monitoring signal as part of the calculation of the pulse magnitude measure PM, for selecting a proper size and/or location of the pulse shape parameter $p_{PS}$ in the monitoring signal such that the pulse shape parameters $p_{PS}$ include a desired number of heart pulses, or for synchronizing monitoring signals, pulse shape parameters $p_{PS}$ or pulse magnitude measures PM obtained from more than one pressure sensor in the extracorporeal circuit.

Generally, all techniques disclosed in Appendix B with respect to the evaluation of heart pulses, including the use of timing information, are equally applicable to pulses originating from other physiological phenomena, such as breathing, autonomic regulation of body temperature, and autonomic regulation of blood pressure, or combinations thereof. In addition to Appendix B, reference is also made to Applicant's International patent publication WO2009/156174, entitled "Methods and Devices for Monitoring the Integrity of a Fluid Connection", which is incorporated herein in its entirety by this reference.

There are of course other techniques for calculating the evaluation parameter value, including other types of time domain analyses, as well as different types of frequency domain analyses, e.g. as indicated in the following.

Other factors, such as the medical history of the patient, e.g. heart status, blood pressure and heart rate may also be utilized for improving the performance of the monitoring.

Figure 13:
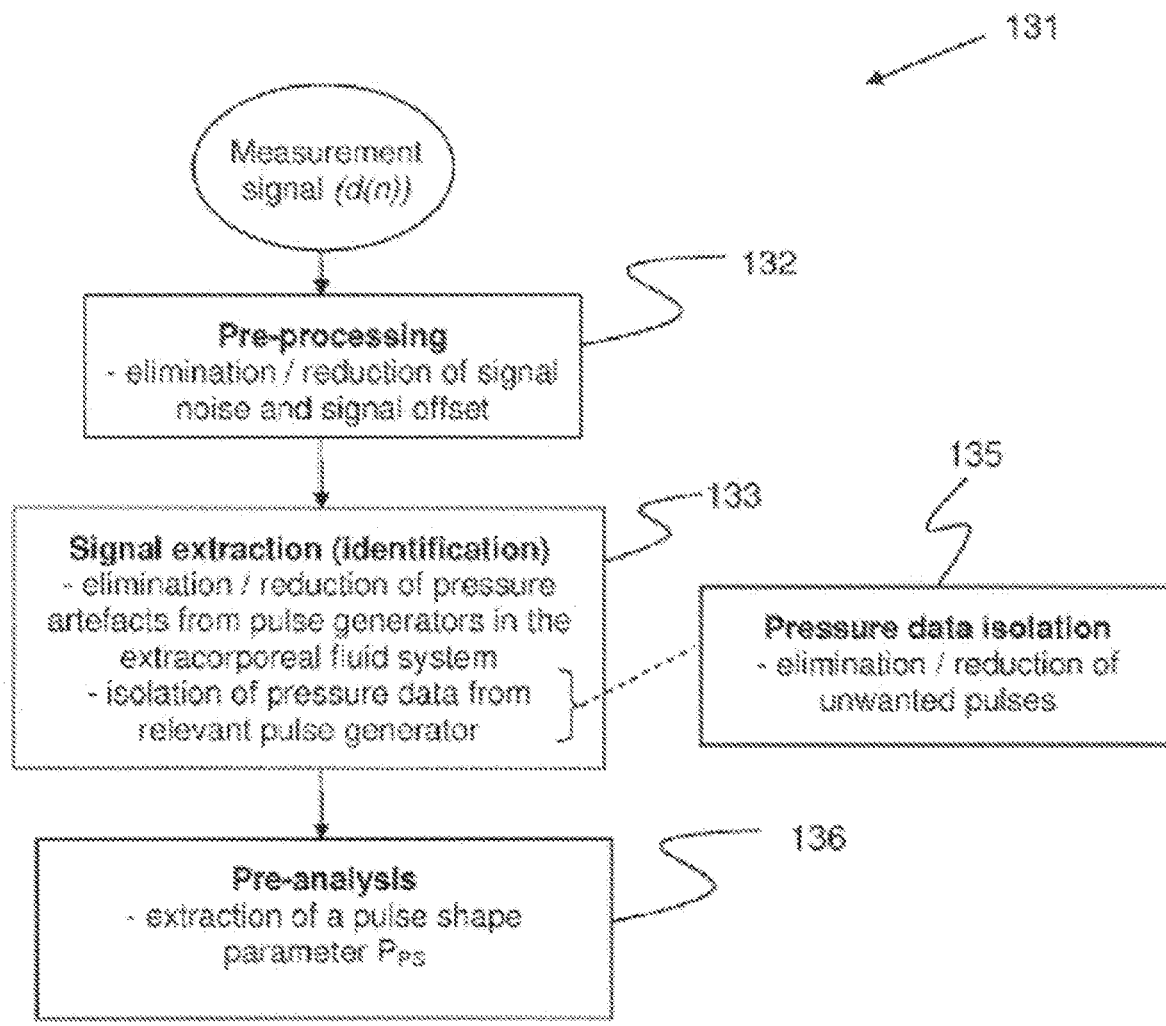
FIG. 13 is a flow chart of a signal analysis process according to an embodiment of the invention.

FIG. 13 is a flow chart that illustrates steps of a signal analysis process 131 according to an embodiment of the invention. The process 131 operates on measurement data obtained (sampled) from, e.g., the venous and/or arterial and/or system pressure sensors, thereby generating signal values of a measurement signal comprising a number of pressure induced signal components.

The measurement signal may comprise signals originating from more than one source and thus constitutes a composite signal of the signals from said sources. The measurement signal may be used without further processing, although preferably, the measurement signal may be processed for filtering to remove unwanted pressure data. Typically, the measurement signal includes pressure pulses that originate from a number of different pulse generators in the vascular system as well as the dialysis machine.

In the vascular system, the pulse generator may be a physiological phenomenon, such as the pulsation of the heart or the breathing movement of the lungs. Other physiological phenomena pulse generators may be an autonomous system for blood pressure regulation and an autonomous system for body temperature regulation.

In the dialysis machine, the pulse generator may be a fluid pump, such as a blood pump. The pump may be on the blood side or the fluid side of the extracorporeal system in a dialysis system. The pump may be of any type that generates pressure waves, for instance a peristaltic type of pump.

The pulse generators may be repetitive, such as the heart, breathing or pump or non-repetitive, such as pulses generated from coughing, sneezing, vomiting or seizures. Additionally, pulses may also be generated from separate, independent pulse generators, such as by rapid inflation of a blood pressure cuff to induce a pressure wave which propagates from the body part it is coupled to a blood vessel of the vascular system.

The signal analysis process 130 may be divided into a pre-processing part 132, a signal extraction part 133 and an analysis part 136. The pre-processing part 132 includes elimination or reduction of signal noise, e.g. measurement noise, and signal offset, e.g. as detailed in above with reference to the data acquisition part 28. Thus, the pre-processed part 132 may be seen to result in the above-mentioned pre-processed pressure signal (cf. FIGS. 3A and 4A). The signal extraction part 133 involves elimination or reduction of pressure artefacts originating from pulse generators in the extracorporeal fluid system and isolation of pressure data originating from a relevant physiological phenomenon. In the context of the present disclosure, "pressure data isolation" 135 denotes a process of generating a time-dependent signal ("monitoring signal") which is free or substantially free from pressure modulations caused by any unwanted physiological phenomena. Such unwanted physiological phenomena may vary between different applications, but generally include sneezing, coughing, etc. The elimination of signal noise and signal offset, as well as the elimination of pressure artefacts, may be included in algorithms for pressure data isolation. For instance, the measurement signal may be band pass filtered or low pass filtered to isolate a heart signal, in a way such that signal noise and/or signal offset and/or pressure artefacts are eliminated from the measurement signal. The elimination of pressure artefacts may thus be performed before, after or during the pressure data isolation.

In certain embodiments, the monitoring signal may be allowed to contain pressure modulations originating from more than one physiological phenomenon, and thus part 135 may be modified accordingly, or even omitted.

In the analysis part 136 of FIG. 13, the monitoring signal generated in part 133 is processed for extraction of the pulse shape parameter $p_{PS}$, which is then received by step 810 in FIG. 8. In this context, "processed for extraction" should be given a wide meaning. In one example, the pulse shape parameter $p_{PS}$ is indeed an extracted portion of the monitoring signal which is provided to the monitoring process in FIG. 8. However, in many practical implementations, the monitoring signal is provided as a continuous stream of signal values, which are received by the monitoring process in FIG. 8. In such an implementation, the extraction part 133 may identify sequences of signal values (signal segments) to be used as pulse shape parameters $p_{PS}$ by the monitoring process. The signal segments may e.g. be identified based on the above-mentioned timing information. Alternatively, the extraction part 133 may be omitted, e.g. if the monitoring process is designed to automatically operate on signal segments containing a fixed number of signal values (fixed time window) and having a given location in the monitoring signal. For example, the monitoring process may be designed to use signal segments containing n signal values, and to form a new pulse shape parameter $p_{PS}$ for every new m:th incoming signal value, by combining the m incoming signal values with the n-m most recent signal values. It is realized that the parameters n and m may be selected to optimize the performance of the monitoring process.

In the simplest case of pressure signal analysis, no pump or other source of pressure artefacts is present in the extracorporeal fluid circuit connected to the subject during the data acquisition. For instance, the pump may have been shut down. In such a case, the extraction part 133 may be identical to the pressure data isolation part 135.

In the general case, however, one or more pumps are running or other sources of cyclic or non-cyclic repetitive and non-repetitive artefacts are present during the data acquisition. Information on the cyclic disturbances may be known from external sources, e.g. other sensors, or may be estimated or reconstructed from system parameters.

Cyclic pressure artefacts may originate from operating a peristaltic pump, repetitive actuation of valves, movements of membranes in balancing chambers. According to the findings in connection with the present invention, artefacts may also originate from mechanical resonance of system components such as swinging movements of blood line energized by e.g. a pump. Frequencies of blood line movements are given by the tube lengths and harmonics thereof and by the beating between any frequencies involved, i.e. between different self-oscillations and pump frequencies. These frequencies may differ between the venous and arterial lines. Mechanical fixation of the blood lines and other free components may remedy the problem of mechanical resonance. Alternatively, an operator may be instructed to touch or jolt the blood lines to identify natural frequencies associated with the blood lines, which information may be used in the analysis for improved removal of components not belonging to the pressure data of interest.

Examples of non-cyclic artefacts are subject movement, valve actuation, movements of tubings etc.

Various techniques for use in the signal extraction part 133 will be discussed in Section IV below.

According to one embodiment of the present invention, it relates to a method (monitoring process) for predicting rapid symptomatic blood pressure decrease in a subject based on analysis of readings given by one or more pressure sensors integrated in a dialysis monitor. The pressure readings of each pressure sensor form a measurement signal. The measurement signal may comprise pressure data from different pulse generators in the dialysis machine and in the subject. Such pulse generators include the blood pump, the heart and other physiological phenomena in the subject, such as breathing. Before being input to the monitoring process, the measurement signal may be processed to remove artefacts from pulse generators in the dialysis machine and/or for isolation of pressure data from a particular origin, for instance the heart, breathing or a pump in the extracorporeal circuit (e.g. for use as a predicted signal profile of the pump pulses for use in time domain filtering, see Appendix A). The aforesaid measurement signal comprises continuously detected readings from the pressure sensor(s), thus representing an inherently time-dependent signal, and the aforesaid pressure data comprises at least a part of a pressure pulse or one or more pressure pulses originating from one or more pulse generators, such as the heart, the breathing system of the subject, one or more pumps or valves in the extracorporeal circuit, etc. Unless otherwise stated, it will in the following be assumed that the heart pulse is used, although the text is also applicable to the use of the breathing pulse.

The isolation of pressure data from a particular origin may involve filtering. However, in situations where no efficient filtration can be accomplished, for instance where the noise-to-signal ratio is too large, it may be advantageous to control the pump behaviour. For instance, in situations where harmonics of the pump ($f_0/2$, $f_0$, $2f_0$, $3f_0$, etc) overlap or are near the frequency of the physiological signal, such as the heart or breathing, the rotation speed of the pump may be adjusted so that the frequencies are separated. For instance, where the heart frequency and the fundamental frequency of the pump $f_0$ is 1 Hz, the pump may be adjusted to a new frequency of $\frac{2}{3}$ Hz, such that the heart frequency operates in the frequency range between the fundamental frequency of the pump and its first harmonic $2f_0$. Alternatively, the rotation speed of the pump may be adjusted to a relative level, such as 25 percent, from the frequency of the heart. Removal of the pump pulses, or vice versa, may then be accomplished easier, or even omitted.

Alternatively, the blood pump may be temporarily stopped to accomplish complete removal of influence caused by the pump. In order to obtain the necessary measurement data, while avoiding blood coagulation, it may be advantageous to stop the pump for at least 30 seconds and maximum five minutes. Longer duration of the stop increases the precision of the determination, which may also be achieved by repeatedly stopping the pump for shorter time periods.

IV. SIGNAL EXTRACTION OF PATIENT PULSES

In the following, embodiments for eliminating or reducing various pressure artefacts (also denoted "interference pulses") originating from one or more pulse generators in the dialysis machine will be described. Then, embodiments for isolating pressure data originating from a relevant physiological phenomenon among pressure pulses or pressure modulations originating from other physiological phenomena.

The pressure data to be extracted is not limited to a pressure pulses originating from a single physiological phenomenon and may include pressure pulses from more than one physiological phenomenon, including the heart. As used herein, the pressure data to be isolated is also denoted "patient pulses".

Elimination of Artefacts (Part 133)
  Elimination of artefacts may, e.g., be provided by:
  Controlling a pulse generator in the dialysis machine, such as a pump
    By temporarily shutting down the pulse generator;
    Shifting the frequency of the pulse generator;
  Low pass, band pass or high pass filtering;
  Spectral analysis and filtering in the frequency domain;
  Time domain filtering.
Controlling a Pulse Generator Artefacts from a pulse generator, such as a pump, in the dialysis machine may be avoided by temporarily shutting down (disabling) the pulse generator, or by shifting the frequency of the pulse generator away from frequencies of one or more relevant physiological phenomena.

A feedback control with respect to the heart rate, e.g. obtained from a dedicated pulse sensor attached to the patient or obtained via analysis of previous parts of the monitoring signal, may be used to set the pump frequency optimally for detection of heart pulses. Similar feedback control may be used to eliminate artefacts with respect to pressure pulses originating from breathing, e.g. based on a breathing signal from an independent source, such as a capnograph instrument. Hence, the control unit 23 of FIG. 1 may be operated to control the pump frequency in order to facilitate the detection of the patient pulses, e.g. the pump frequency is controlled to minimize any overlap in frequency between the pump pulses and the patient pulses. For example, the pump frequency may be periodically increased and decreased around the overlap frequency, so as to maintain the overall blood flow rate. In a variant, the pump frequency is instead controlled so as to synchronize the rate of pump pulses with the rate of patient pulses while applying a phase difference between the pump pulses and the patient pulses. Thereby, the pump pulses and the patient pulses will be separated in time, and the patient pulses may be detected in the time domain, even without removal of the pump pulses. The phase difference may be approximately 180°, since this may maximize the separation of the pump pulses and the patient pulses in the time domain. This so-called phase-locking technique may be activated when it is detected that the rate of patient pulses approaches the rate of pump pulses, or vice versa.

Applying Low Pass, Band Pass or High Pass Filters

The input signal to part 133 may be fed into a filter, e.g. digital or analog, with frequency characteristics, such as frequency range and/or centre of frequency range, matched to the frequencies generated by a pulse generator, such as a pump, in the dialysis machine. For instance, in a case where the pulse generator, such as a pump, operates within the frequency range of 1 Hz, a suitable low pass filter may be applied in order to remove pressure artefacts above 1 Hz while retaining frequency components of the physiological phenomenon below 1 Hz. Correspondingly, a high pass filter may be applied to retain frequency components above a frequency of the pulse generator. Alternatively, one or more notch filters or the like may be utilised to remove/attenuate frequencies in one or more confined ranges.

Spectral Analysis and Filtering in the Frequency Domain

The input signal to part 133 may be subjected to a spectral analysis, e.g. by applying a Fourier transformation technique, such as FFT (Fast Fourier Transform) to convert the input signal into the frequency domain. The resulting energy spectrum (amplitude spectrum) may then be multiplied by an appropriate filter function and then re-transformed into the time domain. There are many alternative and equivalent filtering techniques available to the skilled person.

Time Domain Filtering

Artefact elimination by filtering in the time domain is further disclosed and exemplified in Appendix A. In the context of Appendix A, the input signal to part 133 is denoted "measurement signal", and the resulting "filtered signal e(n)" corresponds to the monitoring signal, or an intermediate signal for input to step 135, depending on implementation.

In addition to Appendix A, reference is also made to Applicant's International patent publication WO2009/156175, entitled "Method and device for processing a time-dependent measurement signal", which is incorporated herein in its entirety by this reference.

It may be noted that the monitoring signal in FIG. 4B has been obtained by time domain filtering in accordance with the techniques proposed in Appendix A.

Isolating Pressure Data from a Physiological Phenomenon (Part 135)

Isolating pressure data originating from a relevant physiological phenomenon may be provided by any or a combination of:

Low pass, band pass or high pass filtering;
Spectral analysis and filtering in the frequency domain; or
Time domain filtering.

Applying Low Pass, Band Pass or High Pass Filters

The input signal to part 135 may be fed into a filter, e.g. digital or analog, with frequency characteristics, such as frequency range and/or centre of frequency range, matched to the frequencies of pressure pulses from a relevant physiological phenomenon where e.g. in case the isolation concerns:

Breathing, a frequency range substantially of 0.15-0.4 Hz will be allowed to pass the filter;
Blood pressure regulation due to the autonomous system, a frequency range substantially of 0.04-0.15 Hz will be allowed to pass the filter; and
Temperature regulation due to the autonomous system, a frequency range substantially of 0.001-0.1 Hz will be allowed to pass the filter.

Spectral Analysis and Filtering in the Frequency Domain

The input signal to part 135 may be subjected to a spectral analysis, e.g. by applying a Fourier transformation technique, such as FFT (Fast Fourier Transform) to convert the input signal into the frequency domain. The resulting energy spectrum (amplitude spectrum) may then be multiplied by an appropriate filter function and then re-transformed into the time domain. There are many alternative and equivalent filtering techniques available to the skilled person.

Pressure Data Isolation by Time Domain Filtering

The signal of interest may be extracted from the input signal to part 135 as an error signal of an adaptive filter. The adaptive filter is fed with both the measured pressure signal and a predicted signal profile of a cyclic disturbance. The cyclic disturbance may originate from any unwanted physiological phenomenon (e.g. heart pulsation or breathing). Particularly, a reconstructed pressure profile originating from the unwanted physiological phenomenon may be input to the adaptive filter. This and other time domain filtering techniques for removing unwanted signal components from a measurement signal is further disclosed and exemplified in Appendix A. Although Appendix A is concerned with eliminating first pulses originating from a pulse generator in an extracorporeal circuit, such as a pumping device, it is equally applicable for eliminating first pulses originating from unwanted physiological phenomena, as long as a predicted signal profile of the first pulses may be obtained. The skilled person realizes that such a predicted signal profile may be obtained in any of the ways described in Appendix A. In addition to Appendix A, reference is also made to aforesaid WO2009/156175.

Some of the filtering techniques described above may automatically be achieved by down-sampling, since it may be taken care of by the anti-aliasing filter included in a down-sampling signal processing algorithm. Additionally, some of the above described filtering techniques may also be achieved directly in hardware, e.g., in the Analog-to-Digital conversion by choosing an appropriate sample frequency, i.e. due to the anti-aliasing filter which is applied before sampling.

The invention has mainly been described above with reference to a few embodiments. However, as is readily appreciated by a person skilled in the art, other embodiments than the ones disclosed above are equally possible within the scope and spirit of the invention, which is defined and limited only be the appended patent claims.

For example, the illustrated embodiments are applicable for surveillance of all types of extracorporeal blood flow circuits in which blood is taken from a patient's circulation. Such blood flow circuits include hemodialysis, hemofiltration, hemodiafiltration, plasmapheresis, aphaeresis, extracorporeal membrane oxygenation, assisted blood circulation, and extracorporeal liver support/dialysis, bloodbanking, blood fraction separation (e.g. cells) of donor blood, etc.

Further, the inventive monitoring techniques are applicable to any type of pumping device that generates pressure pulses in the first fluid containing system, not only rotary peristaltic pumps as disclosed above, but also other types of positive displacement pumps, such as linear peristaltic pumps, diaphragm pumps, as well as centrifugal pumps.

The term "comprises/comprising" when used in this specification is taken to specify the presence of stated features, integers, steps or components. However, the term does not preclude the presence or addition of one or more additional features, integers, steps or components or groups thereof.

It is to be understood that Appendix A and Appendix B are to be treated as integral parts of the present application. However, reference numerals are defined within the context of each Appendix separately. In the event of conflicting use of terminology between the Appendix A, Appendix B and the main specification, the terminology should be interpreted within the context of Appendix A, Appendix B and the main specification, respectively.

In the following, a set of items are recited to summarize some aspects and embodiments of the invention as disclosed in the foregoing.

Item 1. A monitoring device (120) for predicting rapid symptomatic blood pressure decrease in a subject (P), the device comprising: an input (28) for receiving measurement data from at least one pressure sensor (4a, 4b, 4c) in an extracorporeal blood flow circuit (20) coupled to a cardiovascular system of the subject (P), the measurement data comprising a time sequence of pulse shape parameters ($p_{PS}$) representing pressure variations in at least one blood vessel of the subject (P); and a data analysis part (29) adapted to repeatedly receive the pulse shape parameters ($p_{PS}$), investigate whether or not a measure (PM, SM) of one or more of the pulse shape parameters ($p_{PS}$) fulfils a decision criterion, and if so, cause an output signal ($\alpha$) to be generated, the output signal ($\alpha$) indicating a predicted rapid symptomatic blood pressure decrease in the subject (P).

Item 2. The monitoring device of item 1, wherein the data analysis part (29) is further adapted to: obtain a reference measure; calculate, during a measurement period, a respective pulse measure (PM, SM) based on each of a number of received pulse shape parameters ($p_{PS}$); investigate, during the measurement period, whether or not the decision criterion, which is given relative to the reference measure, is fulfilled based on one or more of the pulse measures (PM, SM); and if so, causing the output signal ($\alpha$) to be generated.

Item 3. The monitoring device according to item 2, wherein the pulse measure is a pulse magnitude measure (PM) of a pulse shape parameter ($p_{PS}$).

Item 4. The monitoring device according to item 3, wherein the pulse magnitude measure (PM) is any of a peak-to-peak measure, an integration measure, an energy measure, and a frequency spectrum intensity measure calculated for the pulse shape parameter ($p_{PS}$).

Item 5. The monitoring device according to item 3 or 4, wherein the pulse measure (PM) is based on an average of a number of pulse magnitude measures.

Item 6. The monitoring device according to item 2, wherein the pulse measure is a statistical dispersion measure (SM) of a sequence of pulse magnitude measures (PM). The data analysis part may be further adapted to: investigate whether one or more of the pulse magnitude measures (PM) fulfils a second decision criterion relative to a second reference measure, and causing the output signal ($\alpha$) to be generated as a function of both said decision criterion and said second decision criterion.

Item 7. The monitoring device according to item 6, wherein the statistical dispersion measure (SM) is any of variance, standard deviation, coefficient of variation, variance-to-mean, a sum of differences, an energy measure, or any combinations thereof.

Item 8. The monitoring device according to any one of items 2-7, wherein the reference measure is a threshold value (T), and the decision criterion is fulfilled when a pulse measure (PM, SM) passes the threshold value (T). The threshold value (T) may be given by a predefined value.

Item 9. The monitoring device according to any one of items 2-8, wherein the data analysis part (29) further is adapted to: calculate as the reference measure an initial pulse measure (PM1, SM1) based on at least one pulse shape parameter ($p_{PS}$) received at a first instance ($t_1$); and store the initial pulse measure (PM1, SM1) in a memory means (30) associated with the monitoring device; wherein the measurement period is subsequent to the first instance ($t_1$).

Item 10. The monitoring device according to item 9, wherein the data analysis part (29) is adapted to regard the decision criterion as fulfilled if: an examined pulse measure (PM, SM) fulfils a first partial decision criterion calculated based on the initial pulse measure (PM1, SM1); and a predetermined amount of the pulse measures (PM, SM) calculated within a subsequent test period ($\tau$) fulfils a second partial decision criterion.

Item 11. The monitoring device according to item 10, wherein the predetermined amount is a value representing approximately 50% to approximately 100% of the pulse measures (PM, SM) calculated for the pulse shape parameters ($p_{PS}$) received within the test period ($\tau$).

Item 13. The monitoring device according to any one of items 10-12, wherein the test period ($\tau$) is an interval selected from a range extending from approximately one minute to approximately fifteen minutes.

Item 14. The monitoring device according to item 13, wherein the test period ($\tau$) is approximately five minutes long.

Item 15. The monitoring device according to any one of items 10-14, wherein the data analysis part (29) is adapted to calculate the decision criterion by: normalizing the initial pulse measure (PM1, SM1), and dividing the normalized initial pulse measure by a predefined denominator.

Item 16. The monitoring device according to item 15, wherein the data analysis part (29) is adapted to, during the measurement period, calculate a pulse measure (PM, SM) for a received pulse shape parameter ($p_{PS}$) by dividing an original measure with the initial pulse measure (PM1, SM1).

Item 17. The monitoring device according to item 16, wherein the pulse measure is a pulse magnitude measure (PM), and the predefined denominator is a value selected from a range extending from approximately 1.2 to approximately 5, or the pulse measure is a statistical dispersion measure (SM), and the predefined denominator is a value selected from a range extending from approximately 0.2 to approximately 0.8.

Item 18. The monitoring device according to any one of the preceding items, further comprising: an auxiliary input for receiving auxiliary measurement data from an auxiliary recording means (130) adapted to repeatedly register a bio-impedance parameter ($p_{BI}$) representing a degree of contraction of the subject's (P) capillary blood vessels; wherein the data analysis part (29) is further adapted to receive the bioimpedance parameter ($p_{BI}$), investigate whether or not the bio-impedance parameter ($p_{BI}$) fulfils an auxiliary decision criterion, and if so, generate the output signal ($\alpha$).

Item 19. The monitoring device according to any of items 10-17, which is adapted to predict rapid symptomatic blood pressure decrease in a subject (P) undergoing blood treatment, wherein the data analysis part (29) is adapted to calculate the initial pulse measure (PM1, SM1) based on one or more pulse shape parameters ($p_{PS}$) received during an initial phase of the blood treatment.

Item 20. The monitoring device according to any preceding item, wherein the decision criterion relates to a magnitude of one or more physiological pulses in the pulse shape parameter ($p_{PS}$), said one or more physiological pulses originating from a physiological pulse generator in the patient (P).

Item 21. The monitoring device according to item 20, wherein each pulse shape parameter ($p_{PS}$) corresponds to a time window in a pressure signal formed by the measurement data.

Item 22. The monitoring device according to item 21, wherein the time window is selected such that each pulse shape parameter ($p_{PS}$) comprises at least one physiological pulse originating from the physiological pulse generator in the subject (P).

Item 23. The monitoring device according to item 21 or 22, wherein the length of the time window is chosen to exceed a maximum pulse repetition interval of the physiological generator.

Item 24. The monitoring device according to any one of items 21-23, wherein the time windows are partially overlapping.

Item 25. The monitoring device according to any one of items 21-24, wherein the data analysis part (29) is adapted to set the time window based on timing information indicative of the timing of the physiological pulses in the pressure signal.

Item 26. The monitoring device according to item 25, wherein the data analysis part (29) is adapted to obtain the timing information from a pulse sensor coupled to the subject (P).

Item 27. The monitoring device according to item 25, wherein the data analysis part (29) is adapted to obtain the timing information as a function of the relative timing of physiological pulses identified in preceding pulse shape parameters.

Item 28. The monitoring device according to item 25, wherein the data analysis part (29) is adapted to: identify a set of candidate physiological pulses based on the pressure signal; derive a sequence of candidate time points based on the set of candidate physiological pulses; validate the sequence of candidate time points against a temporal criterion; and calculate the timing information as a function of the thus-validated sequence of candidate time points.

Item 29. The monitoring device according to item 25, wherein the extracorporeal blood flow circuit (20) comprises at least one pumping device (3), wherein the at least one pressure sensor (4a-4c) is arranged in the extracorporeal blood flow circuit (20) to detect interference pulses originating from said at least one pumping device (3) and physiological pulses originating from the physiological pulse generator in the subject (P), wherein data analysis part (29) is adapted to: intermittently turn off said at least one pumping device (3); identify at least one physiological pulse in said at least one pressure signal; and calculate the timing information from the thus-identified physiological pulse.

Item 30. The monitoring device according to any one of items 20-29, wherein the extracorporeal blood flow circuit (20) is associated with at least one pumping device (3), wherein the at least one pressure sensor (4a-4c) is arranged in the blood flow circuit (20) to detect interference pulses originating from said at least one pumping device (3) and physiological pulses originating from the physiological pulse generator in the subject (P).

Item 31. The monitoring device according to item 30, wherein the data analysis part (29) is further adapted to generate, based on a pressure signal formed by the measurement data, a time-dependent monitoring signal in which the interference pulses are essentially eliminated, whereupon the data analysis part (29) obtains the pulse shape parameters from the monitoring signal.

Item 32. The monitoring device according to item 31, wherein the data analysis part (29) is further adapted to generate the monitoring signal by: filtering the pressure signal to remove the interference pulses; deriving, based on timing information indicative of the timing of the physiological pulses in the pressure signal, a set of signal segments in the thus-filtered pressure signal; and aligning and adding the signal segments, based on the timing information, to generate said monitoring signal.

Item 33. The monitoring device according to item 31 or 32, wherein the data analysis part (29) is adapted to obtain a pulse profile (u(n)) which is a predicted temporal signal profile of the interference pulses, and to filter the measurement data in the time domain, using the pulse profile (u(n)), to essentially eliminate the interference pulses while retaining the physiological pulses.

Item 34. The monitoring device according to item 33, wherein the data analysis part (29) is adapted to subtract the pulse profile (u(n)) from the pressure signal.

Item 35. The monitoring device according to item 34, wherein the data analysis part (29) is adapted to, before subtracting the pulse profile (u(n)), adjust at least one of the amplitude, the time scale and the phase of the pulse profile (u(n)) with respect to the pressure signal.

Item 36. The monitoring device according to item 35, wherein the data analysis part (29) is adapted to minimize a difference between the pulse profile (u(n)) and the pressure signal.

Item 37. The monitoring device according to any one of items 34-36, wherein the data analysis part (29) is adapted to subtract the pulse profile (u(n)) by adjusting a phase of the pulse profile (u(n)) in relation to the pressure signal, wherein said phase is indicated by phase information obtained from at least one of: a pump rate sensor (25) coupled to said at least one pumping device (3), and a controller (24) for said at least one pumping device (3).

Item 38. The monitoring device according to item 33, wherein the data analysis part (29) comprises an adaptive filter (160) which is arranged to generate an estimation signal ($\hat{d}(n)$), based on the pulse profile (u(n)) and an error signal (e(n)) formed as a difference between the pressure signal and the estimation signal ($\hat{d}(n)$), whereby the adaptive filter (160) is arranged to essentially eliminate the interference pulses in the error signal (e(n)). Further, the adaptive filter (160) may be configured to generate the estimation signal ($\hat{d}(n)$) as a linear combination of M shifted pulse profiles (u(n)), and specifically the adaptive filter (160) may be configured to linearly combine M instances of the pulse profiles (u(n)), which are properly adjusted in amplitude and phase by the adaptive filter (160).

Item 39. The monitoring device according to item 38, wherein the adaptive filter (160) comprises a finite impulse response filter (162) with filter coefficients that operate on the pulse profile (u(n)) to generate the estimation signal ($\hat{d}(n)$), and an adaptive algorithm (164) which optimizes the filter coefficients as a function of the error signal (e(n)) and the pulse profile (u(n)).

Item 40. The monitoring device according to item 38 or 39, wherein the data analysis part (29) is adapted to control the adaptive filter (160) to lock the filter coefficients, based on a comparison of the rate and/or amplitude of the physiological pulses to a limit value.

Item 41. The monitoring device according to item 33 to 40, wherein the data analysis part (29) is adapted to, in a reference measurement, cause said at least one pumping device (3) to generate at least one interference pulse, and obtain the pulse profile (u(n)) from a reference signal generated by a reference sensor (4a-4c). The reference sensor may be a pressure sensor in the extracorporeal blood flow circuit. The extracorporeal blood flow circuit may be operated, during the reference measurement, such that the reference signal contains an interference pulse and no physiological pulse.

Item 42. The monitoring device according to item 41, wherein said at least one pumping device (3) is operated to generate a sequence of interference pulses during the reference measurement, and wherein the pulse profile (u(n)) is obtained by identifying and combining a set of interference pulses in the reference signal.

Item 43. The monitoring device according to item 41 or 42, wherein the data analysis part (29) is adapted to intermittently effect the reference measurement to update the pulse profile (u(n)) during operation of the extracorporeal blood flow circuit (20).

Item 44. The monitoring device according to any one of items 41-43, wherein the data analysis part (29) is adapted to effect the reference measurement by: obtaining a combined pulse profile based on a first reference signal containing an interference pulse and a physiological pulse; obtaining a physiological pulse profile based on a second reference signal containing a physiological pulse and no interference pulse, and obtaining the predicted signal profile by subtracting the physiological pulse profile from the combined pulse profile.

Item 45. The monitoring device according to item 33 to 40, wherein the data analysis part (29) is adapted to obtain the pulse profile (u(n)) based on a predetermined signal profile.

Item 46. The monitoring device according to item 45, wherein the data analysis part (29) is adapted to modify the predetermined signal profile according to a mathematical model based on a current value of one or more system parameters of the extracorporeal blood flow circuit (20).

Item 47. The monitoring device according to item 33 to 40, wherein the data analysis part (29) is adapted to obtain a current value of one or more system parameters of the extracorporeal blood flow circuit (20), and to obtain the pulse profile (u(n)) as a function of the current value.

Item 48. The monitoring device according to item 47, wherein the data analysis part (29) is adapted to obtain the pulse profile (u(n)) by identifying, based on the current value, one or more temporal reference profiles ($r_1(n)$, $r_2(n)$) in a reference database (DB); and obtaining the pulse profile (u(n)) based on said one or more temporal reference profiles ($r_1(n)$, $r_2(n)$).

Item 49. The monitoring device according to item 48, wherein said one or more system parameters is indicative of a pumping rate of said at least one pumping device (3).

Item 50. The monitoring device according to item 48 or 49, wherein each temporal reference profile ($r_1(n)$, $r_2(n)$) in the reference database (DB) is obtained by a reference measurement in the extracorporeal blood flow circuit (20) for a respective value of said one or more system parameters.

Item 51. The monitoring device according to item 50, wherein the data analysis part (29) is adapted to obtain the pulse profile (u(n)) by identifying, based on the current value, one or more combinations of energy and phase angle data in a reference database (DB); and obtaining the pulse profile (u(n)) based on said one or more combinations of energy and phase angle data.

Item 52. The monitoring device according to item 51, wherein the data analysis part (29) is adapted to obtain the pulse profile (u(n)) by combining a set of sinusoids of different frequencies, wherein the amplitude and phase angle of each sinusoid is given by said one or more combinations of energy and phase angle data.

Item 53. The monitoring device according to item 47, wherein the data analysis part (29) is adapted to obtain the pulse profile (u(n)) by inputting the current value into an algorithm which calculates the response of the pressure sensor (4a-4c) based on a mathematical model of the extracorporeal blood flow circuit (20).

Item 54. The monitoring device according to item 31 or 32, wherein the data analysis part (29) is adapted to obtain a pulse profile (u(n)) which is a predicted temporal signal profile of the physiological pulse, and to filter the pressure signal in the time domain, using the pulse profile (u(n)), to essentially eliminate the interference pulse while retaining the physiological pulses.

Item 55. The monitoring device according to item 54, wherein the data analysis part (29) comprises an adaptive filter (160) which is arranged to generate an estimation signal ($\hat{d}(n)$), based on the pulse profile (u(n)) and an error signal (e(n)) formed as a difference between the measurement data and the estimation signal ($\hat{d}(n)$), whereby the adaptive filter (160) is arranged to essentially eliminate the interference pulses in the estimation signal ($\hat{d}(n)$). The adaptive filter (160) may be configured to generate the estimation signal ($\hat{d}(n)$) as a linear combination of M shifted pulse profiles (u(n)), and specifically the adaptive filter (160) may be configured to linearly combine M instances of the pulse profile (u(n)), which are properly adjusted in amplitude and phase by the adaptive filter (30).

Item 56. The monitoring device according to any one of items 30-55, wherein the data analysis part (29) is further adapted to calculate a rate of physiological pulses in the monitoring signal, or in a reference signal obtained from a reference sensor (4a-4c), and to cause a pumping frequency of said at least one pumping device (3) to be controlled in relation to the rate of physiological pulses.

Item 57. The monitoring device according to item 56, wherein the pumping frequency is controlled to shift the rate of interference pulses away from the rate of physiological pulses.

Item 58. The monitoring device according to item 56, wherein the pumping frequency is controlled to synchronize the rate of interference pulses with the rate of physiological pulses, while applying a given phase difference between the interference pulses and the physiological pulses.

Item 59. The monitoring device according to any one of items 30-55, wherein the data analysis part (29) is adapted to receive the pulse shape parameters while said at least one pumping device (3) is intermittently set in a disabled state.

Item 60. The monitoring device according to any one of items 20-59, wherein the physiological pulse generator is at least one of a heart, a breathing system, and a vasomotor affected by an autonomic nervous system.

Item 100. A monitoring arrangement (100) for predicting rapid symptomatic blood pressure decrease in a subject (P), the arrangement comprising: an extracorporeal blood flow circuit (20) configured to be coupled to a cardiovascular system of the subject (P), said extracorporeal blood flow circuit (20) comprising at least one pressure sensor (4a, 4b, 4c) for generating measurement data comprising a time sequence of pulse shape parameters ($p_{PS}$) representing pressure variations in at least one blood vessel of the subject (P); and the monitoring device (120) according to any one of items 1-60.

Item 101. A medical system (200) adapted to perform blood treatment of a subject (P), wherein the system comprises: a dialysis machine (210) adapted to perform extracorporeal blood treatment of the subject (P) and comprising an extracorporeal blood flow circuit (20) configured to be coupled to a cardiovascular system of the subject (P), said extracorporeal blood flow circuit (20) comprising at least one pressure sensor (4a, 4b, 4c) for generating measurement data comprising a time sequence of pulse shape parameters ($p_{PS}$) representing pressure variations in at least one blood vessel of the subject (P); and the monitoring device (120) according to any one of the items 1-60.

Item 102. The medical system according to item 101, wherein the dialysis machine (210) is configured to, based on the output signal ($\alpha$), activate systems to counter-act the occurrence of a hypotension event including any of adjusting a rate of fluid removal from the subject by reducing and/or stopping the rate of fluid removal in case of fulfilled decision criterion, increasing the conductivity in the dialysis fluid, supplying a saline bolus to a blood line connected to the cardiovascular system of the subject, adjusting the positioning of the subject, setting a dialysis monitor in bypass, or any combinations thereof.

Item 200. A method for predicting rapid symptomatic blood pressure decrease in a subject (P), the method comprising: receiving measurement data from at least one pressure sensor (4a, 4b, 4c) in an extracorporeal blood flow circuit (20) coupled to a cardiovascular system of the subject (P), the measurement data comprising a time sequence of pulse shape parameters ($p_{PS}$) representing pressure variations in at least one blood vessel of the subject (P); investigating whether or not a measure (PM, SM) of one or more of the pulse shape parameters ($p_{PS}$) fulfils a decision criterion; and causing, if the decision criterion is fulfilled, an output signal ($\alpha$) to be generated, the output signal ($\alpha$) indicating a predicted rapid symptomatic blood pressure decrease in the subject (P).

Item 201. The method according to item 200, further comprising: receiving a reference measure; calculating, during a measurement period, a respective pulse measure (PM, SM) based on each of a number of received pulse shape parameters ($p_{PS}$); investigating, during the measurement period, whether or not the decision criterion, which is given relative to the reference measure, is fulfilled based on one of more of the pulse measures (PM, SM); and causing, if the decision criterion is fulfilled, the output signal ($\alpha$) to be generated.

Item 202. The method according to item 201, wherein the pulse measure is one of a pulse magnitude measure (PM) of the pulse shape parameter ($p_{PS}$), and a statistical dispersion measure (SM) of a sequence of pulse magnitude measures (PM).

Item 203. The method according to item 201 or 202, wherein the reference measure is a threshold value (T), and the decision criterion is fulfilled if: when a pulse measure (PM, SM) passes the threshold value (T).

Item 204. The method according to any one of items 201-203, the method further comprising: calculating as the reference measure an initial pulse measure (PM1, SM1) based on at least one pulse shape parameter ($p_{PS}$) received at a first instance ($t_1$); and storing the initial pulse measure (PM1, SM1) in a memory means (30); wherein the measurement period is subsequent to the first instance ($t_1$).

Item 205. The method according to item 204, wherein the decision criterion is fulfilled if: an examined pulse measure (PM, SM) fulfils a first partial decision criterion calculated based on the initial pulse measure (PM1, SM1); and a predetermined amount of the pulse measures (PM, SM) of the pulse shape parameters ($p_{PS}$) received within a subsequent test period ($\tau$) fulfils a second partial decision criterion.

Item 206. The method according to item 204 or 205, the method further comprising calculating the decision criterion by: normalizing the initial pulse measure (PM1, SM1); and dividing the normalized initial pulse measure by a predefined denominator.

Item 207. The method according to any one of items 204-206, the method further comprising calculating a pulse measure (PM, SM) for a received pulse shape parameter ($p_{PS}$) by dividing an original measure with the initial pulse measure (PM1, SM1).

Item 208. The method according to any of items 200-207, the method further comprising counter-acting the occurrence of a hypotension event including any of adjusting a rate of fluid removal from the subject by reducing and/or stopping the rate of fluid removal in case of fulfilled decision criterion, increasing the conductivity in the dialysis fluid, supplying a saline bolus to a blood line connected to the cardiovascular system of the subject, adjusting the positioning of the subject, setting a dialysis monitor in bypass, or any combinations thereof.

Item 250. A computer program directly loadable into the internal memory of a computer, comprising software for controlling the steps of any of items 200-208 when said program is run on the computer.

Item 251. A computer readable medium, having a program recorded thereon, where the program is to make a computer control the steps of any of the items 200-208.

Item 300. A monitoring arrangement (100) for predicting rapid symptomatic blood pressure decrease in a subject (P), the arrangement comprising: an extracorporeal blood flow circuit (20) configured to be coupled to a cardiovascular system of a subject; a pulse recording means (4a, 4b, 4c) adapted to repeatedly register a pulse shape parameter ($p_{PS}$) of the subject (P); and a surveillance device (25) adapted to receive the pulse shape parameter ($p_{PS}$), investigate whether or not the pulse shape parameter ($p_{PS}$) fulfils a decision criterion, and if so, cause an output to be generated, wherein the pulse recording means comprises a pressure sensor (4a, 4b, 4c) in the extracorporeal blood flow circuit adapted to register the pulse shape parameter ($p_{PS}$) based on pressure variations in at least one blood vessel of the subject (P), and the surveillance device (25) comprises a data analysis part (29) adapted to: receive a reference measure; calculate, during a measurement period, a respective pulse measure (PM) based on each of a number of received pulse shape parameters ($p_{PS}$); investigate, for each pulse measure (PM) in the measurement period, whether or not a decision criterion relative to the reference measure is fulfilled based at least partly on the pulse measure (PM), and if so, generate an output signal ($\alpha$).

Item 301. The arrangement according to item 300, wherein the pulse measure (PM) is a pulse magnitude measure (PMM).

Item 302. The arrangement according to item 300, wherein the pulse measure (PM) is a statistical dispersion measure (SM) of a pulse magnitude measure (PMM).

Item 303. The arrangement according to item 302, wherein the statistical dispersion measure (SM) is any of variance, standard deviation or any combinations thereof.

Item 304. The arrangement according to item 300, wherein the pulse measure (PM) is based on an average of a number of pulse magnitude measures.

Item 305. The arrangement according to item 300, wherein the reference measure is a threshold value (T), and the decision criterion is fulfilled when a pulse measure (PM) exceeds the threshold value (T).

Item 306. The arrangement according to item 300, wherein the data analysis part (29) further is adapted to: calculate as the reference measure an initial pulse measure (PM1) based on a pulse shape parameter ($p_{PS}$) received at a first instance ($t_1$); store the initial pulse measure (PM1) in a memory means (123) associated with the surveillance device (25); and wherein the measurement period is subsequent to the first instance ($t_1$).

Item 307. The arrangement according to item 306, wherein the data analysis part (29) is adapted to regard the decision criterion as fulfilled if: an examined pulse measure (PM) of a given pulse shape parameter fulfils a first partial decision criterion calculated based on the initial pulse measure (PM1); and a predetermined amount of the pulse measures (PM) of the pulse shape parameters ($p_{PS}$) received within a test period ($\tau$) after the given pulse shape parameter fulfils a second partial decision criterion.

Item 308. The arrangement according to item 306, wherein the predetermined amount is a value representing approximately 50% to approximately 100% of the pulse measures (PM) of the pulse shape parameters ($p_{PS}$) received within the test period ($\tau$).

Item 309. The arrangement according to item 306, wherein the predetermined amount represents all the pulse measures (PM) of the pulse shape parameters ($p_{PS}$) received within the test period ($\tau$).

Item 310. The arrangement according to any one of the items 306 to 309, wherein the test period ($\tau$) is an interval selected from a range extending from approximately three minutes to approximately fifteen minutes.

Item 311. The arrangement according to item 310, wherein the test period ($\tau$) is approximately five minutes long.

Item 312. The arrangement according to any one of the items 306 to 311, wherein the processing unit (128) is adapted to calculate the decision criterion by: normalizing the initial pulse measure (PM1); and dividing the normalized initial pulse measure by a predefined denominator.

Item 313. The arrangement according to item 312, wherein the processing unit (128) is adapted to, during the measurement period, calculate a pulse measure (PM) for a received pulse shape parameter ($p_{PS}$) by dividing an original measure with the initial pulse measure (PM1).

Item 314. The arrangement according to item 313, wherein the predefined denominator is a value selected from a range extending from approximately 1.2 to approximately 5.

Item 315. The arrangement according to any one of items 300 to 314, wherein the arrangement comprises: an auxiliary recording means (130) adapted to repeatedly register a bio-impedance parameter ($p_{BI}$) representing a degree of contraction of the subject's (P) capillary blood vessels; and the processing unit (128) is further adapted to receive the bio-impedance parameter ($p_{BI}$), investigate whether or not the bioimpedance parameter ($p_{BI}$) fulfils an auxiliary decision criterion, and if so, generate the output signal ($\alpha$).

Item 316. The arrangement according to any of items 306 to 314, wherein the arrangement is adapted to predict rapid symptomatic blood pressure decrease in a subject (P) undergoing blood treatment, and the processing unit (128) is adapted to calculate the initial pulse measure (PM1) based on a pulse shape parameter ($p_{PS}$) received during an initial phase of the blood treatment.

Item 317. The arrangement according to any of items 300 to 316, wherein the arrangement further is configured to activate systems to counter-act the occurrence of a hypotension event including any of adjusting a rate of fluid removal from the subject by reducing and/or stopping the rate of fluid removal in case of fulfilled decision criterion, increasing the conductivity in the dialysis fluid, supplying a saline bolus to a blood line connected to the cardiovascular system of the subject, adjusting the positioning of the subject, setting a dialysis monitor in bypass, or any combinations thereof.

Item 318. A medical system (200) adapted to perform blood treatment of a subject (P), wherein the system comprises: a dialysis machine (210) adapted to perform extracorporeal blood treatment of the subject (P); and the arrangement (100) according to any one of the preceding items.

Item 319. A method for predicting rapid symptomatic blood pressure decrease in a subject (P), the method comprising: repeatedly registering a pulse shape parameter ($p_{PS}$) of a subject (P); and receiving the pulse shape parameter ($p_{PS}$), investigating whether or not the pulse shape parameter ($p_{PS}$) fulfils a decision criterion, and if so, causing an output to be generated, the method further comprising: receiving a reference measure; calculating, during a measurement period, a respective pulse measure (PM) based on each of a number of received pulse shape parameters ($p_{PS}$); investigating, for each pulse measure (PM) in the measurement period, whether or not a decision criterion relative to the reference measure is fulfilled based at least partly on the pulse measure (PM), and if so, generate an output signal ($\alpha$).

Item 320. The method according to item 319, wherein the decision criterion is fulfilled if: a statistical dispersion measure (SM) of the pulse measures (PM) of the pulse shape parameters ($p_{PS}$) received within a test period ($\tau$) is above a statistical dispersion threshold value.

Item 321. The method according to item 319, the method further comprising: calculating as the reference measure an initial pulse measure (PM1) based on a pulse shape parameter ($p_{PS}$) received at a first instance ($t_1$); storing the initial pulse magnitude measure (PM1) in a memory means (123) associated with the surveillance device (25); and wherein the measurement period is subsequent to the first instance (t1).

Item 322. The method according to item 321, wherein the decision criterion is fulfilled if: an examined pulse measure (PM) of a given pulse shape parameter fulfils a first partial decision criterion calculated based on the initial pulse measure (PM1); and a predetermined amount of the pulse measures (PM) of the pulse shape parameters ($p_{PS}$) received within a test period ($\tau$) after the given pulse shape parameter fulfils a second partial decision criterion.

Item 323. The method according to item 322, the method further comprising calculating the decision criterion by: normalizing the initial pulse measure (PM1); and dividing the normalized initial pulse measure by a predefined denominator.

Item 324. The method according to item 323, the method further comprising calculating a pulse measure (PM) for a received pulse shape parameter ($p_{PS}$) by dividing an original measure with the initial pulse measure (PM1).

Item 325. The method according to any of the items 319 to 324, the method further comprising counter-acting the occurrence of a hypotension event including any of adjusting a rate of fluid removal from the subject by reducing and/or stopping the rate of fluid removal in case of fulfilled decision criterion, increasing the conductivity in the dialysis fluid, supplying a saline bolus to a blood line connected to the cardiovascular system of the subject, adjusting the positioning of the subject, setting a dialysis monitor in bypass, or any combinations thereof.

Item 326. A monitoring arrangement (100) for predicting rapid symptomatic blood pressure decrease in a subject (P), the arrangement comprising: means for repeatedly registering a pulse shape parameter ($p_{PS}$) of a subject (P); and means for receiving the pulse shape parameter ($p_{PS}$), investigating whether or not the pulse shape parameter ($p_{PS}$) fulfils a decision criterion, and if so, causing an output to be generated, the arrangement further comprising: means for receiving a reference measure; means for calculating, during a measurement period, a respective pulse measure (PM) based on each of a number of received pulse shape parameters ($p_{PS}$); means for investigating, for each pulse measure (PM) in the measurement period, whether or not a decision criterion relative to the reference measure is fulfilled based at least partly on the pulse measure (PM), and if so, generate an output signal ($\alpha$).

APPENDIX A

Brief Description of the Drawings

Exemplifying embodiments of the invention will now be described in more detail with reference to the accompanying schematic drawings FIGS. 14 to 25 discussed herein above.

DETAILED DESCRIPTION OF EXEMPLIFYING EMBODIMENTS

In the following, exemplifying embodiments of the invention will be described with reference to fluid containing systems in general. Thereafter, the embodiments and implementations of the invention will be further exemplified in the context of systems for extracorporeal blood treatment.

Throughout the following description, like elements are designated by the same reference signs.

General

Figure 14:
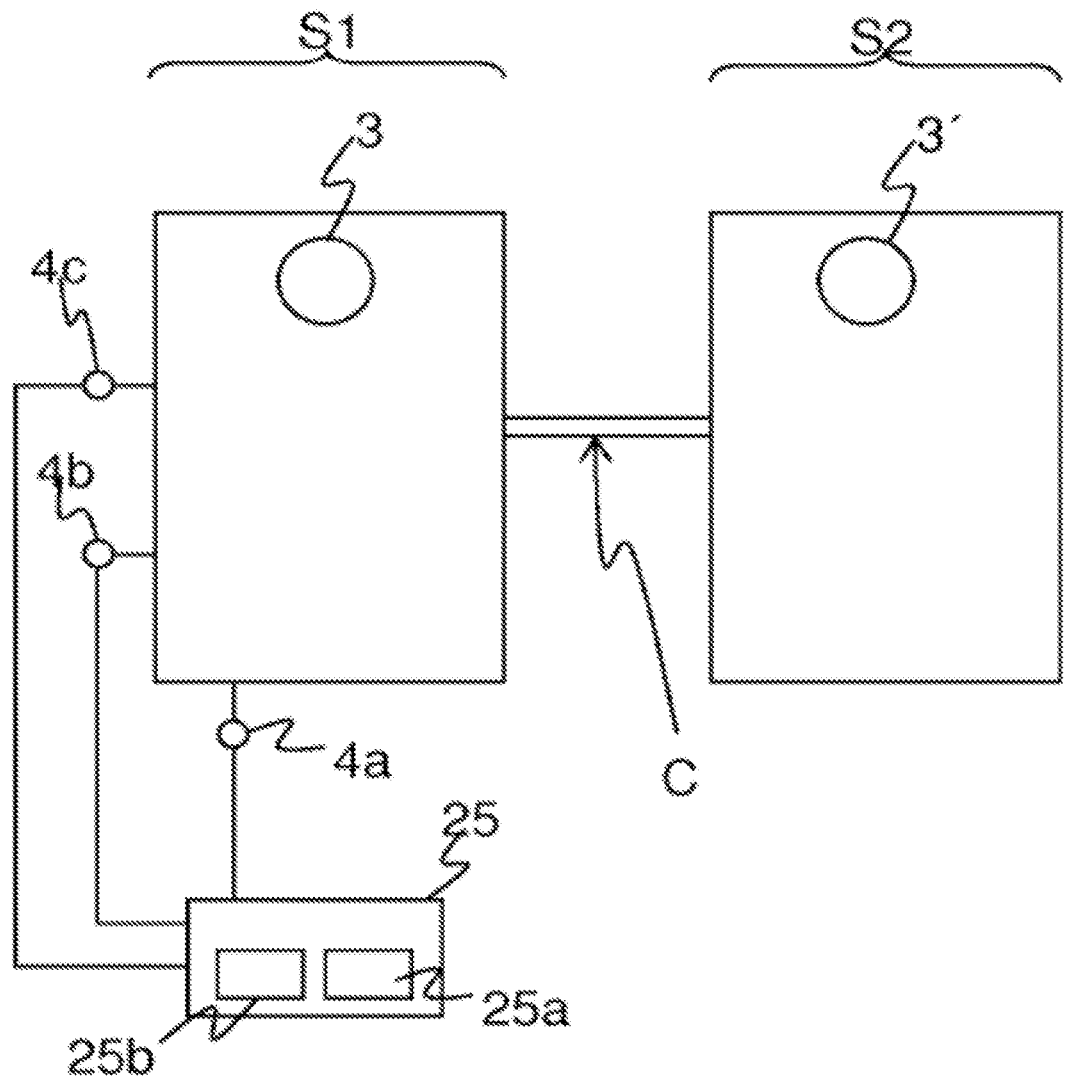
FIG. 14 is a schematic view of a general fluid containing system in which the inventive data processing may be used for filtering a pressure signal.

FIG. 14 illustrates a fluid containing system in which a fluid connection C is established between a first fluid containing sub-system S1 and a second fluid containing sub-system S2. The fluid connection C may or may not transfer fluid from one sub-system to the other. A first pulse generator 3 is arranged to generate a series of pressure waves in the fluid within the first sub-system S1, and a second pulse generator 3' is arranged to generate a series of pressure waves in the fluid within the second sub-system S2. A pressure sensor 4a is arranged to measure the fluid pressure in the first sub-system S1. Pressure waves generated by the second pulse generator 3' will travel from the second sub-system S2 to the first sub-system S1, via the connection C, and thus second pulses originating from the second pulse generator 3' will be detected by the pressure sensor 4a in addition to first pulses originating from the first pulse generator 3. It is to be noted that either one of the first and second pulse generators 3, 3' may include more than one pulse-generating device. Further, any such pulse-generating device may or may not be part of the respective sub-system S1, S2.

The system of FIG. 14 further includes a surveillance device 25 which is connected to the pressure sensor 4a, and possibly to one or more additional pressure sensors 4b, 4c, as indicated in FIG. 14. Thereby, the surveillance device 25 acquires one or more pressure signals that are time-dependent to provide a real time representation of the fluid pressure in the first sub-system S1.

Generally, the surveillance device 25 is configured to monitor a functional state or functional parameter of the fluid containing system, by isolating and analysing one or more second pulses in one of the pressure signals. As will be further exemplified in the following, the functional state or parameter may be monitored to identify a fault condition, e.g. in the first or second sub-systems S1, S2, the second pulse generator 3' or the fluid connection C. Upon identification of a fault condition, the surveillance device 25 may issue an alarm or warning signal and/or alert a control system of the first or second sub-systems S1, S2 to take appropriate action. Alternatively or additionally, the surveillance device 25 may be configured to record or output a time sequence of values of the functional state or parameter.

Depending on implementation, the surveillance device 25 may use digital components or analog components, or a combination thereof, for receiving and processing the pressure signal. The device 25 may thus be a computer, or a similar data processing device, with adequate hardware for acquiring and processing the pressure signal in accordance with different embodiments of the invention. Embodiments of the invention may e.g. be implemented by software instructions that are supplied on a computer-readable medium for execution by a processor 25a in conjunction with a memory unit 25b in the computer.

Typically, the surveillance device 25 is configured to continuously process the time-dependent pressure signal(s) to isolate any second pulses. This processing is schematically depicted in the flow chart of FIG. 15. The illustrated processing involves a step 201 of obtaining a first pulse profile $u(n)$ which is a predicted temporal signal profile of the first pulse(s), and a step 202 of filtering the pressure signal $d(n)$, or a preprocessed version thereof, in the time-domain, using the first pulse profile $u(n)$, to essentially eliminate or cancel the first pulse(s) while retaining the second pulse(s) contained in $d(n)$. In the context of the present disclosure, n indicates a sample number and is thus equivalent to a (relative) time point in a time-dependent signal. In step 203, the resulting filtered signal $e(n)$ is then analysed for the purpose of monitoring the aforesaid functional state or parameter.

The first pulse profile is a shape template or standard signal profile, typically given as a time-sequence of data values, which reflects the shape of the first pulse in the time domain. The first pulse profile is also denoted "predicted signal profile" in the following description.

By "essentially eliminating" is meant that the first pulse(s) is (are) removed from the pressure signal to such an extent that the second pulse(s) may be detected and analysed for the purpose of monitoring the aforesaid functional state or parameter.

By filtering the pressure signal in the time-domain, using the first pulse profile, it is possible to essentially eliminate the first pulses and still retain the second pulses, even if the first and second pulses overlap or nearly overlap in the frequency domain. Such a frequency overlap is not unlikely, e.g. if one or both of the first and second pulses is made up of a combination of frequencies or frequency ranges.

Furthermore, the frequency, amplitude and phase content of the first pulse or the second pulse may vary over time. Such variations may be the result of an active control of the first and/or second pulse generator 3, 3', or be caused by drifts in the first and/or second pulse generator 3, 3' or by changes in the hydrodynamic properties of the sub-systems S1, S2 or the fluid connection C. Frequency variations may occur, e.g., when the second pulse generator 3' is a human heart, and the second sub-system S2 thus is the blood system of a human. In healthy subjects under calm conditions, variations in heart rhythm (heart rate variability, HRV) may be as large as 15%. Unhealthy subjects may suffer from severe heart conditions such as atrial fibrillation and supraventricular ectopic beating, which may lead to an HRV in excess of 20%, and ventricular ectopic beating, for which HRV may be in excess of 60%. These heart conditions are not uncommon among, e.g., dialysis patients.

Any frequency overlap may make it impossible or at least difficult to isolate the second pulses in the pressure signal by conventional filtering in the frequency domain, e.g. by operating a comb filter and/or a combination of band-stop or notch filters, typically cascade coupled, on the pressure signal to block out all frequency components originating from the first pulse generator 3. Furthermore, frequency variations make it even harder to successfully isolate second pulses in the pressure signal, since the frequency overlap may vary over time. Even in the absence of any frequency overlap, frequency variations make it difficult to define filters in the frequency domain.

Depending on how well the first pulse profile represents the first pulse(s) in the pressure signal, it may be possible to isolate the second pulses by means of the inventive filtering in the time-domain even if the first and second pulses overlap in frequency, and even if the second pulses are much smaller in amplitude than the first pulses.

Still further, the inventive filtering in the time domain may allow for a faster isolation of second pulses in the pressure signal than a filtering process in the frequency domain. The former may have the ability to isolate a single second pulse in the pressure signal whereas the latter may need to operate on a sequence of first and second pulses in the pressure signal. Thus, the inventive filtering may enable faster determination of the functional state or functional parameter of the fluid containing system.

Figure 16A:
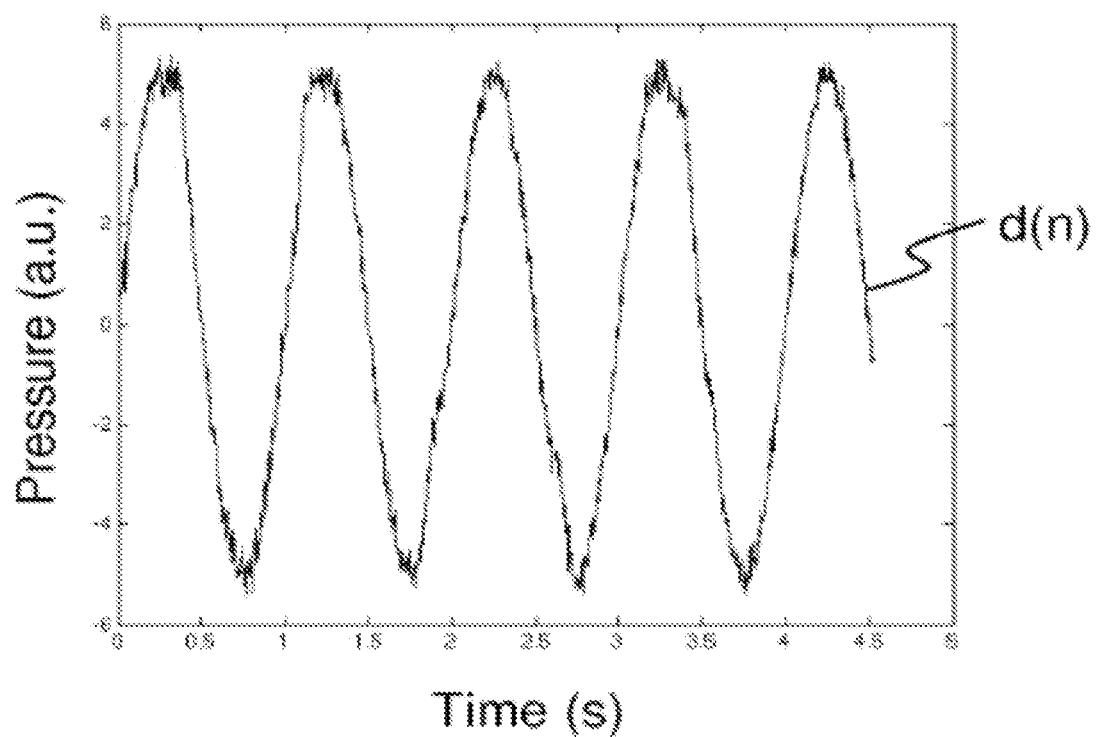
FIG. 16A is a plot of a pressure signal as a function of time.
Figure 16B:
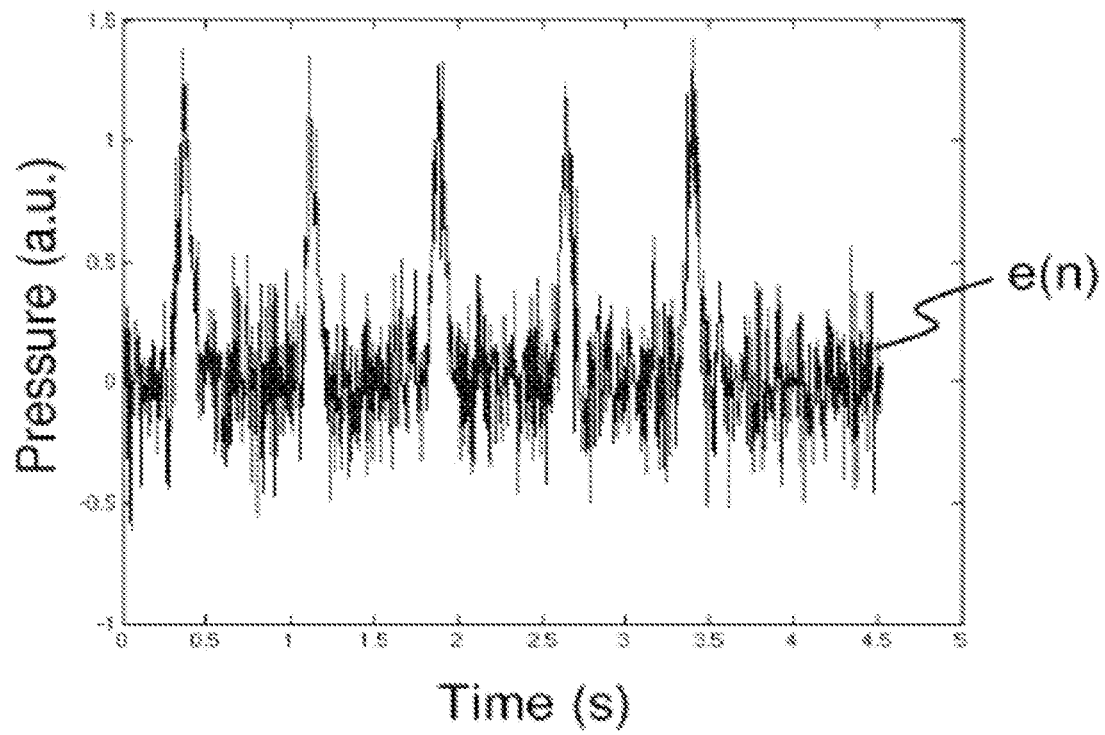
FIG. 16B is a plot of the pressure signal after filtering.

The effectiveness of the inventive filtering is exemplified in FIG. 16A and 16B, in which FIG. 16A shows an example of a time-dependent pressure signal d(n) containing first and second pulses with a relative magnitude of 10:1. The first and second pulses have a frequency of 1 Hz and 1.33 Hz, respectively. Due to the difference in magnitude, the pressure signal is dominated by the first pulses. FIG. 16B shows the time-dependent filtered signal e(n) that is obtained after applying the inventive filtering technique to the pressure signal d(n). The filtered signal e(n) is made up of second pulses and noise. It should be noted that there is an absence of second pulses after about 4 seconds, which may be observed by the surveillance device (25 in FIG. 14) and identified as a fault condition of the fluid containing system.

Figure 15:
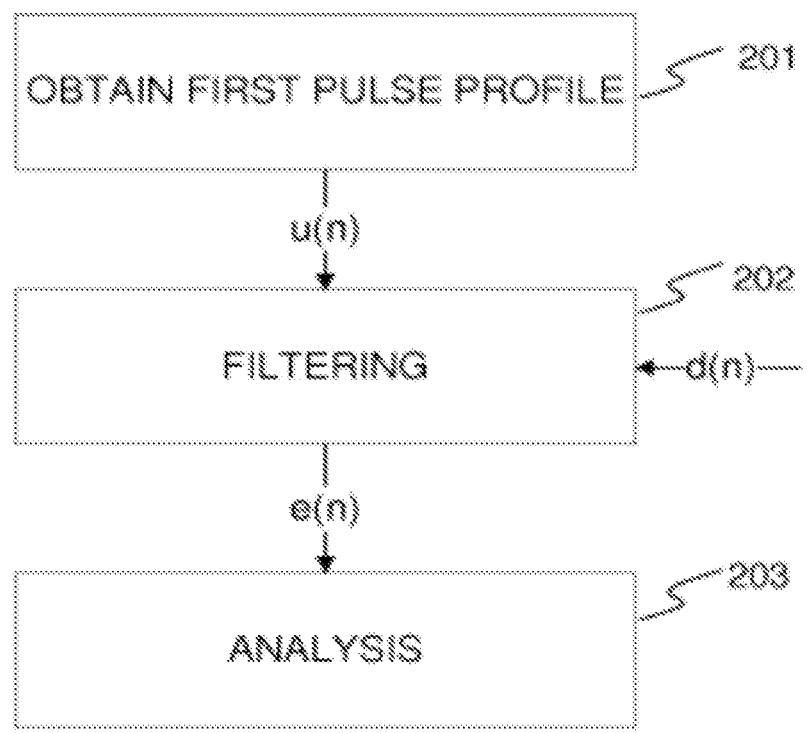
FIG. 15 is a flow chart of a monitoring process according to an embodiment of the invention.

Reverting to FIG. 15, the inventive data processing comprises two main steps: a determination of the first pulse profile u(n) (step 201) and a removal of one or more first pulses from a measurement signal d(n) using the first pulse profile u(n) (step 202).

There are many ways to implement these main steps. For example, the first pulse profile (standard signal profile) may be obtained in a reference measurement, based on a measurement signal from one or more of the pressure sensors 4a-4c in the first subsystem S1, suitably by identifying and possibly averaging a set of first pulse segments in the measurement signal(s). The first pulse profile may or may not be updated intermittently during the actual monitoring of the aforesaid functional state or parameter. Alternatively, a predetermined (i.e. predefined) standard signal profile may be used, which optionally may be modified according to a mathematical model accounting for wear in the first pulse generator, fluid flow rates, tubing dimensions, speed of sound in the fluid, etc. Further, the removal may involve subtracting the first pulse profile from the measurement signal at suitable amplitude and phase. The phase may be indicated by phase information which may be obtained from a signal generated by a phase sensor coupled to the first pulse generator 3, or from a control signal for the first pulse generator 3.

The inventive filtering may also be combined with other filtering techniques to further improve the quality of the filtered signal e(n). In one embodiment, the filtered signal e(n) may be passed through a bandpass filter with a passband in the relevant frequency range for the second pulses. If the second pulses originate from a human heart, the passband may be located within the approximate range of 0.5-4 Hz, corresponding to heart pulse rates of 30-240 beats per minute. In another embodiment, if the current frequency range (or ranges) of the second pulses is known, the passband of the bandpass filter may be actively controlled to a narrow range around the current frequency range. For example, such an active control may be applied whenever the rates of first and second pulses are found to differ by more than a certain limit, e.g. about 10%. The current frequency range may be obtained from the pressure signal, either by intermittently shutting off the first pulse generator 3, or intermittently preventing the first pulses from reaching the relevant pressure sensor 4a-4c. Alternatively, the current frequency range may be obtained from a dedicated sensor in either the first or the second sub-systems S1, S2, or based on a control unit (not shown) for the second pulse generator 3'. According to yet another alternative, the location and/or width of the passband may be set, at least in part, based on patient-specific information, i.e. existing data records for the patient, e.g. obtained in earlier treatments of the same patient. The patient-specific information may be stored in an internal memory (cf. 30 in FIG. 1) of the surveillance device, on an external memory which is made accessible to the surveillance device, or on a patient card where the information is e.g. transmitted wirelessly to the surveillance device, e.g. by RFID (Radio Frequency IDentification).

These and other embodiments will be explained in further detail below, within the context of a system for extracorporeal blood treatment. To facilitate the following discussion, details of an exemplifying extracorporeal blood flow circuit will be first described.

Monitoring in an Extracorporeal Blood Flow Circuit

Figure 17:
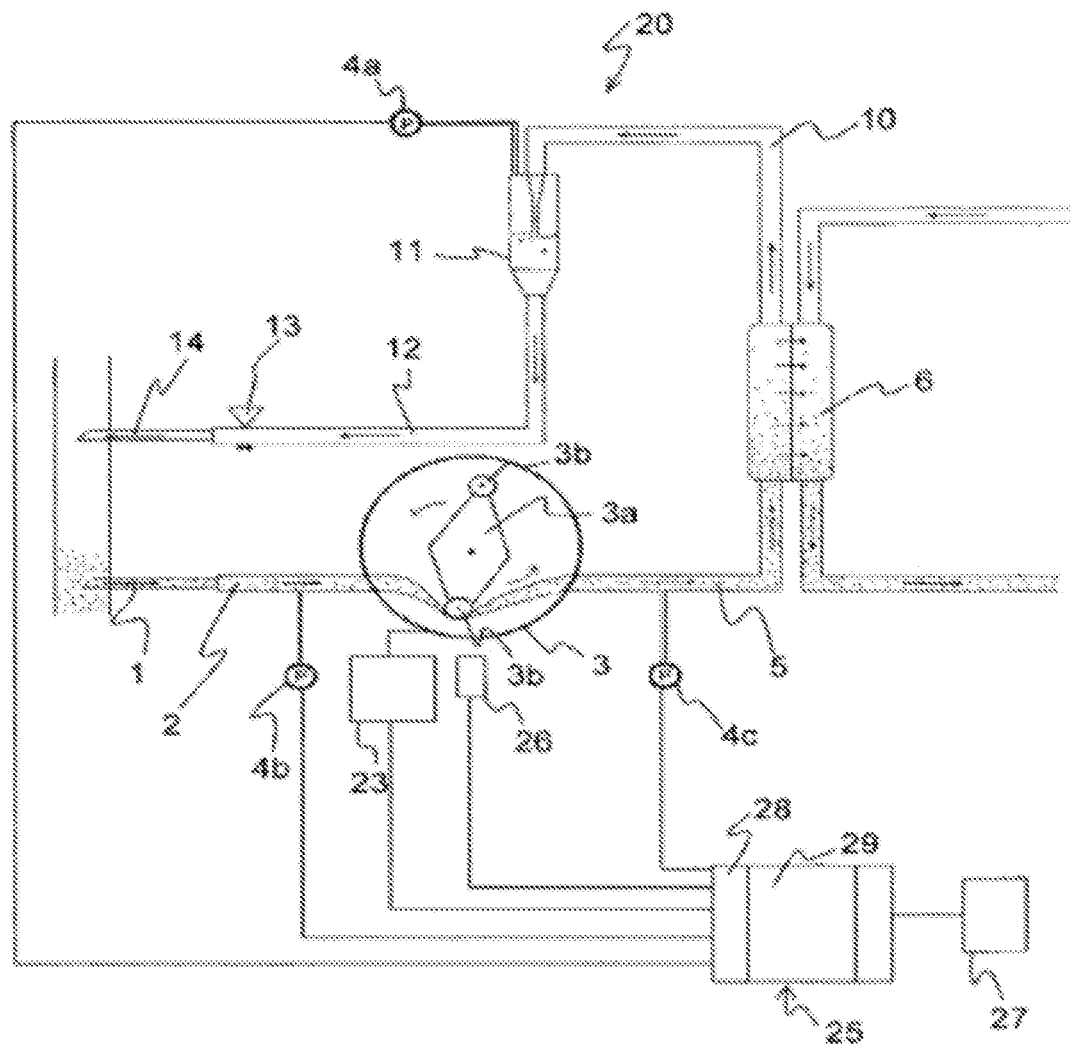
FIG. 17 is a schematic view of a system for hemodialysis treatment including an extracorporeal blood flow circuit.

FIG. 17 shows an example of an extracorporeal blood flow circuit 20 of the type which is used for dialysis. The extracorporeal blood flow circuit 20 (also denoted "extracorporeal circuit") comprises components 1-14 to be described in the following. Thus, the extracorporeal circuit 20 comprises an access device for blood extraction in the form of an arterial needle 1, and an arterial tube segment 2 which connects the arterial needle 1 to a blood pump 3 which may be of peristaltic type, as indicated in FIG. 17. At the inlet of the pump there is a pressure sensor 4b (hereafter referred to as "arterial sensor") which measures the pressure before the pump in the arterial tube segment 2. The blood pump 3 forces the blood, via a tube segment 5, to the blood-side of a dialyser 6. Many dialysis machines are additionally provided with a pressure sensor 4c (hereafter referred to as "system sensor") that measures the pressure between the blood pump 3 and the dialyser 6. The blood is lead via a tube segment 10 from the blood-side of the dialyser 6 to a venous drip chamber or deaeration chamber 11 and from there back to the patient via a venous tube segment 12 and an access device for blood reintroduction in the form of a venous needle 14. A pressure sensor 4a (hereafter referred to as "venous sensor") is provided to measure the pressure on the venous side of the dialyser 6. In the illustrated example, the pressure sensor 4a measures the pressure in the venous drip chamber. Both the arterial needle 1 and the venous needle 14 are connected to the patient by means of a blood vessel access. The blood vessel access may be of any suitable type, e.g. a fistula, a Scribner-shunt, a graft, etc. Depending on the type of blood vessel access, other types of access devices may be used instead of needles, e.g. catheters. The access devices 1, 14 may alternatively be combined into a single unit.

In relation to the fluid containing system in FIG. 14, the extracorporeal circuit 20 corresponds to the first sub-system S1, the blood pump 3 (as well as any further pulse source(s) within or associated with the extracorporeal circuit 20, such as a dialysis solution pump, valves, etc) corresponds to the first pulse generator 3, the blood system of the patient corresponds to the second sub-system S2, and the fluid connection C corresponds to at least one of the venous-side and arterial-side fluid connections between the patient and the extracorporeal circuit 20.

In FIG. 17, a control unit 23 is provided, i.a., to control the blood flow in the extracorporeal circuit 20 by controlling the revolution speed of the blood pump 3. The extracorporeal circuit 20 and the control unit 23 may form part of an apparatus for extracorporeal blood treatment, such as a dialysis machine. Although not shown or discussed further it is to be understood that such an apparatus performs many other functions, e.g. controlling the flow of dialysis fluid, controlling the temperature and composition of the dialysis fluid, etc.

The system in FIG. 17 also includes a surveillance/monitoring device 25, which is connected to receive a pressure signal from at least one of the pressure sensors 4a-4c and which executes the inventive data processing. In the example of FIG. 17, the surveillance device 25 is also connected to the control unit 23. Alternatively or additionally, the device 25 may be connected to a pump sensor 26 for indicating the revolution speed and/or phase of the blood pump 3. It is to be understood that the surveillance device 25 may include inputs for further data, e.g. any other system parameters that represent the overall system state (see e.g. discussion with reference to FIG. 20 below). The device 25 is tethered or wirelessly connected to a local or remote device 27 for generating an audible/visual/tactile alarm or warning signal. Alternatively or additionally, either device 25, 27 may include a display or monitor for displaying the functional state or parameter resulting from the analysis step (203 in FIG. 15), and/or the filtered signal e(n) resulting from the filtering step (202 in FIG. 15), e.g. for visual inspection.

In FIG. 17, the surveillance device 25 comprises a data acquisition part 28 for pre-processing the incoming signal(s), e.g. including an A/D converter with a required minimum sampling rate and resolution, one or more signal amplifiers, and one or more filters to remove undesired components of the incoming signal(s), such as offset, high frequency noise and supply voltage disturbances.

Figure 18A:
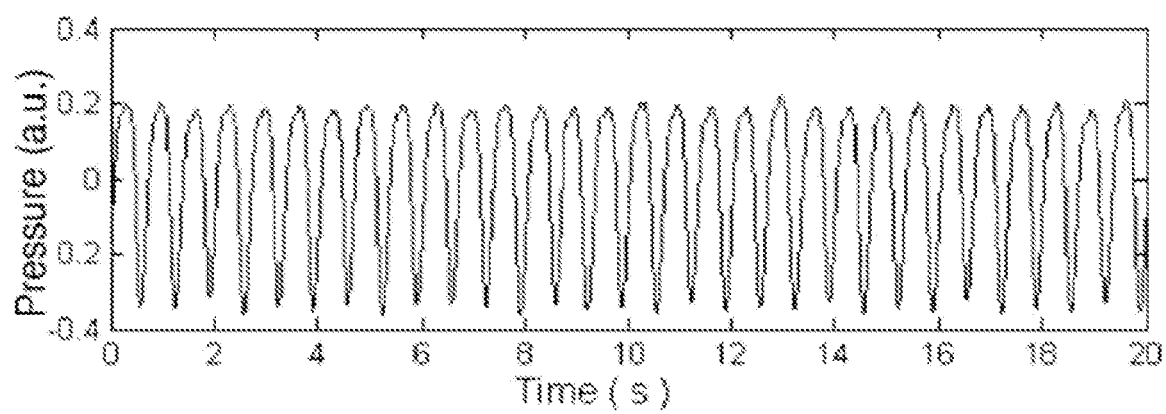
FIG. 18A is a plot in the time domain of a venous pressure signal containing both pump frequency components and a heart signal.
Figure 18B:
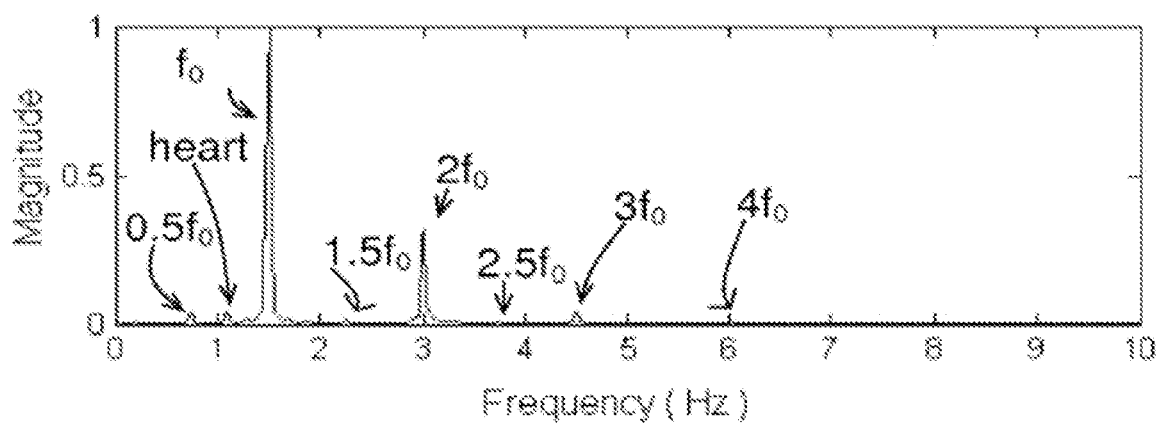
FIG. 18B is a plot of the corresponding signal in the frequency domain.

After the pre-processing in the data acquisition part 28, the pre-processed pressure signal is provided as input to a main data processing part 29, which executes the inventive data processing. FIG. 18A shows an example of such a pre-processed pressure signal in the time domain, and FIG. 18B shows the corresponding power spectrum, i.e. the pre-processed pressure signal in the frequency domain. The power spectrum reveals that the detected pressure signal contains a number of different frequency components emanating from the blood pump 3. In the illustrated example, there is a frequency component at the base frequency ($f_0$) of the blood pump (at 1.5 Hz in this example), as well as its harmonics $2f_0$, $3f_0$ and $4f_0$. The base frequency, also denoted pump frequency in the following, is the frequency of the pump strokes that generate pressure waves in the extracorporeal circuit 20. For example, in a peristaltic pump of the type shown in FIG. 17, two pump strokes are generated for each full revolution of the rotor 3a. FIG. 18B also indicates the presence of a frequency component at half the pump frequency ($0.5f_0$) and harmonics thereof, in this example at least $f_0$, $1.5f_0$, $2f_0$ and $2.5f_0$. FIG. 18B also shows a heart signal (at 1.1 Hz) which in this example is approximately 40 times weaker than the blood pump signal at the base frequency $f_0$.

The main data processing part 29 executes the aforesaid steps 201-203. In step 202, the main data processing part 29 operates to filter the pre-processed pressure signal in the time domain, and outputs a filtered signal or monitoring signal (e(n) in FIG. 15) in which the signal components of the blood pump 3 have been removed. The monitoring signal still contains any signal components that originate from the patient (cf. FIG. 16B), such as pressure pulses caused by the beating of the patient's heart. There are a number of sources to cyclic physiological phenomena that may generate pressure pulses in the blood stream of the patient, including the heart, the breathing system, or the vasomotor, which is controlled by the autonomic nervous system. Thus, the monitoring signal may contain pressure pulses resulting from a combination of cyclic phenomena in the patient. Generally speaking, the signal components in the monitoring signal may originate from any type of physiological phenomenon in the patient, or combinations thereof, be it cyclic or non-cyclic, repetitive or non-repetitive, autonomous or non-autonomous.

Depending on implementation, the surveillance device 25 may be configured apply further filtering to the monitoring signal to isolate signal components originating from a single cyclic phenomenon in the patient. Alternatively, such signal component filtering is done during the pre-processing of the pressure signal (by the data acquisition part 28). The signal component filtering may be done in the frequency domain, e.g. by applying a cut-off or bandpass filter, since the signal components of the different cyclic phenomena in the patient are typically separated in the frequency domain. Generally, the heart frequency is about 0.5-4 Hz, the breathing frequency is about 0.15-0.4 Hz, the frequency of the autonomous system for regulation of blood pressure is about 0.04-0.14 Hz, the frequency of the autonomous system for regulation of body temperature is about 0.04 Hz.

The surveillance device 25 may be configured to monitor the breathing pattern of the patient, by identifying breathing pulses in the monitoring signal. The resulting information may be used for on-line surveillance for apnoea, hyperventilation, hypoventilation, asthmatic attacks or other irregular breathing behaviours of the patient. The resulting information may also be used to identify coughing, sneezing, vomiting or seizures. The vibrations resulting from coughing/sneezing/vomiting/seizures might disturb other measurement or surveillance equipment that is connected to the patient or the extracorporeal circuit 20. The surveillance device 25 may be arranged to output information about the timing of any coughing/sneezing/vomiting/seizures, such that other measurement or surveillance equipment may take adequate measures to reduce the likelihood that the coughing/sneezing/vomiting/seizures results in erroneous measurements or false alarms. Of course, the ability of identifying coughing/sneezing/vomiting/seizures may also have a medical interest of its own.

The surveillance device 25 may be configured to monitor the heart rate of the patient, by identifying heart pulses in the monitoring signal.

The surveillance device 25 may be configured to collect and store data on the time evolution of the heart rate, the breathing pattern, etc, e.g. for subsequent trending or statistical analysis.

The surveillance device 25 may be configured to monitor the integrity of the fluid connection between the patient and the extracorporeal circuit 20, in particular the venous-side fluid connection (via access device 14). This may be done by monitoring the presence of a signal component originating from, e.g., the patient's heart or breathing system in the monitoring signal. Absence of such a signal component may be taken as an indication of a failure in the integrity of the fluid connection C, and may bring the device 25 to activate an alarm and/or stop the blood flow, e.g. by stopping the blood pump 3 and activating a clamping device 13 on the tube segment 12. For monitoring the integrity of the venous-side fluid connection, also known as VNM (Venous Needle Monitoring), the surveillance device 25 may be configured to generate the monitoring signal based on a pressure signal from the venous sensor 4a. The device 25 may also be connected to pressure sensors 4b, 4c, as well as any additional pressure sensors included in the extracorporeal circuit 20.

The extracorporeal circuit 20 may have the option to operate in a hemodiafiltration mode (HDF mode), in which the control unit 23 activates a second pumping device (HDF pump, not shown) to supply an infusion solution into the blood line upstream and/or downstream of the dialyser 6, e.g. into one or more of tube segments 2, 5, 10 or 12.

Obtaining the Predicted Signal Profile of First Pulses

This section describes different embodiments for predicting or estimating the signal profile of first pulses in the system shown in FIG. 17. The predicted signal profile is typically given as a series of pressure values over a period of time normally corresponding to at least one complete pump cycle of the blood pump 3.

Figure 19:
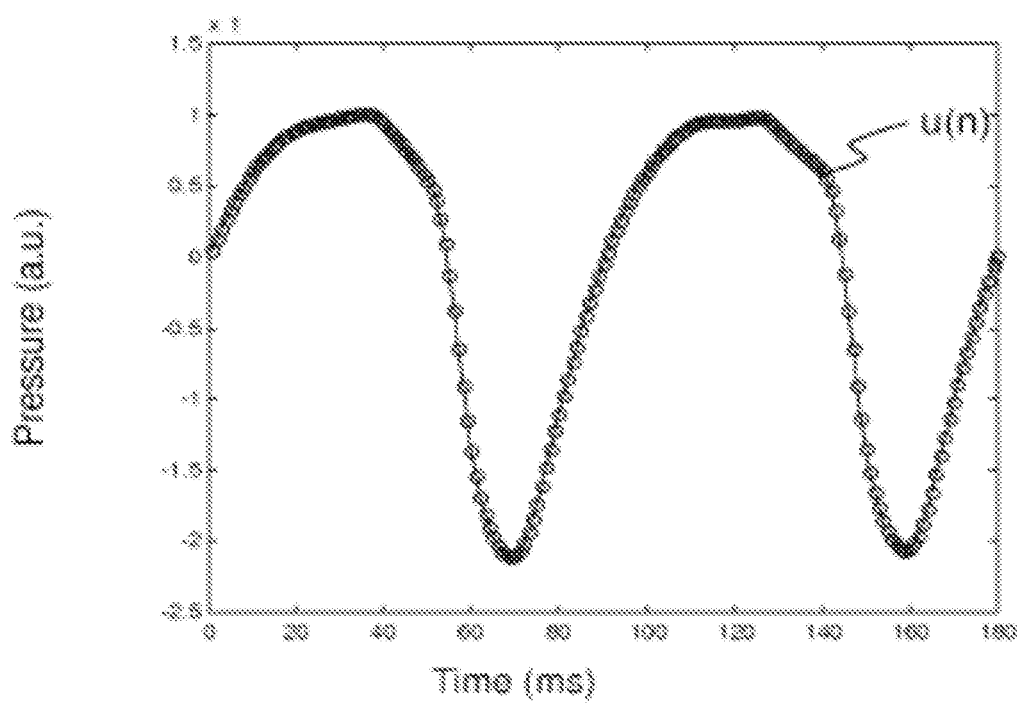
FIG. 19 is a plot of a predicted signal profile originating from a peristaltic pump in the system of FIG. 17.

FIG. 19 illustrates an example of a predicted signal profile for the system in FIG. 17. Since the blood pump 3 is a peristaltic pump, in which two rollers 3b engage a tube segment during a full revolution of the rotor 3a, the pressure profile consists of two pump strokes. The pump strokes may result in different pressure values (pressure profiles), e.g. due to slight differences in the engagement between the rollers 3b and the tube segment, and thus it may be desirable for the predicted signal profile to represent both pump strokes. If a lower accuracy of the predicted signal profile may be tolerated, i.e. if the output of the subsequent removal process is acceptable, the predicted signal profile might represent one pump stroke only.

On a general level, the predicted signal profile may be obtained in a reference measurement, through mathematical simulation of the fluid system, or combinations thereof.

Reference Measurement

A first main group of methods for obtaining the predicted signal profile is based on deriving a time-dependent reference pressure signal ("reference signal") from a pressure sensor in the system, typically (but not necessarily) from the same pressure sensor that provides the measurement signal (pressure signal) that is to be processed for removal of first pulses. During this reference measurement, the second pulses are prevented from reaching the relevant pressure sensor, either by shutting down/deactivating the second pulse generator 3' or by isolating the pressure sensor from the second pulses. In the system of FIG. 17, the reference measurement may be carried out during a priming phase, in which the extracorporeal circuit 20 is detached from the patient and a priming fluid is pumped through the blood lines. Alternatively, the reference measurement may be carried in a simulated treatment with blood or any other fluid. Optionally, the reference measurement may involve averaging a plurality of pressure profiles to reduce noise. For example, a plurality of relevant signal segments may be identified in the reference signal, whereupon these segments are aligned to achieve a proper overlap of the pressure profiles in the different segments and then added together. The identifying of relevant signal segments may be at least partially based on timing information which indicates the expected position of each first pulse in the reference signal. The timing information may be obtained from a trigger point in the output signal of the pump sensor 26, in a control signal of the control unit 23, or in the pressure signal from another one of the pressure sensors 4a-4c. For example, a predicted time point of a first pulse in the reference signal may be calculated based on a known difference in arrival time between the trigger point and the pressure sensor that generates the reference signal. In variant, if the reference signal is periodic, relevant signal segments may be identified by identifying crossing points of the reference signal with a given signal level, wherein the relevant signal segments are identified to extend between any respective pairs of crossing points.

In a first embodiment, the predicted signal profile is directly obtained in a reference measurement before the extracorporeal circuit 20 is connected to the patient, and is then used as input to the subsequent removal process, which is executed when the extracorporeal circuit 20 is connected to the patient. In this embodiment, it is thus assumed that the predicted signal profile is representative of the first pulses when the system is connected to the patient. Suitably, the same pump frequency/speed is used during the reference measurement and during the removal process. It is also desirable that other relevant system parameters are maintained essentially constant.

Figure 20:
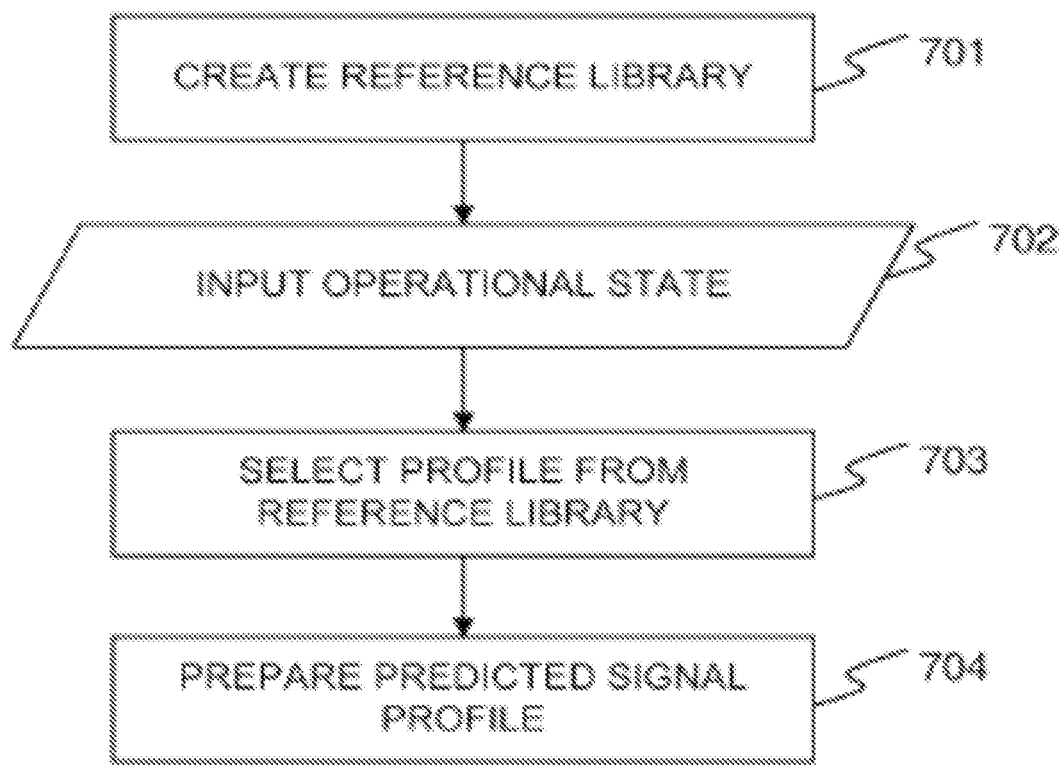
FIG. 20 is a flow chart of a process for obtaining the predicted signal profile.

FIG. 20 is a flow chart of a second embodiment. In the second embodiment, a reference library or database is first created based on the reference measurement (step 701). The resulting reference library is typically stored in a memory unit, e.g. RAM, ROM, EPROM, HDD, Flash, etc (cf. 25b in FIG. 14) of the surveillance device (cf. 25 in FIG. 14). During the reference measurement, reference pressure signals are acquired for a number of different operational states of the extracorporeal circuit. Each operational state is represented by a unique combination of system parameter values. For each operational state, a reference profile is generated to represent the signal profile of the first pulses. The reference profiles together with associated system parameter values are then stored in the reference library, which is implemented as a searchable data structure, such as a list, look-up table, search tree, etc.

During the actual monitoring process, i.e. when first pulses are to be eliminated from the measurement signal, current state information indicating the current operational state of the fluid containing system is obtained from the system, e.g. from a sensor, a control unit or otherwise (step 702). The current state information may include a current value of one or more system parameters. The current value is then matched against the system parameter values in the reference library. Based on the matching, one or more reference profiles are selected (step 703) and used for preparing the predicted signal profile (step 704).

Generally, the aforesaid system parameters represent the overall system state, including but not limited to the structure, settings, status and variables of the fluid containing system or its components. In the system of FIG. 17, exemplary system parameters may include:

Pump-related parameters: number of active pumps connected directly or indirectly (e.g. in a fluid preparation system for the dialyser) to the extracorporeal circuit, type of pumps used (roller pump, membrane pump, etc), flow rate, revolution speed of pumps, shaft position of pump actuator (e.g. angular or linear position), etc Dialysis machine settings: temperature, ultrafiltration rate, mode changes, valve position/changes, etc Disposable dialysis equipment/material: information on pump chamber/pump segment (material, geometry and wear status), type of blood line (material and geometry), type of dialyser, type and geometry of access devices, etc Dialysis system variables: actual absolute pressures of the system upstream and downstream of the blood pump, e.g. venous pressure (from sensor 4a), arterial pressure (from sensor 4b) and system pressure (from sensor 4c), gas volumes trapped in the flow path, blood line suspension, fluid type (e.g. blood or dialysis fluid), etc Patient status: blood access properties, blood properties such as e.g. hematocrit, plasma protein concentration, etc It is to be understood that any number or combination of system parameters may be stored in the reference library and/or used as search variables in the reference library during the monitoring process.

In the following, the second embodiment will be further explained in relation to a number of examples. In all of these examples, the pump revolution frequency ("pump frequency"), or a related parameter (e.g. blood flow rate) is used to indicate the current operational state of the fluid containing system during the monitoring process. In other words, the pump frequency is used as search variable in the reference library. The pump frequency may e.g. be given by a set value for the blood flow rate output from the control unit, or by an output signal of a sensor that indicates the frequency of the pump (cf. pump sensor 26 in FIG. 17). Alternatively, the pump frequency may be obtained by frequency analysis of the pressure signal from any of the sensors 4a-4c during operation of the fluid system. Such frequency analysis may be achieved by applying any form of harmonics analysis to the pressure signal, such as Fourier or wavelet analysis. As indicated in FIG. 18B, the base frequency $f_0$ of the pump may be identified in a resulting power spectrum.

Figure 21:
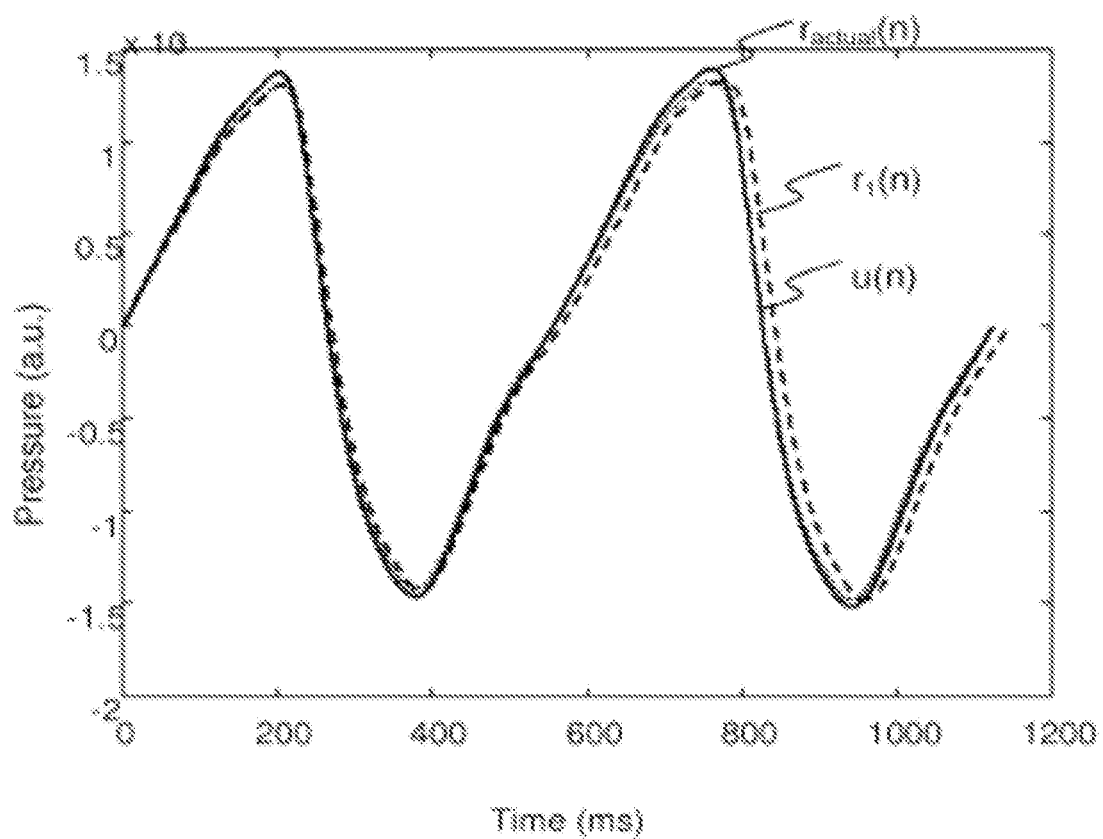
FIG. 21 is a plot to illustrate an extrapolation process for generating the predicted signal profile.

In a first example, the reference library is searched for retrieval of the reference profile that is associated with the pump frequency that lies closest to the current pump frequency. If no exact match is found to the current pump frequency, an extrapolation process is executed to generate the predicted signal profile. In the extrapolation process, the retrieved reference profile is scaled in time to the current pump cycle, based on the known difference ("pump frequency difference") between the current pump frequency and the pump frequency associated with the retrieved reference profile. The amplitude scale may also be adjusted to compensate for amplitude changes due to pump frequency, e.g. based on a known function of amplitude as a function of pump frequency. FIG. 21 illustrates a reference profile $r_1(n)$ obtained at a flow rate of 470 ml/min, and predicted signal profile u(n) which is obtained by scaling the reference profile to a flow rate of 480 ml/min. For comparison only, a reference profile $r_{actual}(n)$ obtained at 480 ml/min is also shown, to illustrate that extrapolation process indeed may yield a properly predicted signal profile.

In a second example, the reference library is again searched based on current pump frequency. If no exact match is found to the current pump frequency, a combination process is executed to generate the predicted signal profile. Here, the reference profiles associated with the two closest matching pump frequencies are retrieved and combined. The combination may be done by re-scaling the pump cycle time of the retrieved reference profiles to the current pump frequency and by calculating the predicted signal profile via interpolation of the re-scaled reference profiles. For example, the predicted signal profile u(n) at the current pump frequency v may be given by:

$$u(n)=g(v-v_i)\cdot r_i(n)+(1-g(v-v_i))\cdot r_j(n),$$

wherein $r_i(n)$ and $r_j(n)$ denotes the two retrieved reference profiles, obtained at a pump frequency $v_i$ and $v_j$, respectively, after re-scaling to the current pump frequency v, and g is a relaxation parameter which is given as a function of the frequency difference $(v-v_i)$, wherein $v_i \leq v \leq v_j$ and $0 \leq g \leq 1$. The skilled person realizes that the predicted signal profile u(n) may be generated by combining more than two reference profiles.

Figure 22A:
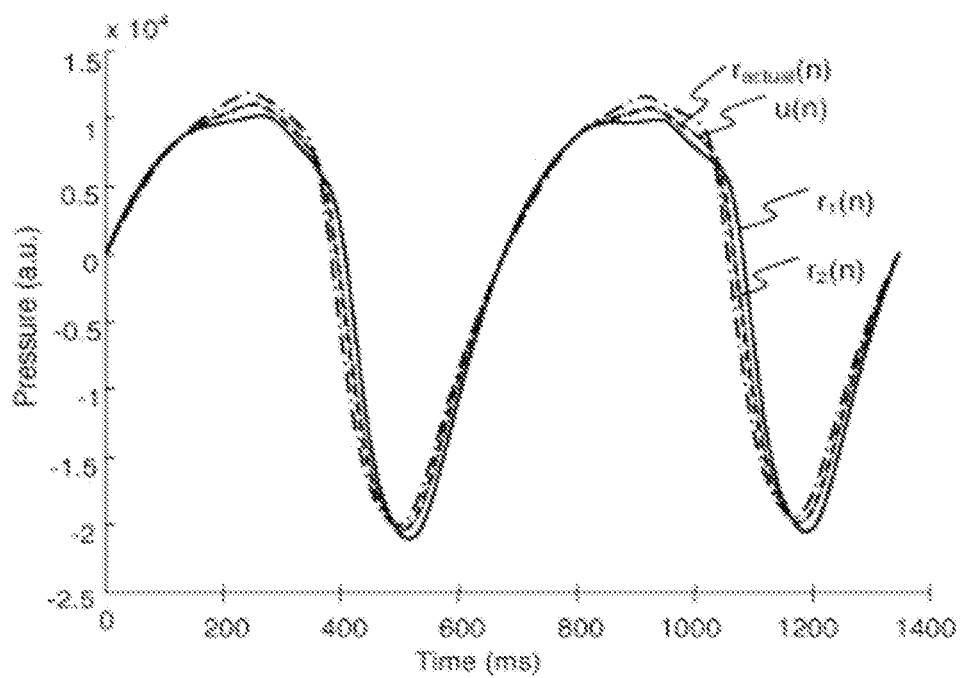
FIG. 22A is a plot to illustrate an interpolation process for generating the predicted signal profile.
Figure 22B:
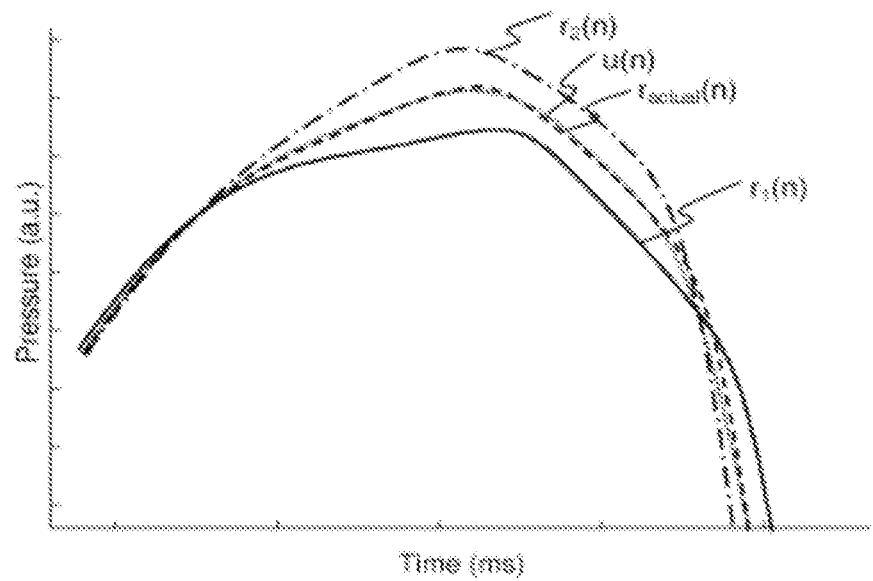
FIG. 22B is an enlarged view of FIG. 22A.

FIG. 22A illustrates a predicted signal profile u(n) at a current flow rate of 320 ml/min for a measurement signal obtained from the venous sensor 4a in the system of FIG. 17. The predicted signal profile u(n) has been calculated as an average of a reference profile $r_1(n)$ obtained at a flow rate of 300 ml/min from the venous sensor and a reference profile $r_2(n)$ obtained at a flow rate of 340 ml/min from the venous sensor. For comparison only, a reference profile $r_{actual}(n)$ obtained at 320 ml/min is also shown, to illustrate that the combination process indeed may yield a properly predicted signal profile. In fact, the differences are so small that they are only barely visible in the enlarged view of FIG. 22B.

The first and second examples may be combined, e.g. by executing the extrapolation process of the first example if the pump frequency difference is less than a certain limit, and otherwise executing the combination process of the second example.

In a third embodiment, like in the second embodiment shown in FIG. 20, a number of reference signals are acquired in the reference measurement, wherein each reference signal is obtained for a specific combination of system parameter values. The reference signals are then processed for generation of reference spectra, which are indicative of the energy and phase angle as function of frequency. These reference spectra may e.g. be obtained by Fourier analysis, or equivalent, of the reference signals. Corresponding energy and phase data are then stored in a reference library together with the associated system parameter values (cf. step 701 in FIG. 20). The implementation of the reference library may be the same as in the second embodiment.

During the actual monitoring process, i.e. when first pulses are to be eliminated from the measurement signal, a current value of one or more system parameters is obtained from the fluid containing system (cf. step 702 in FIG. 20). The current value is then matched against the system parameter values in the reference library. Based on the matching, a specific set of energy and phase data may be retrieved from the reference library to be used for generating the predicted signal profile (cf. step 703 in FIG. 20). Generally, the predicted signal profile is generated by adding sinusoids of appropriate frequency, amplitude and phase, according to the retrieved energy and phase data (cf. step 704 in FIG. 20).

Generally speaking, without limiting the present disclosure, it may be advantageous to generate the predicted signal profile from energy and phase data when the first pulses (to be removed) contain only one or a few base frequencies (and harmonics thereof), since the predicted signal profile may be represented by a small data set (containing energy and phase data for the base frequencies and the harmonics). One the other hand, when the power spectrum of the first pulses is more complex, e.g. a mixture of many base frequencies, it may instead be preferable to generate the predicted signal profile from one or more reference profiles.

Figure 23A:
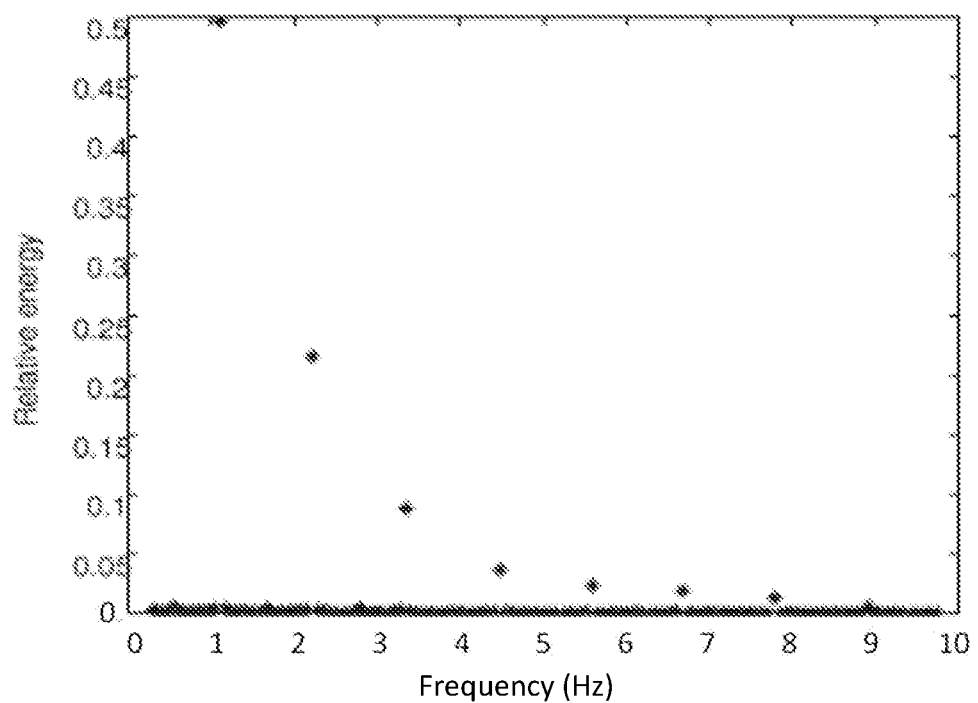
FIG. 23A represents a frequency spectrum of a pressure pulse originating from a pumping device at one flow rate.
Figure 23B:
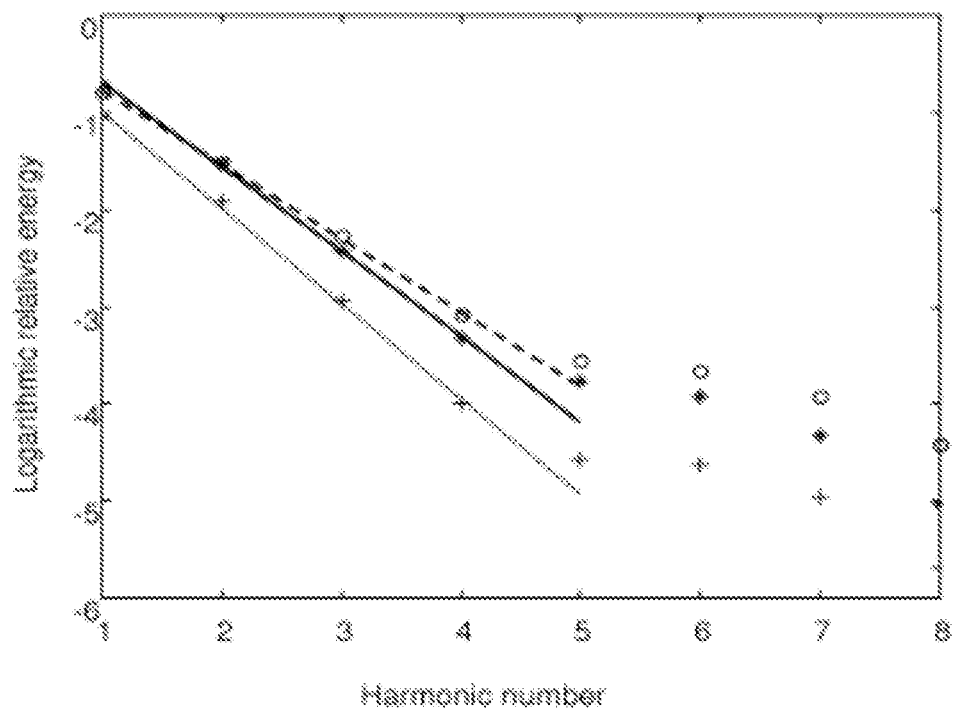
FIG. 23B represents corresponding frequency spectra for three different flow rates, wherein each frequency spectrum is given in logarithmic scale and mapped to harmonic numbers.
Figure 23C:
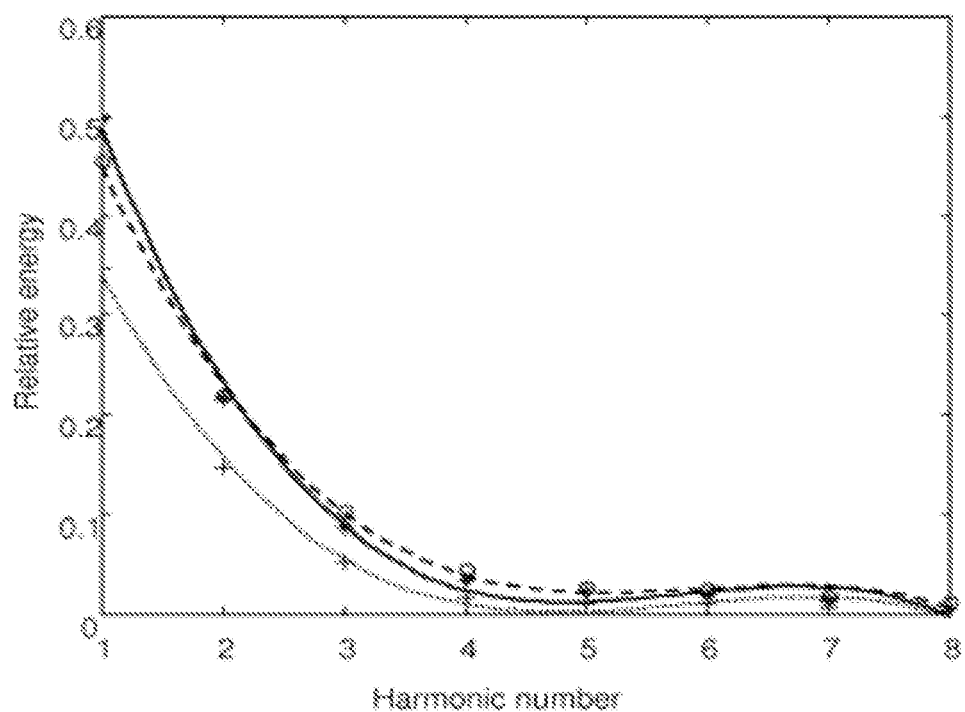
FIG. 23C is a plot of the data in FIG. 23B in linear scale.

FIG. 23A represents an energy spectrum of a reference signal acquired at a flow rate of 300 ml/min in the system of FIG. 17. In this example, the reference signal essentially consists of a basic pump frequency at 1.2 Hz ($f_0$, first harmonic) and a set of overtones of this frequency (second and further harmonics). Compared to the power spectrum of FIG. 18B, the pressure signals used for generating the graphs in FIG. 23A-23D do not contain any significant frequency component at $0.5f_0$ and its harmonics. The graph in FIG. 23A displays the relative energy distribution, wherein the energy values have been normalized to the total energy for frequencies in the range of 0-10 Hz. FIG. 23B represents energy spectra of reference signals acquired at three different flow rates in the system of FIG. 17. The energy spectra are given in logarithmic scale versus harmonic number (first, second, etc). As shown, an approximate linear relationship may be identified between the logarithmic energy and harmonic number for the first four to five harmonic numbers. This indicates that each energy spectrum may be represented by a respective exponential function. FIG. 23C illustrates the data of FIG. 23B in linear scale, wherein a respective polynomial function has been fitted to the data. As indicated in FIGS. 23A-23C, the energy spectra may be represented in different formats in the reference library, e.g. as a set of energy values associated with discrete frequency values or harmonic numbers, or as an energy function representing energy versus frequency/harmonic number.

Figure 23D:
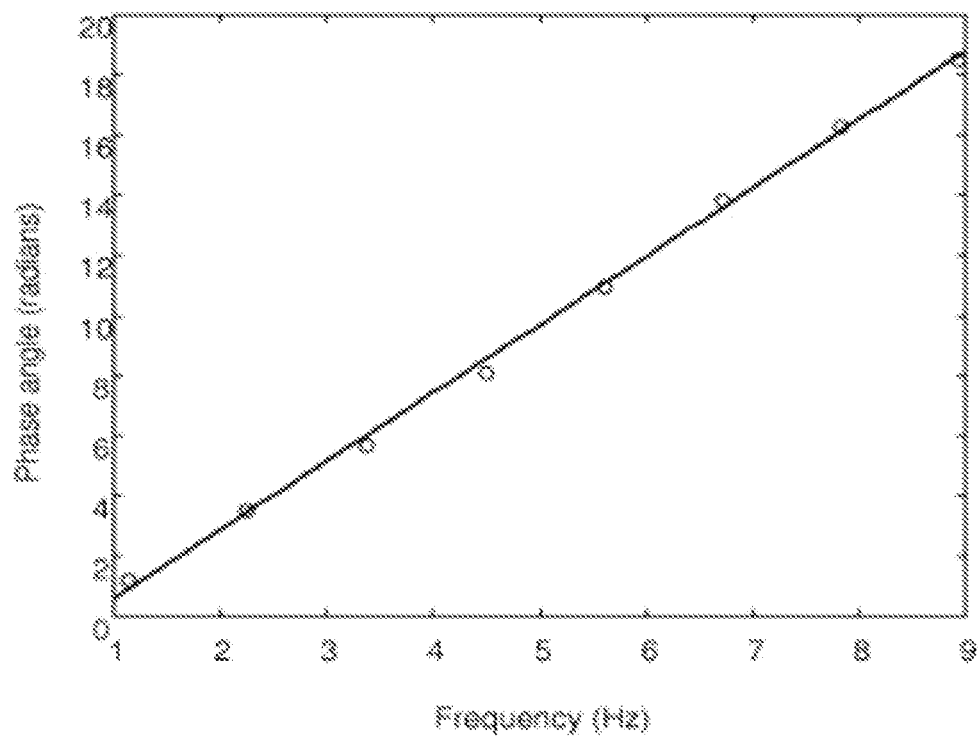
FIG. 23D is a phase angle spectrum corresponding to the frequency spectrum in FIG. 23A.

FIG. 23D illustrates a phase angle spectrum acquired together with the energy spectrum in FIG. 23A, i.e. for a flow rate of 300 ml/min. The graph in FIG. 23D illustrates phase angle as a function of frequency, and a linear function has been fitted to the data. In an alternative representation (not shown), the phase spectrum may be given as a function of harmonic number. Like the energy spectra, the phase spectra may be represented in different formats in the reference library, e.g. as a set of phase angle values associated with discrete frequency values or harmonic numbers, or as a phase function representing phase angle versus frequency/harmonic number.

From the above, it should be understood that the energy and phase data that are stored the reference library may be used to generate the predicted signal profile. Each energy value in the energy data corresponds to an amplitude of a sinusoid with a given frequency (the frequency associated with the energy value), wherein the phase value for the given frequency indicates the proper phase angle of the sinousoid. This method of preparing the predicted signal profile by combining (typically adding) sinusoids of appropriate frequency, amplitude and phase angle allows the predicted signal profile to include all harmonics of the pump frequency within a desired frequency range.

When a predicted signal profile is to be generated, the reference library is first searched based on a current value of one or more system parameters, such as the current pump frequency. If no exact match is found in the reference library, a combination process may be executed to generate the predicted signal profile. For example, the two closest matching pump frequencies may be identified in the reference library and the associated energy and phase data may be retrieved and combined to form the predicted signal profile. The combination may be done by interpolating the energy data and the phase data. In the example of FIGS. 23A-23D, an interpolated energy value may be calculated for each harmonic number, and similarly an interpolated phase value may be calculated for each harmonic number. Any type of interpolation function may be used, be it linear or non-linear.

In the first, second and third embodiments, the reference signals and the measurement signals are suitably obtained from the same pressure sensor unit in the fluid containing system. Alternatively, different pressure sensor units may be used, provided that the pressure sensor units yield identical signal responses with respect to the first pulses or that the signal responses may be matched using a known mathematical relationship.

To further improve the first, second and third embodiments, the process of generating the predicted signal profile may also involve compensating for other potentially relevant factors that differ between the reference measurement and the current operational state. These so-called confounding factors may comprise one or more of the system parameters listed above, such as absolute average venous and arterial pressures, temperature, blood hematocrit/viscosity, gas volumes, etc. This compensation may be done with the use of predefined compensation formulas or lookup tables.

In further variations, the second and third embodiments may be combined, e.g. in that the reference library stores not only energy and phase data, but also reference profiles, in association with system parameter value(s). When an exact match is found in the library, the reference profile is retrieved from the library and used as the predicted signal profile, otherwise the predicted signal profile is obtained by retrieving and combining (e.g. interpolating) the energy and phase data, as in the third embodiment. In a variant, the predicted signal profile u(n) at the current pump frequency v is obtained by:

$$u(n) = r_i(n) - r^r_i(n) + r^r(n),$$

wherein $r_i(n)$ denotes a reference profile that is associated with the closest matching pump frequency $v_i$ in the reference library, $r^r_i(n)$ denotes a reference profile that is reconstructed from the energy and phase data associated with the closest matching pump frequency $v_i$ in the reference library, and $r^r(n)$ denotes an estimated reference profile at the current pump frequency v. The estimated reference profile $r^r(n)$ may be obtained by applying predetermined functions to estimate the energy and phase data, respectively, at the current pump frequency v based on the energy and phase data associated with the closest matching pump frequency $v_i$. With reference to FIGS. 23B-23C, such a predetermined function may thus represent the change in energy data between different flow rates. Alternatively, the estimated reference profile $r^r(n)$ may be obtained by retrieving and combining (e.g. interpolating) energy and phase data for the two closest matching pump frequencies $v_i$ and $v_j$ as in the third embodiment.

In a further variant, the reference measurement is made during regular operation of the fluid containing system, instead of or in addition to any reference measurements made before regular operation (e.g. during priming or simulated treatments with blood). Such a variant presumes that it is possible to intermittently shut off the second pulse generator, or to intermittently prevent the second pulses from reaching the relevant pressure sensor. This approach is more difficult in the extracorporeal circuit 20 of FIG. 17 if the reference signals and the measurement signals are obtained from the one and the same pressure sensor. However, this approach may e.g. be applied if the fluid system includes one pressure sensor that is substantially isolated from the second pulses. In such a situation, the reference profile (or reference spectra) may be obtained from the isolated sensor, and used for generating the predicted signal profile (optionally after adjustment/modification for differences in confounding factors), which is then used for removing first pulses from a measurement signal that contains both first and second pulses. For example, the pressure signal from the system sensor 4c in the circuit 20 of FIG. 17 may be essentially isolated from the second pulses that originate from the patient, and this pressure signal may thus be used in a reference measurement.

As explained above, the extracorporeal circuit 20 in FIG. 17 may be switched into a HDF mode, in which an additional HDF pump is activated to supply an infusion liquid into the blood line of the extracorporeal circuit 20. Such a change of operating mode may cause a change in the signal characteristics of the first pulses in the measurement signal. Thus, it may necessary to account for this change, by ensuring that the reference library includes appropriate reference data (reference profiles and/or energy and phase angle data) associated with this operational state.

Alternatively, it may be desirable to isolate the pressure pulses originating from the HDF pump. This may be achieved by obtaining a reference profile from the pressure signal of the arterial sensor 4b (FIG. 17). The arterial pressure signal includes pressure pulses originating from the patient and from the blood pump 3, whereas pressure pulses originating from the HDF pump are significantly damped by the patient and the blood pump 3, respectively, and thus barely reach the arterial sensor 4b. On the other hand, the pressure signals of the venous sensor 4a and the system sensor 4c contain pressure pulses originating from both the patient, the blood pump 3 and the HDF pump. Thus, the arterial pressure signal may be used for obtaining the predicted signal profile of the combined pressure pulses originating from the blood pump 3 and the patient as they should look in the pressure signal from the venous sensor 4a or the system sensor 4c. The predicted signal profile may then be used for isolating the pressure pulses originating from the HDF pump in the pressure signal from the venous sensor 4a or the system sensor 4c. In this example, the patient and the extracorporeal circuit 20 may be regarded as a first sub-system (S1 in FIG. 14) and the HDF pump and the associated infusion tubing may be regarded as a second sub-system (S2 in FIG. 14), which are connected via a fluid connection. Thus, in this example, the inventive data processing is not applied to isolate pulses originating from a cyclic physiological phenomenon in the patient, but pulses originating from another pump in the fluid system. It should be realized that in other arrangements, the reference profile may be obtained from the pressure signal of the venous sensor 4a (FIG. 17), and used for processing the pressure signal of the arterial sensor 4b or system sensor 4c.

Simulations

As an alternative to the use of reference measurements, the predicted signal profile may be obtained directly through simulations, i.e. calculations using a mathematical model of the fluid containing system, based on current state information indicating the current operational state of the system. Such current state information may include a current value of one or more of the above-mentioned system parameters. The model may be based on known physical relationships of the system components (or via an equivalent representation, e.g. by representing the system as an electrical circuit with fluid flow and pressure being given by electrical current and voltage, respectively). The model may be expressed, implicitly or explicitly, in analytical terms. Alternatively, a numerical model may be used. The model may be anything from a complete physical description of the system to a simple function. In one example, such a simple function may convert data on the instantaneous angular velocity of the pump rotor 3a to a predicted signal profile, using empirical or theoretical data. Such data on the instantaneous angular velocity might be obtained from the pump sensor 26 in FIG. 17.

In another embodiment, simulations are used to generate reference profiles for different operational states of the system. These reference profiles may then be stored in a reference library, which may be accessed and used in the same way as described above for the second and third embodiments. It is also to be understood that reference profiles (and/or corresponding energy and phase angle data) obtained by simulations may be stored together with reference profiles (and/or corresponding energy and phase angle data) obtained by reference measurement.

Removal of First Pulses

There are several different ways of removing one or more first pulses from the measurement signal, using the predicted signal profile. Here, two different removal processes will be described: Single Subtraction and Adaptive Filtering. Of course, the description of removal processes and their implementations is not comprehensive (neither of the different alternatives nor of the implementations), which is obvious to a person skilled in the art.

Depending on implementation, the predicted signal profile may be input to the removal process as is, or the predicted signal profile may be duplicated to construct an input signal of suitable length for the removal process.

Single Subtraction

In this removal process, a single predicted signal profile is subtracted from the measurement signal. The predicted signal profile may be shifted and scaled in time and scaled in amplitude in any way, e.g. to minimize the error of the removal. Different minimization criterions may be used for such an auto-scaling, e.g., minimizing the sum of the squared errors, or the sum of the absolute errors. Alternatively or additionally, the predicted signal profile is shifted in time based on timing information that indicates the expected timing of the first pulse(s) in the measurement signal. The timing information may be obtained in the same way as described above in relation to the averaging of pressure segments in the reference signal.

One potential limitation of this removal process is that the relationship between different frequencies in the predicted signal profile is always the same, since the process only shifts and scales the predicted signal profile. Thus, it is not possible to change the relationship between different harmonic frequencies, neither is it possible to use only some of the frequency content in the predicted signal profile and to suppress other frequencies. To overcome this limitation, adaptive filtering may be used since it uses a linear filter before subtraction, e.g. as described in the following.

Adaptive Filtering

Figure 24:
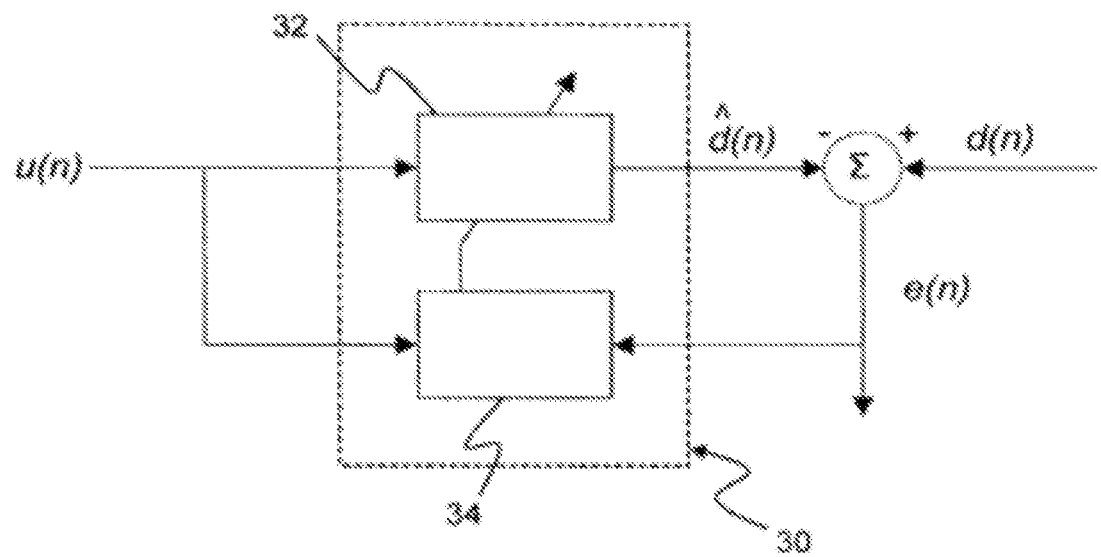
FIG. 24 is schematic view of an adaptive filter structure operable to filter a measurement signal based on a predicted signal profile.

FIG. 24 is a schematic overview of an adaptive filter 30 and an adaptive filter structure which is designed to receive the predicted signal profile u(n) and a measurement signal d(n), and to output an error signal e(n) which forms the aforesaid monitoring signal in which the first pulses are removed.

Adaptive filters are well-known electronic filters (digital or analog) that self-adjust their transfer function according to an optimizing algorithm. Specifically, the adaptive filter 30 includes a variable filter 32, typically a finite impulse response (FIR) filter of length M with filter coefficients w(n).

Even if adaptive filters are known in the art, they are not readily applicable to cancel the first pulses in the measurement signal d(n). In the illustrated embodiment, this has been achieved by inputting the predicted signal profile u(n)

to the variable filter 32, which processes the predicted signal profile u(n) to generate an estimated measurement signal d̂(n), and to an adaptive update algorithm 34, which calculates the filter coefficients of the variable filter 32 based on the predicted signal profile u(n) and the error signal e(n). The error signal e(n) is given by the difference between the measurement signal d(n) and the estimated measurement signal d̂(n).

Basically, the adaptive filtering also involves a subtraction of the predicted signal profile u(n) from the measurement signal d(n), since each of the filter coefficients operates to shift and possibly re-scale the amplitude of the predicted signal profile u(n). The estimated measurement signal d̂(n), which is subtracted from the measurement signal d(n) to generate the error signal e(n), is thus formed as a linear combination of M shifted predicted signal profiles u(n), i.e. a linear filtering of u(n).

The adaptive update algorithm 34 may be implemented in many different ways, some of which will be described below. The disclosure is in no way limited to these examples, and the skilled person should have no difficulty of finding further alternatives based on the following description.

There are two main approaches to adaptive filtering: stochastic and deterministic. The difference lies in the minimization of the error signal e(n) by the update algorithm 34, where different minimization criteria are obtained whether e(n) is assumed to be stochastic or deterministic. A stochastic approach typically uses a cost function J with an expectation in the minimization criterion, while a deterministic approach typically uses a mean. The squared error signal $e^2(n)$ is typically used in a cost function when minimizing e(n), since this results in one global minimum. In some situations, the absolute error |e(n)| may be used in the minimization, as well as different forms of constrained minimizations. Of course, any form of the error signal may be used, however convergence towards a global minimum is not always guaranteed and the minimization may not always be solvable.

In a stochastic description of the signal, the cost function may typically be according to, $$J(n)=E\{|e(n)|^2\}$$

and in a deterministic description of the signal the cost function may typically be according to, $$J(n)=\Sigma e^2(n).$$

The first pulses will be removed from the measurement signal d(n) when the error signal e(n) (cost function J(n)) is minimized. Thus, the error signal e(n) will be cleaned from first pulses while retaining the second pulses, once the adaptive filter 30 has converged and reached the minimum error.

In order to obtain the optimal filter coefficients w(n) for the variable filter 32, the cost function J needs to be minimized with respect to the filter coefficients w(n). This may be achieved with the cost function gradient vector ∇J, which is the derivative of J with respect to the different filter coefficients $w_0, w_1, \ldots, w_{M-1}$. Steepest Descent is a recursive method (not an adaptive filter) for obtaining the optimal filter coefficients that minimize the cost function J. The recursive method is started by giving the filter coefficients an initial value, which is often set to zero, i.e., w(0)=0. The filter coefficients is then updated according to, $$w(n+1) = w(n) + \frac{1}{2}\mu[-\nabla J(n)],$$

where w is given by, $$w=[w_0 w_1 \ldots w_{M-1}]^T M \times 1$$

Furthermore, the gradient vector ∇J points in the direction in which the cost is growing the fastest. Thus, the filter coefficients are corrected in the direction opposite to the gradient, where the length of the correction is influenced through the step size parameter μ. There is always a risk for the Steepest Descent algorithm to diverge, since the algorithm contains a feedback. This sets boundaries on the step size parameter μ in order to ensure convergence. It may be shown that the stability criterion for the Steepest Descent algorithm is given by, $$0 < \mu < \frac{2}{\lambda_{max}}$$

where $\lambda_{max}$ is the largest eigenvalue of R, the correlation matrix of the predicted signal profile u(n), given by $$R = E[\bar{u}(n)\bar{u}^T(n)] = \begin{bmatrix} r(0) & r(1) & \ldots & r(M-1) \\ r(1) & r(0) & & r(M-2) \\ \vdots & \vdots & \ddots & \vdots \\ r(M-1) & r(M-2) & \ldots & r(0) \end{bmatrix},$$

where ū(n) is given by, $$\bar{u}(n)=[u(n)u(n-1) \ldots u(n-M+1)]^T M \times 1.$$

If the mean squared error (MSE) cost function (defined by $J=E\{|e(n)|^2\}$) is used, it may be shown that the filter coefficients are updated according to, $$w(n+1)=w(n)\mu E[\bar{u}(n)e(n)]$$

where e(n) is given by, $$e(n)=d(n)-\bar{u}^T(n)w(n).$$

The Steepest Descent algorithm is a recursive algorithm for calculation of the optimal filter coefficients when the statistics of the signals are known. However, this information is often unknown. The Least Mean Squares (LMS) algorithm is a method that is based on the same principles as the Steepest Descent algorithm, but where the statistics is estimated continuously. Thus, the LMS algorithm is an adaptive filter, since the algorithm may adapt to changes in the signal statistics (due to continuous statistic estimations), although the gradient may become noisy. Because of the noise in the gradient, the LMS algorithm is unlikely to reach the minimum error which the Steepest Descent algorithm does. Instantaneous estimates of the expectation are used in the LMS algorithm, i.e., the expectation is removed. Thus, for the LMS algorithm, the update equation of the filter coefficients becomes $$w(n+1)=w(n)+\mu\bar{u}(n)e(n).$$

The convergence criterion of the LMS algorithm is the same as for the Steepest Descent algorithm. In the LMS algorithm, the step size is proportional to the predicted signal profile u(n), i.e., the gradient noise is amplified when the predicted signal profile is strong. One solution to this problem is to normalize the update of the filter coefficients with $$\|\bar{u}(n)\|^2 = \bar{u}^T(n)\bar{u}(n)$$

The new update equation of the filter coefficients is called the Normalized LMS, and is given by $$w(n+1) = w(n) + \frac{\tilde{\mu}}{a + \|\bar{u}(n)\|^2} \bar{u}(n)e(n),$$

where $0 \le \mu \le 2$, and a is a positive protection constant.

There are many more different alternatives to the LMS algorithm, where the step size is modified. One of them is to use a variable adaptation step, $$w(n+1) = w(n) + \alpha(n)\bar{u}(n)e(n),$$

where $\alpha(n)$ for example may be, $$\alpha(n) = \frac{1}{n+c},$$

where c is a positive constant. It is also possible to choose independent adaptation steps for each filter coefficient in the LMS algorithm, e.g., according to, $$w(n+1) = w(n) + A\bar{u}(n)e(n),$$

where A is given by, $$A = \begin{bmatrix} \alpha_1 & 0 & 0 & \cdots & 0 \\ 0 & \alpha_2 & 0 & \cdots & 0 \\ 0 & 0 & \alpha_3 & \cdots & 0 \\ \vdots & \vdots & \vdots & \ddots & \vdots \\ 0 & 0 & 0 & \cdots & \alpha_M \end{bmatrix}.$$

If instead the following cost function $$J(n) = E\{|e(n)|\}$$

is used, then the update equation becomes $$w(n+1) = w(n) + \alpha \operatorname{sign}[e(n)]\bar{u}(n)$$

This adaptive filter is called the Sign LMS, which is used in applications with extremely high requirements on low computational complexity.

Another adaptive filter is the Leaky LMS, which uses a constrained minimization with the following cost function $$J(n) = E\{|e(n)|^2\} + \alpha\|w(n)\|^2.$$

This constraint has the same effect as if white noise with variance α was added to the predicted signal profile u(n). As a result, the uncertainty in the input signal u(n) is increased, which tends to hold the filter coefficients back. The Leaky LMS is preferably used when R, the correlation matrix of u(n), has one or more eigenvalues equal to zero. However, in systems without noise, the Leaky LMS makes performance poorer. The update equation of the filter coefficients for the Leaky LMS is given by, $$w(n+1) = (1 - \mu\alpha)w(n) + \mu\bar{u}(n)e(n)$$

Instead of minimizing the MSE cost function as above, the Recursive Least Squares (RLS) adaptive filter algorithm minimizes the following cost function $$J(n) = \sum_{i=1}^{n} \lambda^{n-i}|e(i)|^2,$$

where λ is called forgetting factor, $0 \le \lambda \le 1$, and the method is called Exponentially Weighted Least Squares. It may be shown that the update equations of the filter coefficients for the RLS algorithm are, after the following initialization $$w(0) = 0_{M \times 1}$$

$$P(0) = \delta^{-1} I_{M \times M}$$

where $I_{M \times M}$ is the identity matrix M×M, given according to $$k(n) = \frac{\lambda^{-1} P(n-1)\bar{u}(n)}{1 + \lambda^{-1}\bar{u}^T(n)P(n-1)\bar{u}(n)}$$

$$\xi(n) = d(n) - w^T(n-1)\bar{u}(n)$$

$$w(n) = w(n-1) + k(n)\xi(n)$$

$$P(n) = \lambda^{-1} P(n-1) - \lambda^{-1} k(n)\bar{u}^T(n)P(n-1),$$

where δ is a small positive constant for high signal-to-noise ratio (SNR), and a large positive constant for low SNR, $\delta \ll 0.01 \sigma u2$, and $\zeta(n)$ corresponds to e(n) in the preceding algorithms. During the initialization phase the following cost function $$J(n) = \sum_{i=1}^{n} \lambda^{n-i}|e(i)|^2 + \delta\lambda^n\|w(n)\|^2,$$

is minimized instead, due to the use of the initialization $P(0) = \delta^{-1} I$. The RLS algorithm converges in approximately 2M iterations, which is considerably faster than for the LMS algorithm. Another advantage is that the convergence of the RLS algorithm is independent of the eigenvalues of R, which is not the case for the LMS algorithm.

Several RLS algorithms running in parallel may be used with different λ and δ, which may be combined in order to improve performance, i.e., λ=1 may also be used in the algorithm (steady state solution) with many different δ:s.

It should be noted that both the LMS algorithm and the RLS algorithm may be implemented in fixed-point arithmetic, such that they may be run on a processor that has no floating point unit, such as a low-cost embedded microprocessor or microcontroller.

Figure 25A:
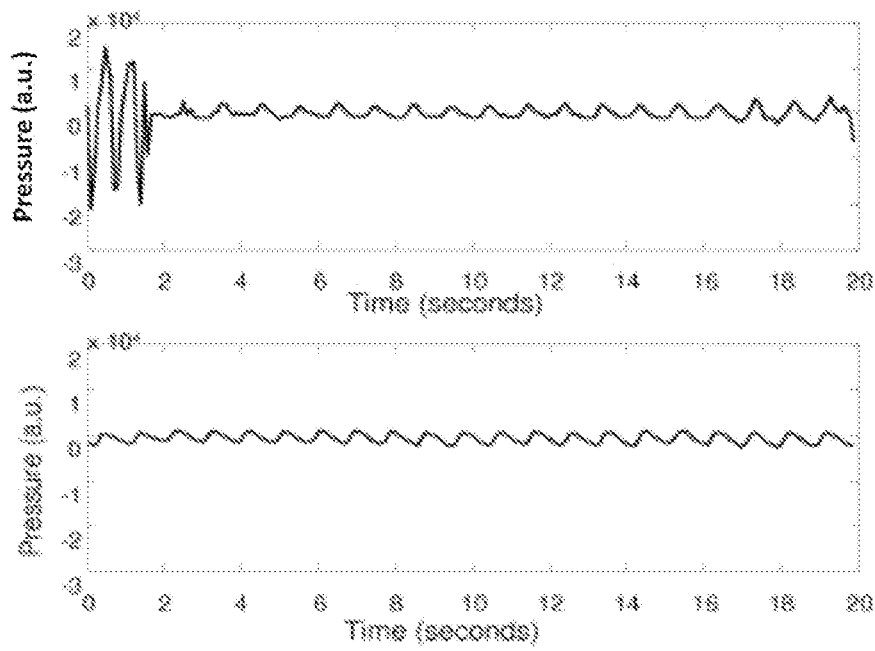
FIG. 25A illustrates a filtered pressure signal (top) and a corresponding heart signal (bottom), obtained from a venous pressure sensor.

To illustrate the effectiveness of the removal process using an adaptive filter, the top graph in FIG. 25A illustrates the error signal e(n) output by the adaptive filter structure in FIG. 24, using an RLS algorithm as adaptive update algorithm 32, operating on a measurement signal from the venous sensor 4a in FIG. 17, at a flow rate of 430 ml/min. The adaptive filter structure is provided with a predicted signal profile obtained in a reference measurement at the same flow rate. The RLS algorithm, designed with M=15, converges after about 2M, which equals 3 seconds with the current sampling frequency of 10 Hz. The top graph thus shows the measurement signal after elimination of the first pulses. The bottom graph in FIG. 25A is included for reference, and shows the measurement signal from the venous sensor 4a while the blood pump 3 is stopped. Clearly, the adaptive filtering is operable to provide, after a convergence period, a monitoring signal that properly represents the second pulses.

Figure 25B:
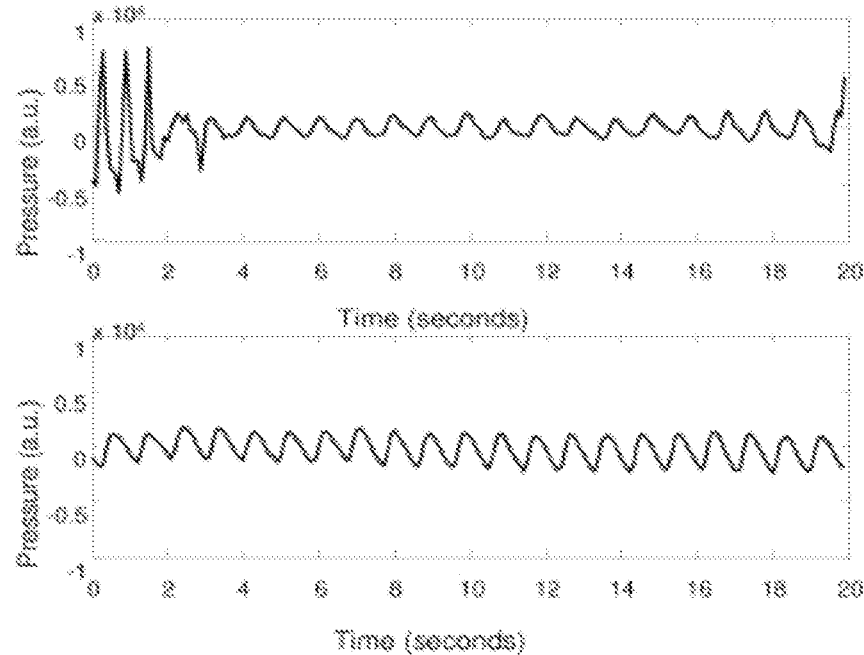
FIG. 25B illustrates a filtered pressure signal (top) and a corresponding heart signal (bottom), obtained from an arterial pressure sensor.

FIG. 25B corresponds to FIG. 25A, but is obtained for a measurement signal from the arterial sensor 4b in FIG. 17.

Irrespective of implementation, the performance of the adaptive filter 30 (FIG. 24) may be further improved by switching the adaptive filter 30 to a static mode, in which the update algorithm 34 is disabled and thus the filter coefficients of the filter 32 (FIG. 24) are locked to a current set of values. The switching of the adaptive filter 30 may be controlled by an external process that analyses the second pulses in the error signal e(n), typically in relation to first pulse data. The first pulse data may be obtained from the measurement signal, a reference signal (see above), a dedicated pulse sensor, a control unit for the first pulse generator, etc. The adaptive filter 30 may be switched into the static mode if the external process reveals that the rate of second pulses starts to approach the rate of the first pulses and/or that the amplitude of the second pulses is very weak (in relation to an absolute limit, or in relation to a limit given by the amplitude of the first pulses). The adaptive filter may remain in static mode for a predetermined time period, or until released by the process.

In a variant, a predicted signal profile of the second pulses (denoted "predicted second profile") is used as input signal to the adaptive filter 160 (instead of the predicted signal profile of the first pulses), and the monitoring signal is formed by the estimated measurement signal $\hat{d}(n)$ (instead of the error signal e(n)). The foregoing discussion with respect to adaptive filters is equally applicable to this variant.

The invention has mainly been described above with reference to a few embodiments. However, as readily appreciated by a person skilled in the art, other embodiments than the ones disclosed above are equally possible with the scope and spirit of the invention, which is defined and limited only by the appended patent claims.

For example, the measurement and reference signals may originate from any conceivable type of pressure sensor, e.g. operating by resistive, capacitive, inductive, magnetic or optical sensing, and using one or more diaphragms, bellows, Bourdon tubes, piezo-electrical components, semiconductor components, strain gauges, resonant wires, accelerometers, etc.

Although FIG. 14 indicates that the pressure sensor 4a-4c is connected to the first sub-system S1, it may instead be connected to measure the fluid pressure in the second sub-system S2. Further, the fluid containing system need not be partitioned into first and second sub-systems S1, S2 connected via a fluid connection C, but may instead be a unitary fluid containing system associated with a first pulse generator and a second pulse generator, wherein the each pressure sensor is arranged in the fluid containing system to detect a first pulse originating from the first pulse generator and a second pulse originating from the second pulse generator.

Further, the inventive technique is applicable for monitoring in all types of extracorporeal blood flow circuits in which blood is taken from the systemic blood circuit of the patient to have a process applied to it before it is returned to the patient. Such blood flow circuits include circuits for hemodialysis, hemofiltration, hemodiafiltration, plasmapheresis, apheresis, extracorporeal membrane oxygenation, assisted blood circulation, and extracorporeal liver support/dialysis. The inventive technique is likewise applicable for monitoring in other types of extracorporeal blood flow circuits, such as circuits for blood transfusion, infusion, as well as heart-lung-machines.

The inventive technique is also applicable to fluid systems containing other liquids than blood.

Further, the inventive technique is applicable to remove pressure pulses originating from any type of pumping device, not only rotary peristaltic pumps as disclosed above, but also other types of positive displacement pumps, such as linear peristaltic pumps, diaphragm pumps, as well as centrifugal pumps. In fact, the inventive technique is applicable for removing pressure pulses that originate from any type of pulse generator, be it mechanic or human.

Likewise, the inventive technique is applicable to isolate pressure pulses originating from any type of pulse generator, be it human or mechanic.

The inventive technique need not operate on real-time data, but may be used for processing off-line data, such as a previously recorded measurement signal.

End Appendix A

APPENDIX B

Brief Description of the Drawings

Embodiments of the inventive concepts will now be described in more detail with reference to the accompanying schematic drawings FIGS. 26-34 discussed herein above.

DETAILED DESCRIPTION OF INVENTIVE CONCEPTS AND EMBODIMENTS

In the following, inventive concepts and associated embodiments will be described with reference to fluid containing systems in general. Thereafter, the inventive concepts will be further exemplified in the context of systems for extracorporeal blood treatment.

Throughout the following description, like elements are designated by the same reference signs.

General

Figure 26:
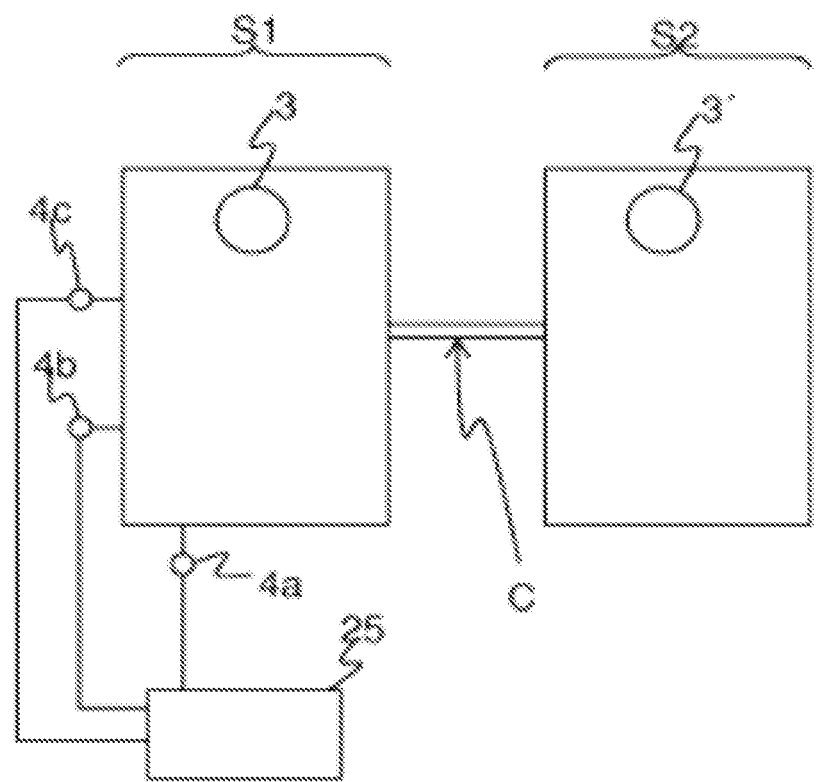
FIG. 26 is a schematic view of a general fluid arrangement in which the inventive concepts may be used for monitoring the integrity of a fluid connection.

FIG. 26 illustrates a general fluid arrangement in which a fluid connection C is established between a first fluid containing system S1 and a second fluid containing system S2. The fluid connection C may or may not transfer fluid from one system to the other. A first pulse generator 3 is arranged to generate a series of pressure waves in the fluid within the first system S1, and a second pulse generator 3' is arranged to generate a series of pressure waves in the fluid within the second system S2. A pressure sensor 4c is arranged to measure the fluid pressure in the first system S1. As long as the fluid connection C is intact, pressure waves generated by the second pulse generator 3' will travel from the second system S2 to the first system S1, and thus second pulses originating from the second pulse generator 3' will be detected by the pressure sensor 4c in addition to first pulses originating from the first pulse generator 3. It is to be noted that either one of the first and second pulse generators 3, 3' may include more than one pulse-generating device. Further, any such pulse-generating device may or may not be part of the respective fluid containing system S1, S2.

The fluid arrangement of FIG. 26 further includes a surveillance device 25 which is connected to the pressure sensor 4c, and possibly to one or more further pressure sensors 4a, 4b, as indicated in FIG. 26. Thereby, the surveillance device 25 acquires one or more measurement signals that are time-dependent to provide a real time representation of the fluid pressure in the first system S1. The surveillance device 25 monitors the integrity of the fluid connection C, based on the principle that the presence of second pulses indicates that the fluid connection C is intact, whereas absence of second pulses indicates that the fluid connection C is compromised. The absence of second pulses may bring the surveillance device 25 to issue an alarm or warning signal, and/or alert a control system of the first or second fluid containing systems S1, S2 to take appropriate action.

The surveillance device 25 is thus configured to continuously process the time-dependent measurement signal(s) to determine whether second pulses are present or not. Typically, the determination involves analyzing the measurement signal(s), or a pre-processed version thereof, in the time domain to calculate a value of an evaluation parameter which is indicative of the presence or absence of second pulses in the measurement signal(s). Depending on implementation, the surveillance device 25 may use digital components or analog components, or a combination thereof, for receiving and processing the measurement signal(s).

In the context of the present disclosure, "absence" of a pulse may imply that the pulse has disappeared, or at least that it has decreased sufficiently in magnitude compared to the pulse deemed to be "present". The assessment of presence or absence may involve calculating an evaluation parameter value based on the measurement signal(s) and comparing the parameter value to a threshold value.

First Inventive Concept

Figure 27:
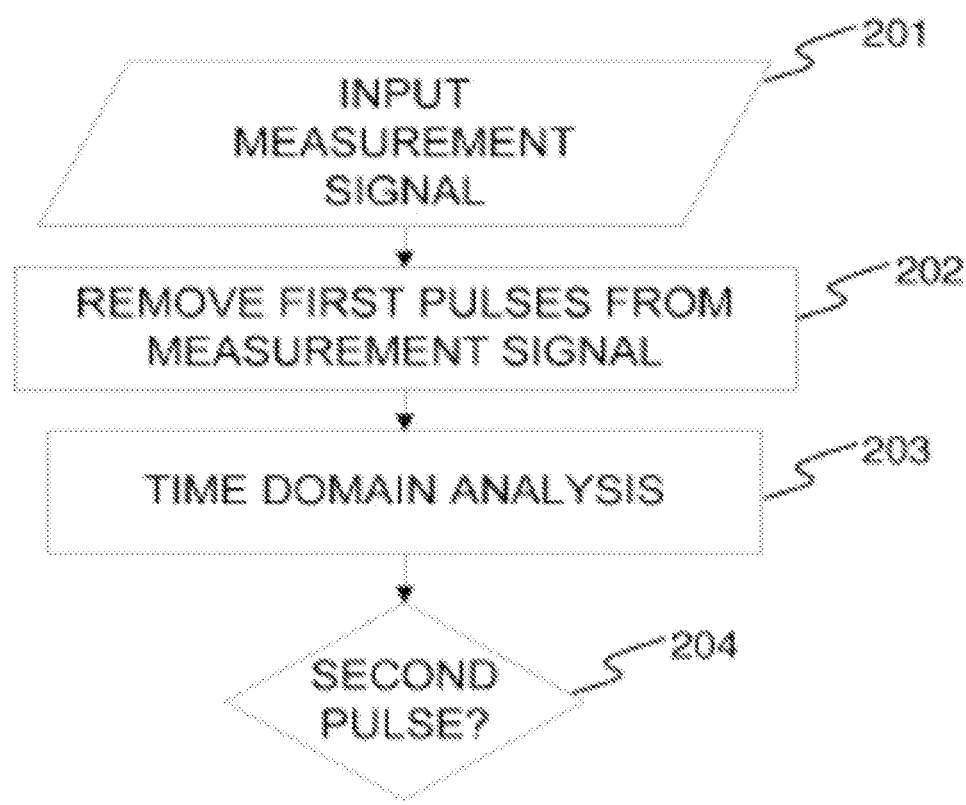
FIG. 27 is a flow chart of a monitoring process according to a first inventive concept.

FIG. 27 is a flow chart that illustrates steps of a monitoring process according to a first inventive concept. A measurement signal is received (step 201) and subjected to a filtering process (step 202) that essentially removes the first pulses from the measurement signal, while leaving at least part of the second pulses intact. The filtered measurement signal is then subjected to a time domain analysis (step 203), in which a value of an evaluation parameter is calculated based on signal values within a time window in the filtered measurement signal, which is denoted "evaluation segment" in the following. The calculation is typically designed such that the evaluation parameter represents the distribution of signal values within the evaluation segment. Based on the resulting value of the evaluation parameter, it is decided (step 204) whether the fluid connection is intact or not, typically by comparing the resulting value to a threshold value.

For continuous surveillance, a time sequence of evaluation parameter values is calculated based on a time sequence of evaluation segments obtained from the measurement signal. These evaluation segments may be overlapping or non-overlapping in time. In one embodiment, individual sections of the measurement signal are acquired, filtered and analyzed, one after the other. Each evaluation segment may correspond to one such section of the measurement signal; the time window is thus applied already when the measurement signal is acquired. In another embodiment, the measurement signal is continuously acquired and filtered, whereupon evaluation segments are extracted from the filtered signal and analyzed.

Figure 28A:
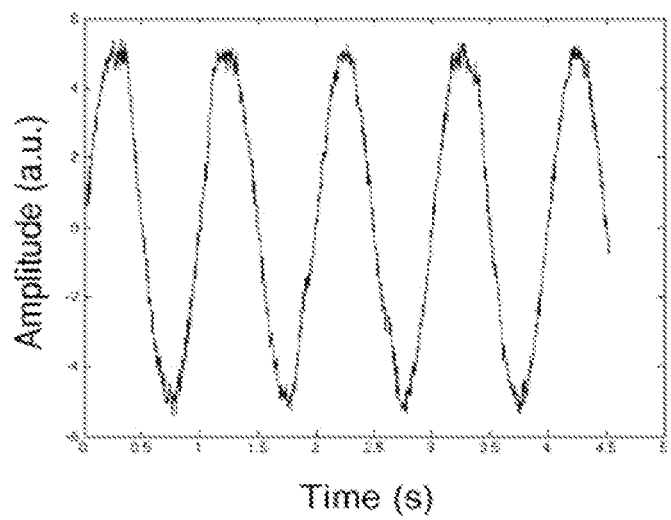
FIG. 28A is a plot of the measurement signal as a function of time.
Figure 28B:
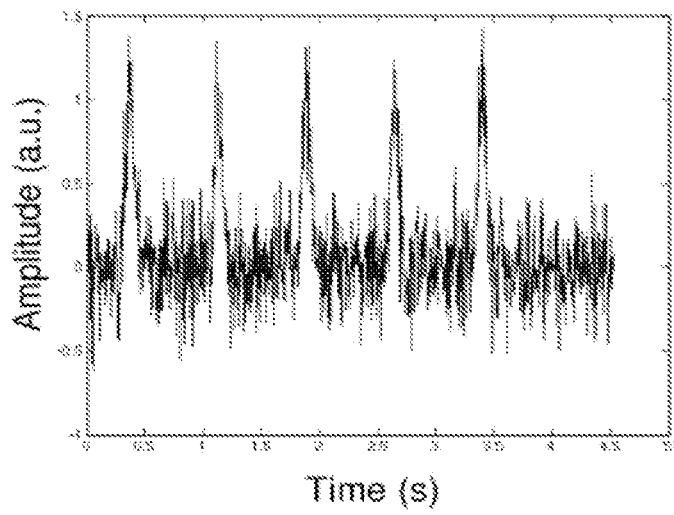
FIG. 28B is a plot of the measurement signal in FIG. 28A after filtering.
Figure 28C:
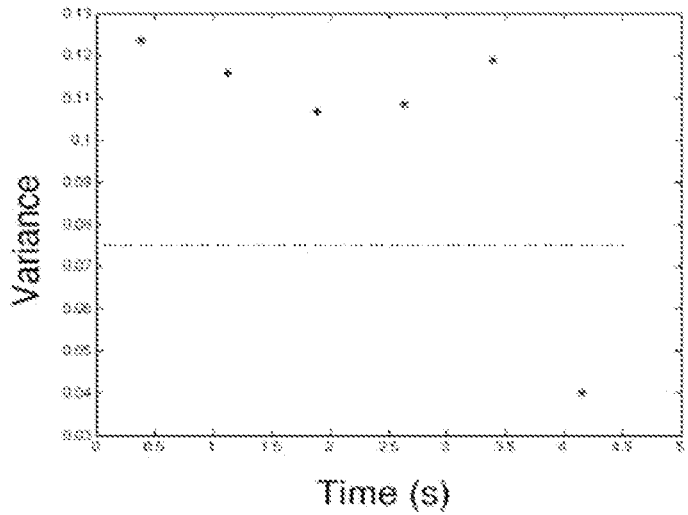
FIG. 28C illustrates a statistical dispersion measure calculated for a sequence of time windows in the signal in FIG. 28B.

FIG. 28A shows an example of a time-dependent measurement signal containing first and second pulses with a relative magnitude of 10:1. The first and second pulses have a frequency of 1 Hz and 1.33 Hz, respectively. FIG. 28B shows the time-dependent measurement signal after removal of the first pulses, leaving only second pulses and noise. It should be noted that there is an absence of second pulses after about 4 seconds. FIG. 28C illustrates a variance measure calculated for a sequence of non-overlapping time windows in the filtered measurement signal in FIG. 28B, each time window being about 0.75 seconds. Clearly, by using the variance measure as an evaluation parameter, it is possible to detect the absence of the second pulse at the time point of about 4 seconds. An exemplifying threshold value is indicated by a dotted line.

The first inventive concept has the potential of providing a comparatively robust measure of the integrity of the fluid connection C. By analyzing the temporal distribution of signal values within the evaluation segment, an improved tolerance to noise and disturbing signals may be obtained.

Furthermore, compared to techniques that rely on frequency domain analysis of the measurement signal for detecting the presence of second pulses, the first inventive concept may provide an improved tolerance to variations in the pulse repetition interval of the second pulse generator 3', since the first inventive concept relies on a time domain analysis. Such variations may occur, e.g., when the second pulse generator 3' is a human heart, and the second system S2 thus is the blood system of a human Variations in heart rhythm (heart rate variability, HRV) will cause the peak from the heart in the frequency domain to be smeared out, making it harder to detect. In healthy subjects under calm conditions, HRV may be as large as 15%. Unhealthy subjects may suffer from severe heart conditions such as atrial fibrillation and supraventricular ectopic beating, which may lead to an HRV in excess of 20%, and ventricular ectopic beating, for which HRV may be in excess of 60%. These heart conditions are not uncommon among, e.g., dialysis patients.

As long as the time window is selected such that each evaluation segment contains at least one second pulse, the presence/absence of second pulses will affect the evaluation parameter, if properly chosen. A fixed-length time window may be used, with the length of the time window being chosen with respect to a maximum pulse repetition rate of the second pulse generator 3'. The length of the time window may be set by constraints in the second pulse generator 3' or by a selected performance limit of the surveillance method. Alternatively, the length of the time window and/or the location of the time window in the filtered measurement signal may be selected based on a predicted timing of the second pulse(s) to be detected. The acquisition and use of such a predicted timing ("timing information") will be further exemplified below with reference to the second inventive concept.

Still further, the time domain analysis according to the first inventive concept may allow for faster detection than a frequency domain analysis, since the former may have the ability to detect a single second pulse in the evaluation segment whereas the generation of a frequency spectrum requires a greater number of second pulses in the evaluation segment. Thus, frequency domain analysis may be associated with a greater time lag than time domain analysis.

The evaluation parameter may be calculated as a statistical dispersion measure of the signal values within the evaluation segment. Non-limiting examples of potentially useful statistical dispersion measures include standard deviation ($\sigma$), variance ($\sigma^2$), coefficient of variation ($\sigma/\mu$) and variance-to-mean ($\sigma^2/\mu$). Other examples include a sum of differences, e.g. given by $$\sum_{i=2}^{n} |x_i - x_{i-1}|, \text{ or } \sum_{i=1}^{n} \sum_{j=1}^{n} |x_i - x_j|,$$

or an energy measure, such as $$\sum_{i=1}^{n} x_i 2,$$

with n being the number of signal values x in the evaluation segment. Yet other examples include a measure based on a sum of absolute differences from an average value m, with the average value m being calculated for the signal values in the evaluation segment using any suitable function, such as arithmetic mean, geometric mean, median, etc. It is to be noted that all of the above suggested dispersion measures also include normalized and/or weighted variants thereof.

As an alternative or supplement to calculating a statistical dispersion measure, the evaluation parameter may result from a matching procedure, in which the evaluation segment is matched to one or more predicted signal profiles of a second pulse. Preferably, but not necessarily, each predicted signal profile represents a single second pulse. Typically, the matching procedure involves convolving or cross-correlating the evaluation segment and the predicted signal profile, and the evaluation parameter value is a resulting correlation value, typically the maximum correlation value.

Figure 29A:
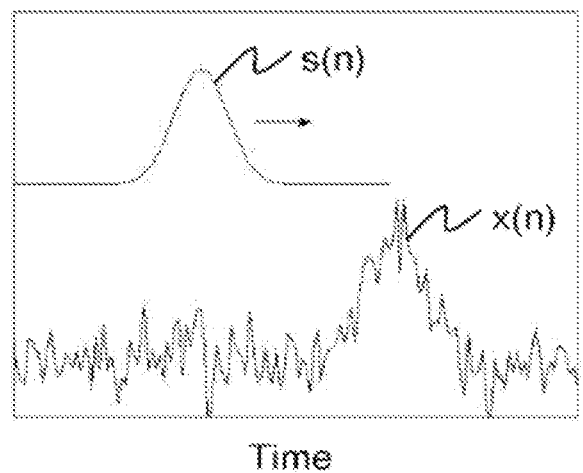
FIG. 29A illustrates a matching procedure between a measurement signal and a predicted signal profile.
Figure 29B:
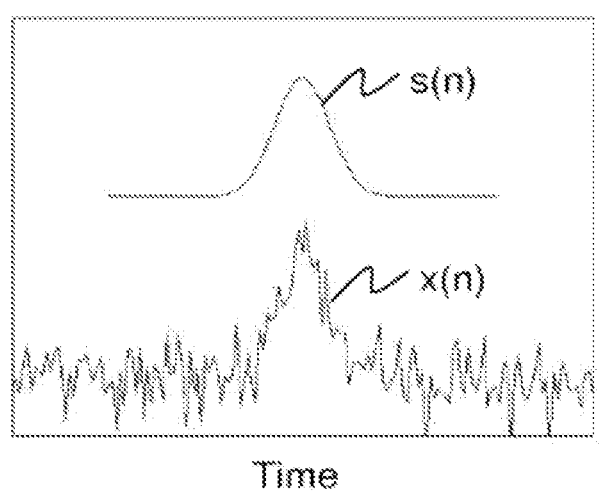
FIG. 29B illustrates the position of best match.
Figure 29C:
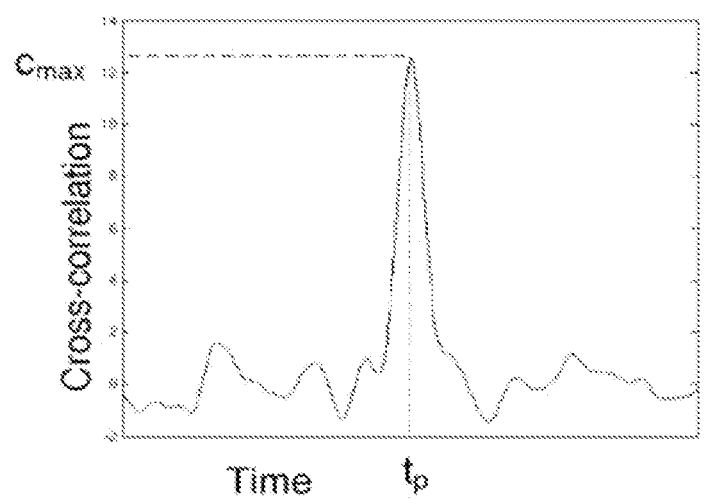
FIG. 29C is a correlation curve resulting from the matching procedure in FIG. 29A.

A matching procedure based on cross-correlation is further exemplified in FIGS. 29A-29C. The matching procedure is used to distinguish between the hypotheses $H_0: x(n)=w(n)$ $H_1: x(n)=s(n)+w(n)$ with $x(n)$ being the evaluation segment, $w(n)$ being an error signal representing disturbances introduced by noise/signal interference/measurement errors, etc, and $s(n)$ being the predicted signal profile of the second pulse. If $H_1$ is deemed more likely than $H_0$, then a second pulse has been identified and the fluid connection C is deemed intact. If $H_0$ is deemed more likely than $H_1$, then a second pulse cannot be identified and the fluid connection C may be compromised.

FIG. 29A is a graph showing an example of a predicted signal profile $s(n)$ and an evaluation segment $x(n)$. In this particular example, the evaluation segment has a signal-to-noise ratio (SNR) of 4.8 dB, i.e. the energy of the signal profile $s(n)$ is 3 times the energy of the error signal $w(n)$. During the cross-correlation, the signal profile $s(n)$ is slid in a number of time steps along the time axis, as indicated by arrow in FIG. 29A, and the integral of the product $s(n) \cdot x(n)$ is calculated for each time step. The cross-correlation thus results in a time sequence of correlation values, with the maximum correlation value indicating the time point of best match between $x(n)$ and $s(n)$. FIG. 29B illustrates the relative position between $x(n)$ and $s(n)$ at the time point for best match, and FIG. 29C illustrates the resulting correlation values as a function of said time steps. The magnitude of the maximum correlation value, optionally calculated as a weighted average within a range around the maximum correlation value ($c_{max}$), may thus be used to distinguish between the above hypotheses.

As indicated in FIG. 29C, the matching procedure not only identifies the presence of a second pulse, it also provides an indication of the location of the second pulse in the evaluation segment, given by the time point ($t_p$) for the maximum correlation value ($c_{max}$). This time point may be used to assess the reliability of the determined maximum correlation value, by comparing this time point to a predicted time point. Such a predicted time point may be obtained from aforesaid timing information, as will be further explained below in relation to the second inventive concept.

The predicted signal profile may be generated as an average of a number of recordings of second pulses. For example, it may be generated by averaging a number of evaluation segments, before and/or during the monitoring process.

To improve the signal quality of the predicted profile, with or without averaging, the measurement signal may be acquired while the first pulse generator is stopped, whereby the measurement signal is free of first pulses. Thus, the first pulse generator may be intermittently stopped during the monitoring process for calculation of an updated signal profile of the second pulses.

In another variant, the predicted signal profile is obtained from one or more reference signals originating from a reference pressure sensor (e.g. any one of pressure sensors 4a-4c in FIG. 26) in the first system. Such a reference pressure sensor is suitably arranged to detect second pulses even if the fluid connection is compromised, e.g. via a second fluid connection between the first and second fluid containing systems. The reference pressure sensor may be installed to be isolated from the first pulses, such that the reference signal is essentially free of first pulses. Alternatively, if the reference signal includes both first and second pulses, the reference signal may be subjected to a filtering process (e.g. according to step 202 in FIG. 27) to remove the first pulses while leaving the second pulses intact in the reference signal. An example of such a reference pressure sensor is an arterial pressure sensor in an extracorporeal blood flow circuit. In such an extracorporeal blood flow circuit, the measurement signal(s) may originate from one or more venous pressure sensors, e.g. if the monitoring process aims at monitoring the integrity of the venous-side fluid connection between the extracorporeal blood flow circuit and a patient.

In one specific implementation, the reference signal is obtained continuously or intermittently during the monitoring process, and the predicted signal profile is continuously or intermittently calculated based on the reference signal. Thus, in the context of the above-mentioned extracorporeal blood flow circuit, the integrity of the venous-side fluid connection may be monitored by continuously matching evaluation segments from the venous pressure sensor against a predicted signal profile obtained from the arterial pressure sensor. It is even conceivable that the predicted signal profile is updated for each evaluation segment (denoted "synchronous monitoring" in the following). The matching procedure may benefit from the use of timing information, as will be further explained below in relation to the second inventive concept. Alternatively, the predicted signal profile may be pre-generated, e.g. by averaging recordings of second pulses from a number of fluid arrangements, similar to the one that is being monitored (cf. FIG. 26). Optionally, such a pre-generated signal profile may be adapted to specifics of the fluid arrangement to be monitored, by applying a mathematical model taking into account arrangement-specific parameters, such a type of fluid connection, flow rate, fluid characteristics, etc. Alternatively, the predicted signal profile may be obtained entirely by mathematical modeling based on arrangement-specific parameters. According to yet another alternative, a standard profile is used as predicted signal profile, e.g. a bell-shaped function such as a Gaussian distribution function.

In order to improve the detection of second pulses, it is conceivable to subject the filtered measurement signal/evaluation segment to a signal enhancement process, which removes high-frequency components (cf. error signal w(n)), before calculation of the evaluation parameter value. Such a signal enhancement process may involve subjecting the filtered measurement signal/evaluation segment to a low-pass filtering. However, a more significant improvement in SNR of the evaluation segment may be achieved by averaging several consecutive second pulses in the filtered measurement signal, again based on the above-mentioned predicted timing of the second pulse(s) (i.e. timing information). Such a signal enhancement process would thus involve using the predicted timing to identify a set of second pulse segments in the filtered measurement signal, aligning the second pulse segments in the time domain based on the predicted timing, and generating an average representation by summing the aligned signal values for each time value in the time domain. Optionally, the average representation is normalized by the number of second pulse segments to generate a true average. The average representation may then be used as the above-mentioned evaluation segment, or the evaluation segment may be extracted from a time window within the average representation.

Figure 30A:
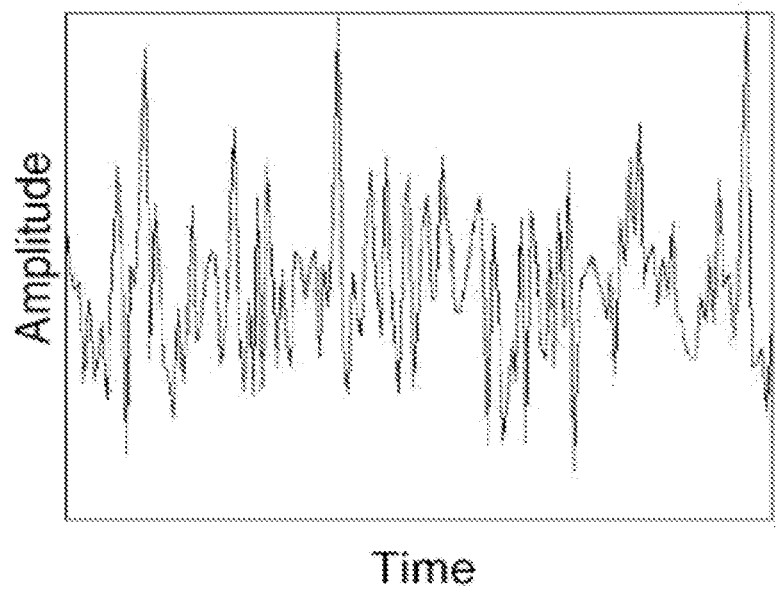
FIG. 30A is a plot of a signal segment containing a second pulse.
Figure 30B:
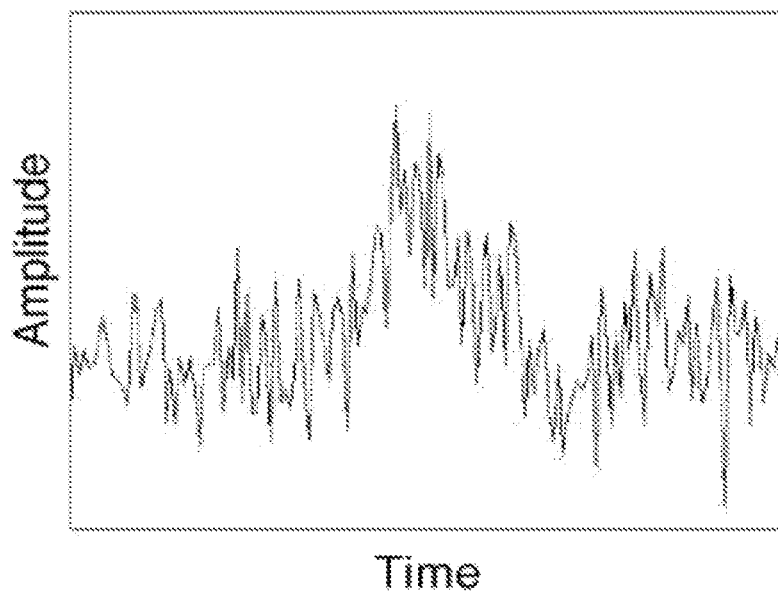
FIG. 30B is plot of an evaluation segment generated by averaging ten signal segments.

The signal enhancement process is further exemplified in FIGS. 30A-30B. FIG. 30A is a time domain representation of a filtered measurement signal x(n)=s(n)+w(n) with a SNR of −9 dB, i.e. the energy of the error signal w(n) is 8 times the energy of the signal profile s(n), making time domain analysis for detection of the second pulse difficult, if not impossible. FIG. 30B is a time domain representation after averaging of 10 different second pulse segments similar to the one in FIG. 30A. Clearly, the SNR has been improved significantly, allowing a second pulse to be detected using time domain analysis.

It is to be understood that the monitoring process of FIG. 27 may operate on more than one measurement signal, if the fluid arrangement to be monitored includes more than one pressure sensor (cf. 4a, 4b in FIG. 26). In such a configuration, the above-described signal enhancement process may involve using aforesaid timing information to identify and average second pulse segments from at least two filtered measurement signals originating from different pressure sensors. Thus, the second pulse segments may be extracted from plural time windows in each measurement signal, and/or from one or more time windows in different measurement signals.

The filtering process according to step 202 in FIG. 27 aims at removing the first pulses from the measurement signal to such an extent that the second pulses may be detected by the subsequent time domain analysis (step 203). For example, a comb filter and/or a combination of band-stop or notch filters, typically cascade coupled, may be operated on the measurement signal to block out all frequency components originating from the first pulse generator 3. Alternatively, such blocking may be achieved by the use of one or more adaptive filters and notch-equivalent filters, e.g. as disclosed in aforesaid WO 97/10013. In yet another alternative embodiment, the measurement signal is processed in the time domain to cancel the first pulses. In such an embodiment, a standard signal profile of the first pulses may be obtained, which is then subtracted from the measurement signal at suitable amplitude and phase. The phase is indicated by phase information which may be obtained from a signal generated by a phase sensor coupled to the first pulse generator 3, or from a control signal for the first pulse generator 3. The standard signal profile may be obtained from one or more of the pressure sensors 4a-4c in the first fluid containing circuit S1, suitably by identifying and averaging a set of first pulse segments in the measurement signal(s) similarly to the above-mentioned signal enhancement process. The standard signal profile may or may not be updated intermittently during the monitoring process. Alternatively, a predetermined standard signal profile is used, which optionally may be modified according to a mathematical model accounting for wear in the first pulse generator, fluid flow rates, tubing dimensions, speed of sound in the fluid, etc. It should be noted that by filtering the measurement signal in the time domain, instead of the frequency domain, it is possible to eliminate the first pulses and still retain the second pulses, even if the first and second pulses overlap in the frequency domain.

Second Inventive Concept

Figure 31:
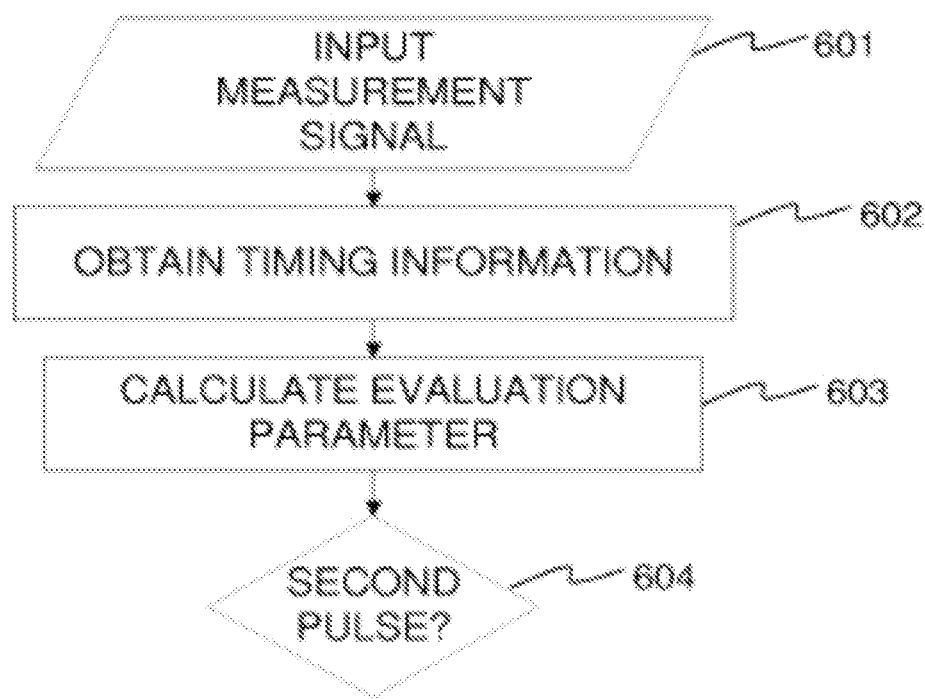
FIG. 31 is a flow chart of a monitoring process according to a second inventive concept.
Figure 32:
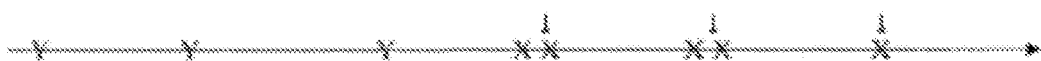
FIGS. 32A-32D illustrate processing of candidate pulses identified in a measurement signal.
Figure 32:
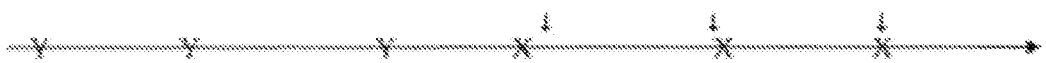
Figure 32:
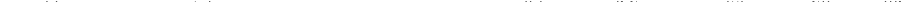
Figure 32:

FIG. 31 is a flow chart that illustrates steps of a monitoring process according to a second inventive concept. In this process, a measurement signal is received (step 601) and timing information is obtained, from the measurement signal or otherwise (step 602). The timing information is indicative of the timing of second pulses in the measurement signal. Subsequently, the measurement signal is processed (step 603) based on the timing information, to calculate a value of an evaluation parameter which is indicative of the presence or absence of a second pulse in the measurement signal. Based on the resulting value of the evaluation parameter, it is decided (step 604) whether the fluid connection is intact or not, typically by comparing the resulting value to a threshold value.

Thus, in the second inventive concept, timing information indicates the expected position of a second pulse in the measurement signal. This additional information may allow the second pulse to be identified from other types of signal features, e.g. different/simpler evaluation parameters, and/or it may allow for an increased reliability in detecting presence/absence of second pulses.

Furthermore, as explained above, the provision of timing information allows for signal enhancement by identifying and averaging second pulse segments in one or more measurement signals. The signal enhancement may increase the SNR of the measurement signal, allowing for the use of a rudimentary measure as evaluation parameter, such as signal amplitude, local maximum, local average, etc. This may serve to improve the processing speed and/or allow for less sophisticated detection equipment.

It is to be understood that the second inventive concept may be combined with any of the features of the first inventive concept. For example, the measurement signal may be filtered to remove first pulses, and the evaluation parameter may be calculated for an evaluation segment given by signal values within a time window in the filtered measurement signal. Also, any one of the evaluation parameters suggested in relation to the first inventive concept is equally applicable to the second inventive concept. It is to be noted, however, that the filtering of the measurement signal is not an essential feature of the second inventive concept, since the use of timing information may allow second pulses to be detected in the measurement signal even in the presence of first pulses.

The second inventive concept may also improve the detection speed, since the timing information may provide a predicted time point for the second pulse in the measurement signal/filtered measurement signal/evaluation segment. Thereby, the number of signal values that need to be processed for calculation of the evaluation parameter value may be reduced. For example, the aforesaid matching procedure may be simplified, since the correlation between the predicted signal profile and the evaluation segment need only be calculated for the predicted time point, or a confined time range around this predicted time point. Correspondingly, the calculation of a statistical dispersion measure or the above-mentioned rudimentary measure may be simplified, since the provision of timing information makes it possible to reduce the size of the time window for extracting the evaluation segment, while still ensuring that each evaluation segment includes at least one second pulse. For example, the size of the time window may be reduced if the timing information indicates a shortened pulse interval between the second pulses, and/or the time window may be centred on the predicted time point of each second pulse.

Still further, the second inventive concept allows for assessing the reliability of a calculated evaluation parameter value, by comparing a time point associated with the evaluation parameter value with a predicted time point given by the timing information. For example, the time point for a maximum correlation value obtained in the aforesaid matching procedure may be compared with a predicted time point for a second pulse. If these time points deviate too much, the monitoring process may determine that a second pulse is absent, even though the magnitude of the correlation value might indicate presence of a second pulse.

The timing information may be obtained in any one of a plurality of different ways. For example, the timing information may be extracted from the output signal of a pulse sensor coupled to the second fluid containing system. The output signal may indicate individual second pulses or an average time between second pulses. In either case, a predicted time point for a second pulse in the measurement signal may be calculated based on the output signal of the pulse sensor and a known difference in arrival time between the pulse sensor and the pressure sensor(s) that generates the measurement signal(s). The pulse sensor may sense the pressure waves that are generated in the fluid by second pulse generator, or it may directly reflect the pulse generation process in the second pulse generator, e.g. via a control signal for the second pulse generator or a pulse rate meter mechanically coupled to the second pulse generator. In one application, to be further exemplified below, the second fluid containing system is a blood system of a human, and the pulse generator is a human heart. In such an application, the timing information may be provided by any conventional pulse sensor such as a pulse watch, a pulse oximeter, an electrocardiograph, etc.

Alternatively, the timing information may be obtained based on the relative timing of previously detected second pulses in the measurement signal, e.g. given by the time points associated with previously calculated evaluation parameter values. For example, the time difference between the two most recently detected second pulses may be used to predict the time point for subsequent second pulse(s).

Alternatively, the timing information may be obtained from one or more reference signals originating from a reference pressure sensor in the first system. Such a reference pressure sensor is suitably arranged to detect second pulses even if the fluid connection is compromised, e.g. via a second fluid connection between the first and second fluid containing systems.

An example of such a reference pressure sensor is an arterial pressure sensor in an extracorporeal blood flow circuit. In such an extracorporeal blood flow circuit, the measurement signal(s) may originate from one or more venous pressure sensors, e.g. if the monitoring process aims at monitoring the integrity of the venous-side fluid connection between the extracorporeal blood flow circuit and a patient. The reference signal may be processed for detection of at least one second pulse, using any suitable technique, including the time domain techniques disclosed herein. The time point of the detected second pulse in the reference signal may then be converted to a predicted time point in the measurement signal/filtered measurement signal/evaluation segment using a known/measured difference in pulse arrival/transit time between the reference sensor and the pressure sensor(s) used for monitoring. Thus, in one embodiment, the difference in transit time is given by a fixed and predefined value.

In another embodiment, the difference in transit time between a blood line on the arterial side and a blood line on the venous side in the extracorporeal blood flow circuit is determined based on the actual arterial and venous pressures (absolute, relative, or average), which may be derived from any suitable sensor in the extracorporeal blood flow circuit (including the venous and arterial pressure sensors). The transit time decreases if the pressure increases, i.e., high pressure equals short transit time. During operation of the extracorporeal blood flow circuit, the venous pressure should be higher than the arterial pressure, and thus the transit time should be shorter in the venous blood line compared to the transit time in the arterial blood line. The difference in transit time may be determined based on, e.g., a physical model or a look-up table. The model/table may not only include information about pressure (absolute, relative, or average), but also information about material (elasticity, plasticity, etc), geometry (length, diameter, wall thickness, etc), temperature (both fluids and ambient temperature), mechanical factors (clamp, tension, actuators, kinking/occlusion, etc), fluid properties (viscosity, water/blood, chemical composition, etc), etc. The thus-determined difference in transit time may then be used to relate a time point of a detected second pulse in the reference signal from the arterial pressure sensor to a predicted time point in the measurement signal/filtered measurement signal/evaluation segment originating from the venous pressure sensor.

In a variant, an improved estimation of the timing information may be obtained by aligning and adding the filtered measurement signal/evaluation segment (derived from the venous pressure signal) with a correspondingly filtered reference signal (derived from the arterial pressure signal), to thereby calculate an average time-dependent signal with improved SNR. The aligning may be based on the aforesaid difference in transit time, given by the actual arterial and venous pressures (absolute, relative, or average). By identifying one or more second pulse(s) in the average time-dependent signal, an improved estimation of the timing information is obtained.

Alternatively or additionally, to potentially improve the precision of the timing information, the timing information may be obtained by intermittently stopping the first pulse generator, while identifying at least one second pulse in the reference signal or the measurement signal.

Optionally, the process of obtaining timing information based on an identified second pulse, be it in the reference signal or the measurement signal, may involve validating the identified second pulse (a candidate pulse) against a temporal criterion. Such a temporal criterion may, e.g., indicate an upper limit and/or a lower limit for the time difference between the time point for the candidate pulse and one or more previously identified (and suitably validated) second pulses. These limits may be fixed, or they may be set dynamically in relation to a preceding time difference. Any candidate pulse that violates the temporal criterion may be removed/discarded from use in obtaining the timing information.

In yet another alternative, the timing information is obtained from a measurement signal using an iterative approach. In this iterative approach, the measurement signal is processed to calculate a time-sequence of evaluation parameter values, e.g. based on the first inventive concept. These evaluation parameter values identify a sequence of candidate pulses and associated candidate time points, which is validated against a temporal criterion. Such a temporal criterion may, e.g., indicate an upper limit and/or a lower limit for the time difference between the candidate time points. The temporal criterion may be given by constraints in the second pulse generator 3'. Any candidate time points that violate the temporal criterion may be removed/discarded, and the timing information may be obtained from the remaining time points.

Different validation methods may be used depending on the availability of previous timing information, i.e. information about time points of preceding second pulses. Such previous timing information may be given by any one of the methods described in the foregoing, or resulting from a previous iteration of the iterative approach.

FIG. 32A illustrates a sequence of candidate pulses (denoted by X), as well as a sequence of preceding second pulses (denoted by Y), laid out on a time axis. In a first validation step, predicted time points (arrows ↓ in FIG. 32B) are calculated based on the previous timing information (e.g. second pulses Y). In a second validation step, a first temporal criterion is applied to remove/discard any candidate pulses that lie too far from the predicted time points, as also shown in FIG. 32B. In a third validation step, a second temporal criterion is applied to retain only the candidate pulse with the largest evaluation parameter value among any candidate pulses that lie too close to each other, as shown in FIG. 32C.

Figure 33:
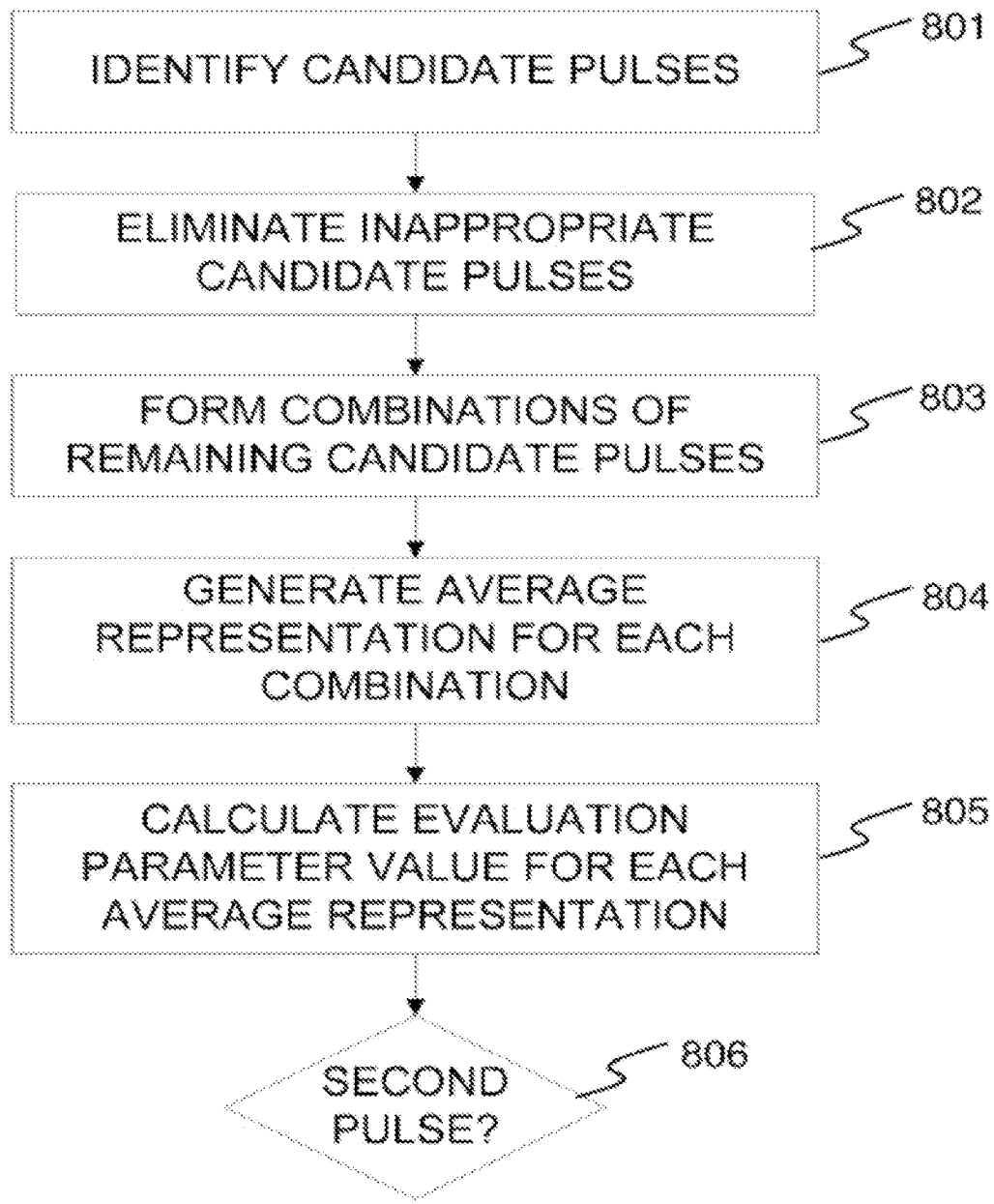
FIG.33 is a flow chart of part of a monitoring process according to the second inventive concept.

A different validation method may be used if previous timing information is not available. FIG. 33 is a flow chart for such a validation method. The initial step 801 of identifying candidate pulses is followed by a first validation step 802, in which a first temporal criterion is applied to retain only the candidate pulse with the largest evaluation parameter value among any candidate pulses that lie too close to each other. FIG. 32D shows an exemplifying result of applying the first validation step 802 to the sequence of candidate pulses in FIG. 32A. Then, in step 803, different combinations of the remaining candidate pulses are formed. In step 804, an average representation is calculated for each such combination, by aligning and summing corresponding signal segments of the measurement signal/filtered measurement signal. The combinations may be formed based on a second temporal criterion that defines an upper limit and/or a lower limit for the time difference between the candidate pulses. In a second validation step 805, an evaluation parameter value is calculated for each such average representation, and the maximum evaluation parameter value is extracted. Finally, in step 806, it is decided whether the fluid connection is intact or not, by comparing the maximum evaluation parameter value to a threshold value. If the maximum evaluation parameter value exceeds the threshold value, it may be concluded that a second pulse is present and that the fluid connection is intact. It may be noted that there is no need to explicitly extract the timing information in the validation method in FIG. 33, since the use of the timing information is embedded in the final step 806 of determining the integrity of the fluid connection.

It should also be noted that different evaluation parameters and/or threshold values may be used in steps 801 and 806. It is also conceivable to use a combination of two or more of the above alternative methods for obtaining the timing information.

Figure 34:
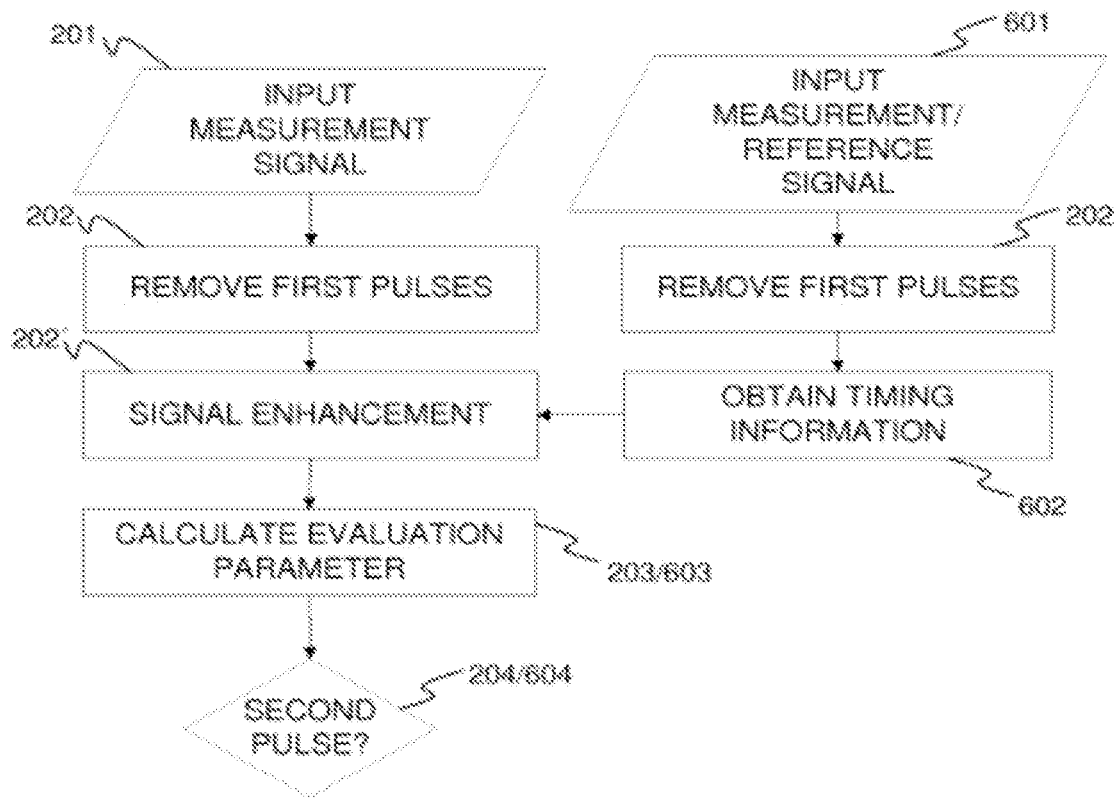
FIG. 34 is a flow chart of a monitoring process that combines the first and second inventive concepts.

FIG. 34 is a flow chart of an embodiment that combines features of the first and second inventive concepts. Specifically, a measurement signal is obtained and filtered according to steps 201 and 202 of the first inventive concept. Then, in step 202', the filtered measurement signal is processed for signal enhancement, based on timing information. As discussed above in relation to FIG. 30, step 202' typically involves identifying, aligning and summing a set of second pulse segments in the filtered measurement signal, to create an average signal representation. An evaluation parameter value is then calculated based on the enhanced signal representation according to step 203/603 of the first/second inventive concept, and it is decided whether the fluid connection is intact or not (steps 204/604). The method also involves receiving a measurement signal (which may be the same measurement signal as in step 201, or the aforesaid reference signal) according to step 601 of the second inventive concept. Then, the measurement/reference signal is filtered to remove the first pulse, if required, according to step 202 of the first inventive concept. Finally, the timing information is obtained according to step 602 of the second inventive concept.

Combinations of Monitoring Techniques

As explained in the foregoing, the technique for monitoring the integrity of the fluid connection may be based on either of the first and second inventive concepts, or a combination thereof. It is also possible to combine such an inventive monitoring technique with one or more conventional monitoring techniques, which e.g. involve the use of an air detector, or a comparison of average pressure levels with threshold values as described by way of introduction. Other conventional monitoring techniques are disclosed in aforesaid WO 97/10013 and US2005/0010118.

It might also be desirable to combine the inventive monitoring techniques with other techniques that are specially designed to handle adverse operating conditions. One such operating condition may arise when the first and second pulses overlap in the frequency domain. As discussed above in relation to step 202 of FIG. 27, such an operating condition may be handled by filtering the measurement signal in the time domain. However, the monitoring precision may be increased further by combining the inventive monitoring technique with a phase-locking technique or a beating detection method, to be described in the following.

The phase-locking technique involves controlling the first/second pulse generator 3, 3' so as to synchronize the pulse rate of the first and second pulse generators 3, 3' while applying a phase difference between the first and second pulses. Thereby, the first and second pulses will be separated in time, and may be detected using the time domain analysis according to the first and/or second inventive concepts. The phase difference may be approximately 180°, since this may maximize the separation of the first and second pulses in the time domain. The phase-locking technique may be activated when it is detected that the frequency of the second pulse generator approaches a frequency of the first pulse generator, or vice versa.

The beating detection method is an alternative or complementary monitoring technique which involves evaluating the presence or absence of a beating signal in the measurement signal to determine the integrity of the fluid connection. The beating signal manifests itself as an amplitude modulation of the measurement signal and is formed by interference between pressure waves generated by the first pulse generator and pressure waves generated by the second pulse generator. Instead of trying to identify second pulses in the measurement signal, the presence of second pulses is identified via the secondary effect of beating. Generally, beating is a phenomenon which is especially noticeable when two signals with closely spaced frequencies are added together. Thus, the beating signal detection is inherently well-suited to be used when the first and second pulses are closely spaced in the frequency domain. The beating signal may or may not be detected by analysing the measurement signal in the time domain. Suitably, the beating detection involves obtaining one or more specific frequencies related to the first pulse generator, and creating at least one filtered measurement signal in which all but one of said specific frequencies are removed. The beating signal may then be detected by determining an envelope of the filtered measurement signal. The beating detection method is the subject of Applicant's PCT publication WO2009/127683, which is incorporated herein in its entirety by reference.

It is to be understood that in any one of the above combinations, the different monitoring techniques may be carried out in series, in any order, or in parallel.

Performance Improvements

The performance of the different methods for monitoring the integrity of a fluid connection as described herein may be improved by applying any of the following variations.

Hypothesis Test

The determination of the integrity of the fluid connection between the first and second fluid containing systems may be represented by a hypothesis test. In this hypothesis test, the above-mentioned evaluation parameter value $\beta$ is compared to a threshold. The output of the hypothesis is a decision, which may be "intact fluid connection" ($H_1$) if $\beta > \gamma_1$, "compromised fluid connection" ($H_0$) if $\beta < \gamma_0$, or "uncertain decision" if $\gamma_0 \leq \beta \leq \gamma_1$, wherein $\gamma_0$ and $\gamma_1$ are different thresholds.

Magnitude Dependent Monitoring Technique

The monitoring technique may be dynamically adjusted based on the magnitude of the first and/or second pulses in the measurement signal and/or in the reference signal. The dynamic adjustment may affect the process for obtaining timing information and/or the process for obtaining the parameter value based on the measurement signal.

For example, if the magnitude (e.g. amplitude) of second pulses in the reference signal are found to be smaller than the magnitude (e.g. amplitude) of second pulses in the measurement signal, or smaller than a predetermined absolute limit, the timing information may be obtained based on the measurement signal, whereas the timing information otherwise is obtained based on the reference signal (or vice versa). Thus, with reference to FIG. 34, step 601 is adjusted based on the magnitude of second pulses.

In another example, if the magnitude (amplitude) of the second pulses in the reference signal again are found to be too small, the monitoring method may switch to another method for detecting presence or absence of second pulses in the measurement signal, e.g. a method that operates without timing information (e.g. by omitting steps 601, 602, 202 and 202' in FIG. 34).

In the above examples, if the magnitude of first and second pulses are covariant entities, the dynamic adjustment may alternatively be based on the magnitude of first pulses, or the magnitude of a combination of first and second pulses.

Monitoring Technique Based on Patient Data Records

When the second fluid containing system (S2 in FIG. 26) is a blood system of a patient, the monitoring method may be configured to access and use patient-specific information, i.e. existing data records for the patient, e.g. obtained in earlier treatments of the same patient. The patient-specific information may be stored in an internal memory of the surveillance device (25 in FIG. 26), on an external memory which is made accessible to the surveillance device, or on a patient card where the information is e.g. transmitted wirelessly to the surveillance device, e.g. by RFID (Radio Frequency IDentification). For example, the surveillance device may compare the filtered measurement signal, or a parameter derived therefrom, to the patient-specific information. If large differences are identified, a warning may be issued and/or the monitoring technique may be modified (or chosen according to a predetermined table). Furthermore, the patient-specific information may be used by the surveillance device to optimize the monitoring technique by e.g. determining personal threshold values for use in the foregoing algorithms/processes. The patient-specific information may also be used by the surveillance device to determine if an alternative monitoring technique or combinations of monitoring techniques should be used.

Use of Information from Regular Stops of First Pulse Generator

In one embodiment, the first pulse generator is regularly (intermittently or periodically) stopped, and the measurement signal and/or reference signal is analysed for determination of amplitude, frequency and phase of second pulses. This resulting information may then be used to achieve detection by the above-mentioned phase-locking technique.

Alternatively or additionally, if the magnitude (e.g. amplitude) of the second pulse(s) detected during such a stop is smaller than a certain limit (chosen with a margin for safe detection), an alert on "uncertain detection" may be issued. Alternatively, if the magnitude is smaller than another limit, the first pulse generator may be actively controlled to be stopped at specific time intervals, where the information obtained during each stop may be used to modify the monitoring technique. For example, the thus-obtained information may be used to change (or add) threshold values in the foregoing algorithms/processes, or to determine if an alternative monitoring technique or combinations of monitoring techniques should be used. In another example, if the thus-obtained information indicates the pulse rate of second pulses, a dedicated bandpass filter (e.g. centred on the thus-obtained pulse rate) may be operated on the measurement signal/filtered measurement signal/evaluation segment to further improve the input to the process for obtaining timing information (cf. step 602 in FIG. 31) and/or the process for obtaining the parameter value based on the measurement signal (cf. step 203/603 in FIGS. 27 and 34). In one embodiment, such a bandpass filter is applied if the rates of first and second pulses are found to differ by more than a certain limit, e.g. about 10%.

In another embodiment, the first pulse generator is selectively controlled so as to reduce the flow rate through the fluid arrangement. By reducing the flow rate, it is possible to accept a longer response time of the monitoring process to a fault condition, while such a longer response time may serve to improve the precision of the monitoring process in detecting fault conditions.

The invention has mainly been described above with reference to a few embodiments. However, as is readily appreciated by a person skilled in the art, other embodiments than the ones disclosed above are equally possible within the scope and spirit of the invention, which is defined and limited only by the appended patent claims.

The inventive monitoring techniques are applicable when the measurement signal originates from a pressure sensor arranged to sense the pressure in an extracorporeal blood flow circuit. In such an embodiment, the first fluid containing system S1 is the extracorporeal blood flow circuit, the second fluid containing system S2 is human blood system, and the fluid connection C may be formed by a connection between an access device and a blood vessel access. The first pulses may originate from the pumping device in the extracorporeal blood flow circuit (and/or any other pulse generator within or associated with the extracorporeal blood flow circuit), and the second pulses may originate from the human heart, and the integrity of the fluid connection is determined by applying the first and/or second inventive concepts to detect the presence/absence of the second pulses in the measurement signal.

The pressure (measurement) signal may originate from any conceivable type of pressure sensor, e.g. operating by resistive, capacitive, inductive, magnetic or optical sensing, and using one or more diaphragms, bellows, Bourdon tubes, piezo-electrical components, semiconductor components, strain gauges, resonant wires, etc.

Further, the disclosed embodiments are applicable for surveillance of all types of extracorporeal blood flow circuits in which blood is taken from a patient's circulation to have a process applied to it before it is returned to the circulation. Such blood flow circuits include hemodialysis, hemofiltration, hemodiafiltration, plasmapheresis, apheresis, extracorporeal membrane oxygenation, assisted blood circulation, and extracorporeal liver support/dialysis.

Further, the inventive monitoring techniques are applicable to any type of pumping device that generates pressure pulses in the first fluid containing system, not only rotary peristaltic pumps as disclosed above, but also other types of positive displacement pumps, such as linear peristaltic pumps, diaphragm pumps, as well as centrifugal pumps Still further, the inventive monitoring techniques are applicable also for monitoring the integrity of the fluid connection between the blood vessel access and the arterial needle based on a measurement signal from one or more arterial pressure sensors. Such a monitoring technique may provide a faster detection of malfunction than the conventional air detector, and more reliable detection of malfunction than conventional comparison of average pressure levels to threshold values. In such an application, the aforesaid reference signal may be derived from one or more venous pressure sensors in the extracorporeal blood flow circuit.

Also, it is to be understood that the monitoring technique is equally applicable to single-needle dialysis.

The inventive monitoring techniques are also applicable when the measurement signal originates from a pressure sensor arranged to sense the pressure in the human blood system. In such an embodiment, the first fluid containing system S1 is the human blood system, the second fluid containing system S2 is the extracorporeal blood flow circuit, and the fluid connection C may be formed by a connection between an access device and a blood vessel access. The first pulses thus originate from the human heart, and the second pulses originate from the pumping device in the extracorporeal blood flow circuit (and/or any other pulse generator within or associated with the extracorporeal blood flow circuit), and the integrity of the fluid connection is determined by applying the first and/or second inventive concepts to detect the presence/absence of the second pulses in the measurement signal.

The above-described inventive concepts may also be applicable to monitoring the integrity of fluid connections for transferring other liquids than blood. Likewise, the fluid connections need not be provided in relation to a human, but may be provided in relation to any other type of fluid containing system.

In one example, the fluid connection is provided between a blood processing circuit and a container/machine, wherein blood is pumped from one container/machine through a blood processing device in the blood processing circuit and back to the container/machine, or to another container/machine downstream of the blood processing device. The blood processing device may be any known device configured to modify and/or analyse the blood.

In a further example, the fluid connection is provided between a dialyser and a reprocessing system, which reprocesses the dialyser by pumping water, optionally together with suitable chemicals through the dialyser. An example of a dialyser reprocessing system is known from US2005/0051472.

In another example, the fluid connection is provided between a dialysate supply and a dialysate regeneration system, which circulates dialysate from the dialysate supply through a dialysate regeneration device and back to the supply. An example of a dialysate regeneration device is known from WO 05/062973.

In yet another example, the fluid connection is provided in an arrangement for priming an extracorporeal blood flow circuit by pumping a priming fluid from a supply via the blood flow circuit to a dialyser. The priming fluid may e.g. be dialysis solution, saline, purified water, etc.

In a still further example, the fluid connection is provided in an arrangement for cleaning and disinfecting the dialysis solution flow path of a dialysis machine, which pumps a cleaning fluid via a flow path to a dialyser/dialyser tubing. The cleaning fluid may e.g. be hot water, a chemical solution, etc.

In a further example, the fluid connection is provided in an arrangement for purifying water, which pumps water from a supply through a purifying device. The purifying device may use any known water purification technique, e.g. reverse osmosis, deionization or carbon absorption.

In another example, the fluid connection is provided in an arrangement for providing purified water to a dialysis machine, e.g. to be used in the preparation of dialysis solution therein.

In all of these examples, and in other applications related to medical treatment of human or animal patients, it may be vital to monitor the integrity of the fluid connection. Such monitoring may be accomplished according to the inventive concepts disclosed herein.

End Appendix B

The invention claimed is:

1. A blood treatment device comprising:
   an extracorporeal blood flow circuit configured to be coupled to a cardiovascular system of a subject;
   at least one pressure sensor configured to generate measurement data based on pressure present within the extracorporeal blood flow circuit; and
   a monitoring device for predicting rapid symptomatic blood pressure decrease during the subject's blood treatment, the monitoring device including:
      an input for receiving the measurement data from the at least one pressure sensor in the extracorporeal blood flow circuit configured to be coupled to the cardiovascular system of the subject, the measurement data comprising a time sequence of pulse shape parameters representing pressure variations in at least one blood vessel of the subject; and a data analysis part configured to repeatedly receive the pulse shape parameters, calculate a pulse measure representing an overall magnitude determined by averaging a plurality of magnitudes from a plurality of the pulse shape parameters within a time window, and cause an output signal to be generated when the pulse measure fulfils a decision criterion, the output signal indicating a predicted rapid symptomatic blood pressure decrease in the subject, wherein, when the pulse measure fulfils the decision criterion, the output signal causes the blood treatment device to (i) issue an alarm indicating that a treatment parameter of the subject's blood treatment should be adjusted, and (ii) adjust the treatment parameter of the subject's blood treatment.

2. The blood treatment device of claim 1, wherein the decision criterion includes when the pulse measure crosses a threshold.

3. The blood treatment device of claim 1, wherein the decision criterion includes when the pulse measure remains outside of a threshold for a predefined test period.

4. The blood treatment device of claim 1, wherein the data analysis part is further configured to:
obtain a reference measure;
calculate, during a measurement period, a respective pulse measure based on each of a number of the received pulse shape parameters;
investigate, during the measurement period, whether or not the decision criterion, which is given relative to the reference measure, is fulfilled based on one or more of the respective pulse measures; and
if so, cause the output signal to be generated.

5. The blood treatment device according to claim 4, wherein the respective pulse measure is a pulse magnitude measure of a pulse shape parameter.

6. The blood treatment device according to claim 5, wherein the pulse magnitude measure is any of a peak-to-peak measure, an integration measure, an energy measure, and a frequency spectrum intensity measure calculated for the pulse shape parameter.

7. The blood treatment device according to claim 4, wherein the respective pulse measure is a statistical dispersion measure of a sequence of pulse magnitude measures.

8. The blood treatment device of claim 7, wherein the data analysis part is further configured to:
investigate whether one or more of the pulse magnitude measures fulfils a second decision criterion relative to a second reference measure, and cause the output signal to be generated as a function of both said decision criterion and said second decision criterion.

9. The blood treatment device according to claim 7, wherein the statistical dispersion measure is any of a variance, a standard deviation, a coefficient of a variation, a variance-to-mean, a sum of differences, and an energy measure.

10. The blood treatment device according to claim 4, wherein the reference measure is a threshold value, and the decision criterion is fulfilled when the respective pulse measure passes the threshold value.

11. The blood treatment device according to claim 10, wherein the threshold value is given by a predefined value.

12. The blood treatment device according to claim 4, wherein the data analysis part further is configured to:

calculate as the reference measure an initial pulse measure based on at least one pulse shape parameter received at a first instance; and
store the initial pulse measure in a memory device associated with the monitoring device;
wherein the measurement period is subsequent to the first instance.

13. The blood treatment device according to claim 12, wherein the data analysis part is configured to regard the decision criterion as fulfilled if:
an examined pulse measure fulfils a first partial decision criterion calculated based on the initial pulse measure; and
a predetermined amount of the respective pulse measures calculated within a subsequent test period fulfils a second partial decision criterion.

14. The blood treatment device according to claim 13, wherein the predetermined amount is a value representing approximately 50% to approximately 100% of the respective pulse measures calculated for the pulse shape parameters received within the test period.

15. The blood treatment device according to claim 13, wherein the predetermined amount represents all the respective pulse measures calculated for the pulse shape parameters received within the test period.

16. The blood treatment device according to claim 13, wherein the test period is an interval selected from a range extending from approximately one minute to approximately fifteen minutes.

17. The blood treatment device according to claim 16, wherein the test period is approximately five minutes long.

18. The blood treatment device according to claim 12, wherein the data analysis part is configured to calculate the decision criterion by:
normalizing the initial pulse measure, and
dividing the normalized initial pulse measure by a predefined denominator.

19. The blood treatment device according to claim 18, wherein
the data analysis part is configured to, during the measurement period, calculate the respective pulse measure for the received pulse shape parameter by dividing an original measure with the initial pulse measure.

20. The blood treatment device according to claim 18, wherein the respective pulse measure is a pulse magnitude measure, and the predefined denominator is a value selected from a range extending from approximately 1.2 to approximately 5.

21. The blood treatment device according to claim 18, wherein the respective pulse measure is a statistical dispersion measure, and the predefined denominator is a value selected from a range extending from approximately 0.2 to approximately 0.8.

22. The blood treatment device according to a claim 12, which is configured to predict rapid symptomatic blood pressure decrease in the subject undergoing blood treatment, wherein the data analysis part is configured to calculate the initial pulse measure based on one or more pulse shape parameters received during an initial phase of the blood treatment.

23. The blood treatment device according to claim 1, wherein the pulse measure relates to one or more physiological pulses in the pulse shape parameter, said one or more physiological pulses originating from a physiological pulse generator in the subject.

24. The blood treatment device according to claim 23, wherein each pulse shape parameter corresponds to the time window in a pressure signal formed by the measurement data.

25. The blood treatment device according to claim 24, wherein the time window is selected such that each pulse shape parameter comprises at least one physiological pulse originating from the physiological pulse generator in the subject.

26. The blood treatment device according to claim 23, wherein the blood treatment device includes at least one pumping device, wherein the at least one pressure sensor is arranged in the extracorporeal blood flow circuit to detect interference pulses originating from said at least one pumping device and physiological pulses originating from the physiological pulse generator in the subject.

27. The blood treatment device according to claim 26, wherein the data analysis part is further configured to generate, based on the pressure signal formed by the measurement data, a time-dependent monitoring signal in which the interference pulses are essentially eliminated, whereupon the data analysis part obtains the pulse shape parameters from the time-dependent monitoring signal.

28. The blood treatment device according to claim 26, wherein the data analysis part is configured to obtain a pulse profile which is a predicted temporal signal profile of the interference pulses, and to filter the measurement data in the time window, using the pulse profile, to minimize the interference pulses while retaining the physiological pulses.

29. The blood treatment device according to claim 26, wherein the data analysis part is further configured to calculate a rate of physiological pulses in the monitoring signal, or in a reference signal obtained from a reference sensor, and to cause a pumping frequency of said at least one pumping device to be controlled in relation to the rate of physiological pulses.

30. The blood treatment device according to claim 26, wherein the data analysis part is configured to receive the pulse shape parameters while said at least one pumping device is intermittently set in a disabled state.

31. The blood treatment device according to claim 26, wherein the physiological pulse generator is at least one of a heart, a breathing system, and a vasomotor affected by an autonomic nervous system.

32. The blood treatment device according to claim 1, wherein said extracorporeal blood flow circuit includes the at least one pressure sensor for generating the measurement data comprising the time sequence of pulse shape parameters representing pressure variations in the at least one blood vessel of the subject.

33. The blood treatment device according to claim 1, which includes a dialysis machine configured to perform extracorporeal blood treatment of the subject and comprising the extracorporeal blood flow circuit configured to be coupled to the cardiovascular system of the subject, said extracorporeal blood flow circuit comprising the at least one pressure sensor for generating the measurement data comprising the time sequence of pulse shape parameters representing pressure variations in the at least one blood vessel of the subject.

34. The blood treatment device according to claim 33, wherein the dialysis machine is configured to, based on the output signal, activate systems to counter-act the occurrence of a hypotension event including any of adjusting a rate of fluid removal from the subject by reducing or stopping the rate of fluid removal in case of fulfilled decision criterion, increasing the conductivity in the dialysis fluid, supplying a saline bolus to a blood line configured to connect to the cardiovascular system of the subject, adjusting the positioning of the subject, and setting a dialysis monitor in a bypass.

35. The blood treatment device of claim 1, wherein the monitoring device comprises a non-transitory memory unit and a processor executing instructions stored in the memory unit, the instructions causing the monitoring device to:
repeatedly receive measurement data from the at least one pressure sensor blood pressure in the cardiovascular system of the subject, the measurement data including the sequence of pulse shape parameters representing pressure variations in the at least one blood vessel of the subject, and
generating the output indicating the predicted rapid symptomatic blood pressure decrease in the subject when the pulse shape parameters fulfill the defined decision criterion.

36. The blood treatment device of claim 35, wherein the instructions cause the monitoring device to:
obtain a reference measure;
calculate a respective pulse measure based on each of a number of the received pulse shape parameters, and
generate the output signal upon a determination that the decision criterion, which is given relative to the reference measure, is fulfilled based on at least one of the respective pulse measures.

37. The blood treatment device of claim 1, wherein the treatment parameter adjustment includes at least one of: (i) changing a rate of fluid removal from the subject; (ii) supplying a saline bolus to the extracorporeal blood flow circuit; (iii) changing a conductivity of dialysis fluid; (iv) adjusting a positioning of the subject; or (v) setting the blood treatment device in bypass.

38. A blood treatment device comprising:
an extracorporeal blood flow circuit configured to be coupled to a cardiovascular system of a subject;
at least one pressure sensor configured to generate measurement data based on pressure within the extracorporeal blood flow circuit;
an input for receiving the measurement data from the at least one pressure sensor in the extracorporeal blood flow circuit configured to be coupled to the cardiovascular system of the subject, the measurement data comprising a time sequence of pulse shape parameters representing pressure variations in at least one blood vessel of the subject; and
a data analysis part configured to repeatedly receive the pulse shape parameters, calculate a pulse measure representing an overall magnitude determined by averaging a plurality of magnitudes from a plurality of the pulse shape parameters within a time window, and cause an output signal to be generated when the pulse measure fulfils a decision criterion, the output signal indicating a predicted rapid symptomatic blood pressure decrease in the subject,
wherein, when the pulse measure fulfils the decision criterion, the output signal causes the blood treatment device to (i) issue an alarm indicating that a treatment parameter of the subject's blood treatment should be adjusted, and (ii) adjust the treatment parameter of the subject's blood treatment.

39. The blood treatment device of claim 38, wherein the decision criterion includes when the pulse measure crosses a threshold.

40. The blood treatment device of claim 38, wherein the decision criterion includes when the pulse measure remains outside of a threshold for a predefined test period.

\* \* \* \* \*